(12) United States Patent
Kato et al.

(10) Patent No.: US 10,597,403 B2
(45) Date of Patent: Mar. 24, 2020

(54) CONDENSED CYCLIC COMPOUND, COMPOSITION INCLUDING THE CONDENSED CYCLIC COMPOUND, ORGANIC LIGHT-EMITTING DEVICE INCLUDING THE CONDENSED CYCLIC COMPOUND, AND METHOD OF MANUFACTURING THE ORGANIC LIGHT-EMITTING DEVICE

(71) Applicant: SAMSUNG ELECTRONICS CO., LTD., Suwon-si, Gyeonggi-do (KR)

(72) Inventors: Fumiaki Kato, Yokohama (JP); Satoshi Inayama, Yokohama (JP); Norihito Ishii, Yokohama (JP); Katsunori Shibata, Yokohama (JP); Mitsunori Ito, Yokohama (JP)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 152 days.

(21) Appl. No.: 15/388,957

(22) Filed: Dec. 22, 2016

(65) Prior Publication Data

US 2017/0174705 A1    Jun. 22, 2017

(30) Foreign Application Priority Data

Dec. 22, 2015   (JP) ................. 2015-250531

(51) Int. Cl.

| | | |
|---|---|---|
| *H01L 51/54* | (2006.01) | |
| *C09K 11/06* | (2006.01) | |
| *C07D 498/06* | (2006.01) | |
| *C07D 403/10* | (2006.01) | |
| *H01L 51/00* | (2006.01) | |
| *C09K 11/02* | (2006.01) | |
| *C07D 405/14* | (2006.01) | |
| *H01L 51/50* | (2006.01) | |

(52) U.S. Cl.
CPC ......... *C07D 498/06* (2013.01); *C07D 403/10* (2013.01); *C07D 405/14* (2013.01); *C09K 11/025* (2013.01); *H01L 51/0067* (2013.01); *H01L 51/0072* (2013.01); *H01L 51/0073* (2013.01); *H01L 51/0085* (2013.01); *H01L 51/5016* (2013.01); *H01L 2251/5384* (2013.01)

(58) Field of Classification Search
CPC .. C07D 209/82; C07D 403/00; C07D 403/10; C07D 403/12; C07D 403/14; C07D 405/00; C07D 405/10; C07D 405/12; C07D 405/14; C07D 498/00; C07D 498/02; C07D 498/06; C09K 11/025; C09K 11/06; C09K 2211/00; C09K 2211/10; C09K 2211/1007; C09K 2211/1029; H01L 51/0032; H01L 51/005; H01L 51/0059; H01L 51/006; H01L 51/0067; H01L 51/0072; H01L 51/0073; H01L 51/0074; H01L 51/0085; H01L 51/50; H01L 51/5012; H01L 51/5016; H01L 2251/5384

USPC ....... 428/690, 691, 917, 411.4, 336; 427/58, 427/66; 313/500–512; 257/40, 88–104, 257/E51.001–E51.052; 252/301.16–301.35

See application file for complete search history.

(56) References Cited

U.S. PATENT DOCUMENTS

| | | | |
|---|---|---|---|
| 6,670,054 | B1 | 12/2003 | Hu et al. |
| 9,911,925 | B2 * | 3/2018 | Lee ..................... H01L 51/0067 |
| 2011/0006670 | A1 * | 1/2011 | Katakura ............. C07D 403/10 |
| | | | 313/504 |
| 2013/0105787 | A1 | 5/2013 | Tanaka et al. |
| 2014/0151647 | A1 * | 6/2014 | Mizuki ................. H05B 33/20 |
| | | | 257/40 |
| 2015/0045551 | A1 | 2/2015 | Yoshinaga et al. |
| 2015/0228908 | A1 | 8/2015 | Lee et al. |
| 2016/0072078 | A1 | 3/2016 | Lee et al. |
| 2016/0204359 | A1 | 7/2016 | Lee et al. |
| 2016/0268517 | A1 | 9/2016 | Inoue et al. |
| 2016/0351826 | A1 | 12/2016 | Kim et al. |

FOREIGN PATENT DOCUMENTS

| | | |
|---|---|---|
| CN | 104178124 A | 5/2013 |
| CN | 104045595 A | 6/2014 |
| EP | 2991128 A1 | 3/2016 |
| JP | 2010135467 A * | 6/2010 |
| JP | 2012049518 A * | 3/2012 |
| KR | 10-2013-0134426 A | 12/2013 |
| KR | 10-2015-0084657 A | 7/2015 |
| KR | 10-2015-0094398 A | 8/2015 |
| KR | 10-2015-0127548 A | 11/2015 |
| KR | 10-2015-0141147 A | 12/2015 |
| KR | 10-2016-0026744 A | 3/2016 |
| KR | 10-2016-0046077 A | 4/2016 |

(Continued)

OTHER PUBLICATIONS

Machine translation of JP-2012049518. (Year: 2012).*

(Continued)

*Primary Examiner* — Andrew K Bohaty
(74) *Attorney, Agent, or Firm* — Cantor Colburn LLP

(57) ABSTRACT

A condensed cyclic compound represented by Formula (1):

Formula (1)

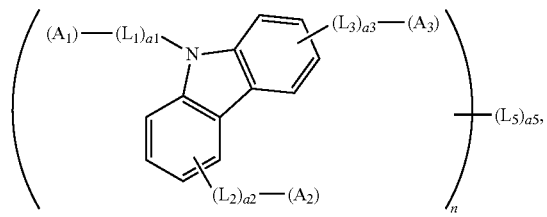

wherein, in Formula (1), groups and variables are the same as described in the specification.

18 Claims, 1 Drawing Sheet

(56) References Cited

FOREIGN PATENT DOCUMENTS

| | | |
|---|---|---|
| WO | 2012-008281 A1 | 1/2012 |
| WO | 2012-108388 A1 | 8/2012 |
| WO | 2013-100540 A1 | 7/2013 |
| WO | 2013-146117 A1 | 10/2013 |
| WO | 2013-147117 A1 | 10/2013 |
| WO | 2013-175747 A1 | 11/2013 |
| WO | 2013-191177 A1 | 12/2013 |
| WO | 2014-015931 A1 | 1/2014 |
| WO | 2015-016498 A1 | 2/2015 |
| WO | 2015-051869 A1 | 4/2015 |
| WO | 2015-056993 A1 | 4/2015 |
| WO | 2015-137471 A1 | 9/2015 |
| WO | 2015-167199 A1 | 11/2015 |
| WO | 2015-169412 A1 | 11/2015 |

OTHER PUBLICATIONS

Machine translation of JP-2010135467. (Year: 2010).*
Extended Search Report dated Apr. 3, 2017, issued for the European Patent Application No. 16205894.5-1452.

* cited by examiner

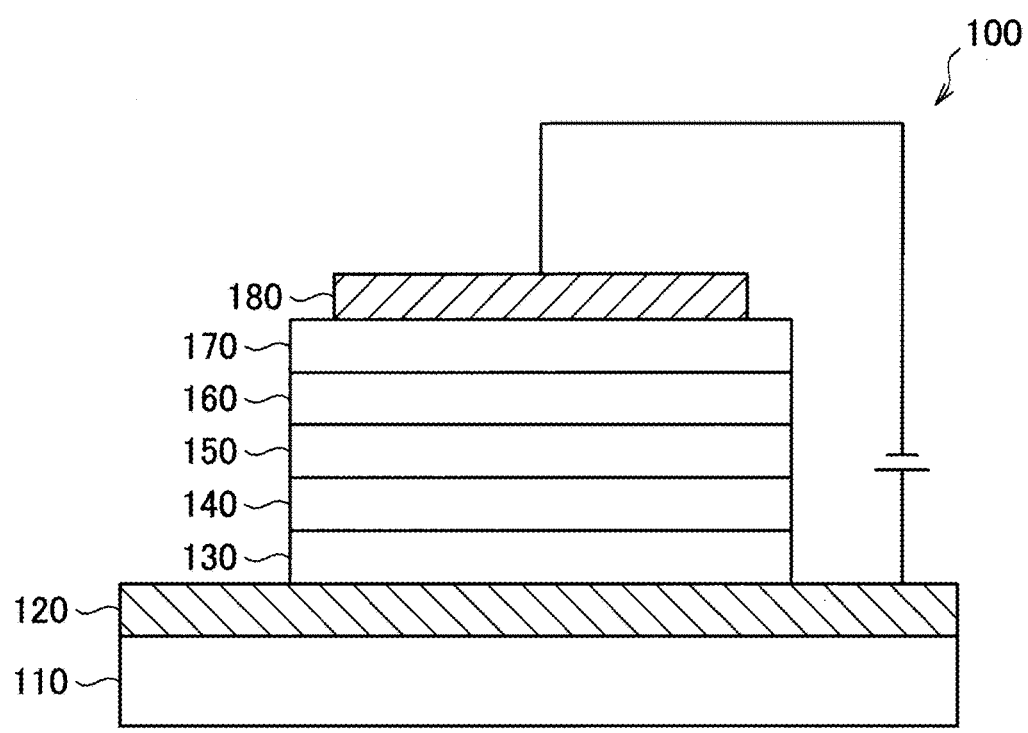

CONDENSED CYCLIC COMPOUND, COMPOSITION INCLUDING THE CONDENSED CYCLIC COMPOUND, ORGANIC LIGHT-EMITTING DEVICE INCLUDING THE CONDENSED CYCLIC COMPOUND, AND METHOD OF MANUFACTURING THE ORGANIC LIGHT-EMITTING DEVICE

CROSS-REFERENCE TO RELATED APPLICATION

This application claims priority to Japanese Patent Application No. 2015-250531, filed on Dec. 22, 2015, in the Japanese Patent Office, and all the benefits accruing therefrom under 35 U.S.C. § 119, the content of which is incorporated herein in its entirety by reference.

BACKGROUND

1. Field

One or more embodiments relate to a condensed cyclic compound, a composition including the condensed cyclic compound, an organic light-emitting device including the condensed cyclic compound, and a method of manufacturing the organic light-emitting device.

2. Description of the Related Art

Research efforts have recently been actively carried out to develop display apparatuses, mobile apparatuses, lighting apparatuses, or the like using organic light-emitting devices that are self-emission devices.

An organic light-emitting device has an organic layer including a light-emitting material. The light-emitting material is excited by recombination of holes and electrons in the organic layer, and light is generated when the excited light-emitting material transits from an excited state to a ground state.

Research efforts into various types of materials constituting the organic layer have been actively carried out to improve light emission efficiency, light emission lifespan, and driving voltage characteristics of the organic light-emitting device.

On the other hand, in order to manufacture a large-scale organic light-emitting device at a low cost, the use of solution coating instead of vacuum deposition in forming an organic layer is desired. Compared to vacuum deposition, the use of solution coating may increase use efficiency of a material for forming an organic layer and may facilitate the formation of a large-scale film without using expensive vacuum devices. Accordingly, solution coating is expected as an efficient method of manufacturing an organic light-emitting device.

SUMMARY

In an organic light-emitting device, a certain driving voltage is applied to an organic layer so as to inject holes and electrons into the organic layer. At this time, driving heat may be generated in the organic layer. An existing compound does not have a sufficient heat resistance to the driving heat. As a result, the existing compound included in the organic layer may be degraded by the driving heat. Thus, the organic light-emitting device does not have a satisfactory light emission lifespan.

In a solution coating method, after a solution in which an organic material is dissolved in a solvent is coated on a certain region to form a coating film, the solvent that dissolves the organic material needs be removed by drying the coating layer by heat or the like. In such a solvent removing process, the organic material needs to have an excellent heat resistance so as to improve uniformity of the dried coating film. When a thickness of the dried coating film is not uniform, a stress may occur in a voltage applied to the manufactured organic light-emitting device. Thus, the organic light-emitting device may have an unsatisfactory light emission lifespan.

One or more embodiments include a condensed cyclic compound capable of improving thermal stability of an organic layer, and thus, capable of improving a light emission lifespan of an organic light-emitting device, a composition including the condensed cyclic compound, an organic light-emitting device including the condensed cyclic compound, and a method of manufacturing the organic light-emitting device.

Additional aspects will be set forth in part in the description which follows and, in part, will be apparent from the description, or may be learned by practice of the presented embodiments.

According to one or more embodiments, a condensed cyclic compound is represented by Formula (1):

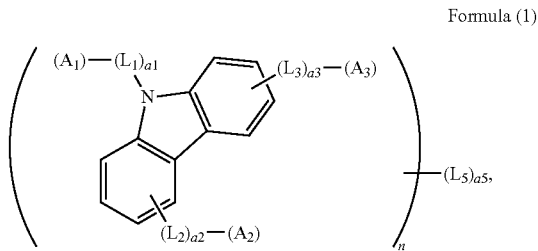

Formula (1)

wherein, in Formula (1), $L_1$ to $L_3$ and $L_5$ may each independently be selected from a single bond, *—C(=O)—*', *—C(=S)—*', *—O—*', *—S—*', *—N($R_5$)—*', a substituted or unsubstituted $C_2$-$C_{60}$ alkylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,

* and *' each indicate a binding site to a neighboring atom, a1 to a3 and a5 may each independently be an integer from 1 to 10, $(L_5)_{a5}$ may be an n-valent linking group or a single bond, wherein n may be a natural number greater than or equal to one, when n is one, $(L_5)_{a5}$ may not exist, when n is a natural number greater than or equal to two, at least one of *-$(L_1)_{a1}$-$(A_1)$, *-$(L_2)_{a2}$-$(A_2)$, and *-$(L_3)_{a3}$-$(A_3)$ may be linked to $(L_5)_{a5}$ or may be a single bond linked to $(L_5)_{a5}$, i) $A_1$ to $A_3$ and $R_5$ may each independently be linked to $(L_5)_{a5}$;

ii) $A_1$ to $A_3$ and $R_5$ may be each independently a single bond linked to $(L_5)_{a5}$;

iii) $A_1$ to $A_3$ and $R_5$ may each independently be a group represented by one of Formulae (2) to (5); or iv) $A_1$ to $A_3$ and $R_5$ may each independently be selected from a substituted or unsubstituted $C_1$-$C_{60}$ alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, the group represented by *-$(L_2)_{a2}$-$(A_2)$ may be linked to the third or fourth carbon of a carbazole core of Formula (1), the group represented by *-$(L_3)_{a3}$-$(A_3)$ may be linked to the fifth or sixth carbon of the carbazole core of Formula (1), and * in the group represented by *-$(L_2)_{a2}$-$(A_2)$ and the group represented by *-$(L_3)_{a3}$-$(A_3)$ indicates a binding site to a carbon atom of the carbazole core of Formula (1), and at least one of $A_1$ to $A_3$ may be selected from groups represented by Formulae (2) to (5), provided that, when i) n is 2, ii) $(L_5)_{a5}$ is a single bond, and iii) *-$(L_3)_{a3}$-$(A_3)$ is a single bond linked to $(L_5)_{a5}$, $A_2$ is selected from groups represented by Formulae (2) to (5):

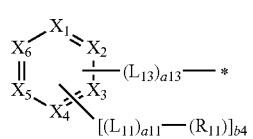

Formula (2)

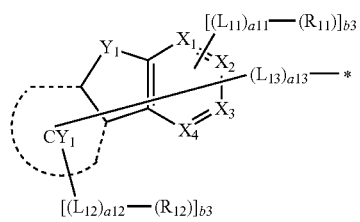

Formula (3)

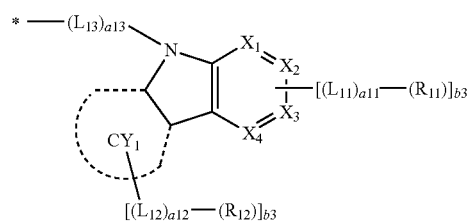

Formula (4)

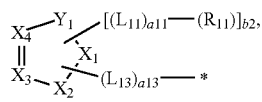

Formula (5)

wherein, in Formulae (2) to (5), $X_1$ may be N, carbon linked to *-$(L_{11})_{a11}$-$(R_{11})$, or carbon linked to $L_{13}$, $X_2$ may be N, carbon linked to *-$(L_{11})_{a11}$-$(R_{11})$, or carbon linked to $L_{13}$, $X_3$ may be N, carbon linked to *-$(L_{11})_{a11}$-$(R_1)$, or carbon linked to $L_{13}$, $X_4$ may be N, carbon linked to *-$(L_{11})_{a11}$-$(R_{11})$, or carbon linked to $L_{13}$, $X_5$ may be N, carbon linked to *-$(L_{11})_{a11}$-$(R_{11})$, or carbon linked to $L_{13}$, and $X_6$ may be N, carbon linked to *-$(L_{11})_{a11}$-$(R_{11})$, or carbon linked to $L_{13}$, provided that $X_1$ to $X_4$ in Formula (4) are not carbon linked to $L_{13}$, $Y_1$ may be O, S, N($R_{13}$), or C($R_{14}$)($R_{15}$), and $R_{14}$ and $R_{15}$ may optionally be linked to form a saturated or unsaturated ring, $CY_1$ may be a $C_5$-$C_{30}$ carbocyclic group or a $C_2$-$C_{30}$ heterocyclic group, at least one of $X_1$ to $X_6$ in Formula (2) may be N, in Formulae (3) and (4), at least one of $X_1$ to $X_4$ may be N, or $CY_1$ may be a π electron-depleted nitrogen-containing $C_2$-$C_{30}$ heterocyclic group, at least one of $X_1$ to $X_4$ in Formula (5) may be N, $L_{11}$ to $L_{13}$ may each independently be selected from a single bond, a substituted or unsubstituted $C_2$-$C_{60}$ alkylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11 to a13 may each independently be an integer selected from 1 to 10, $R_{11}$ to $R_{15}$ may each independently be selected from hydrogen, deuterium, —F, —Cl, —Br, —I, -$CD_3$, -$CD_2H$, -$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), and —C(=O)($Q_1$), b2 may be an integer selected from 0 to 2, b3 may be an integer selected from 0 to 3, b4 may be an integer selected from 0 to 4,

* indicates a binding site to a neighboring atom, and at least one substituent of the substituted $C_2$-$C_{60}$ alkylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group in Formulae (1) to (5) may be selected from:

deuterium, —F, —Cl, —Br, —I, -CD$_3$, -CD$_2$H, -CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, -CD$_3$, -CD$_2$H, -CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), and —C(=O)($Q_{11}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, -CD$_3$, -CD$_2$H, -CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), and —C(=O)($Q_{21}$); and —Si($Q_{31}$)($Q_{32}$)($Q_{33}$), —N($Q_{31}$)($Q_{32}$), and —C(=O)($Q_{31}$), wherein $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, a $C_1$-$C_{20}$ alkyl group, a $C_1$-$C_{20}$ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, and a diphenyldibenzothiophenyl group.

According to an aspect of the present disclosure, an organic layer having excellent thermal stability and an organic light-emitting device having improved light emission lifespan may be provided.

According to one or more embodiments, a composition includes the condensed cyclic compound represented by Formula (1) and a liquid medium.

According to an aspect of the present disclosure, an organic layer having excellent thermal stability and an organic light-emitting device having improved light emission lifespan may be provided, and a composition suitable for solution coating may be provided.

According to one or more embodiments, an organic light-emitting device includes:

a first electrode, a second electrode, and an organic layer disposed between the first electrode and the second electrode, wherein the organic layer includes an emission layer, and wherein the organic layer includes a layer including the condensed cyclic compound represented by Formula (1).

According to an aspect of the present disclosure, an organic layer having excellent thermal stability and an organic light-emitting device having improved light emission lifespan may be provided.

According to one or more embodiments, a method of manufacturing an organic light-emitting device including a first electrode, a second electrode, and an organic layer disposed between the first electrode and the second electrode, wherein the organic layer includes an emission layer, and wherein the organic layer includes a layer including the condensed cyclic compound represented by Formula (1), includes:

forming a layer including the condensed cyclic compound by solution coating using a composition including the condensed cyclic compound and a liquid medium.

According to an aspect of the present disclosure, an organic layer having excellent thermal stability and a large-sized organic light-emitting device having improved light emission lifespan may be provided.

BRIEF DESCRIPTION OF THE DRAWING

These and/or other aspects will become apparent and more readily appreciated from the following description of the embodiments, taken in conjunction with the FIGURE which is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Hereinafter, embodiments are described in detail by referring to the attached drawings, and in the drawings, like reference numerals denote like elements, and a redundant explanation thereof will not be provided herein.

1. Condensed Cyclic Compound

A condensed cyclic compound according to an embodiment will be described. The condensed cyclic compound may be represented by Formula (1):

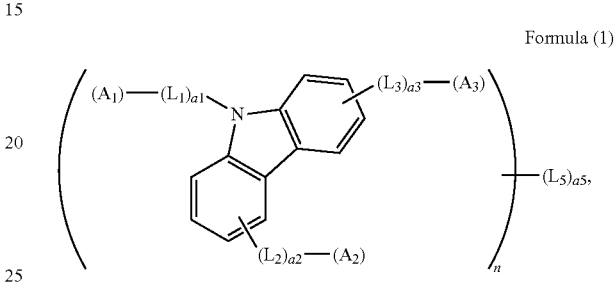

Formula (1)

wherein, in Formula (1), $L_1$ to $L_3$ and $L_5$ may each independently be selected from a single bond, *—C(=O)—*', *—C(=S)—*', *—O—*', *—S—*', *—N(R$_5$)—*' a substituted or unsubstituted $C_2$-$C_{60}$ alkylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,

* and *' each indicate a binding site to a neighboring atom, a1 to a3 and a5 may each independently be an integer selected from 1 to 10, $(L_5)_{a5}$ may be an n-valent linking group or a single bond, wherein n may be a natural number greater than or equal to one, when n is one, $(L_5)_{a5}$ may not exist, when n is a natural number greater than or equal to two, at least one of *-$(L_1)_{a1}$-$(A_1)$, *-$(L_2)_{a2}$-$(A_2)$, and *-$(L_3)_{a3}$-$(A_3)$ may be linked to $(L_5)_{a5}$ or may be a single bond linked to $(L_5)_{a5}$, i) $A_1$ to $A_3$ and $R_5$ may each independently be linked to $(L_5)_{a5}$;

ii) $A_1$ to $A_3$ and $R_5$ may each independently be a single bond linked to $(L_5)_{a5}$;

iii) $A_1$ to $A_3$ and $R_5$ may each independently be a group represented by one of Formulae (2) to (5); or iv) $A_1$ to $A_3$ and $R_5$ may each independently be selected from a substituted or unsubstituted $C_1$-$C_{60}$ alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, the group represented by *-$(L_2)_{a2}$-$(A_2)$ may be linked to the third or fourth carbon of a carbazole core of Formula (1), the group represented by *-$(L_3)_{a3}$-$(A_3)$ may be linked to the fifth or sixth carbon of the carbazole core of Formula (1), and * in the group represented by *-$(L_2)_{a2}$-$(A_2)$ and the group represented by *-$(L_3)_{a3}$-$(A_3)$ indicates a binding site to a carbon atom of the carbazole of Formula (1), and at least one of $A_1$ to $A_3$ may be selected from groups represented by Formulae (2) to (5), provided that, when, i) n is two, ii) $(L_5)_{a5}$ is a single bond, and iii) *-$(L_3)_{a3}$-$(A_3)$ is a single bond linked to $(L_5)_{a5}$, $A_2$ is selected from groups represented by Formulae (2) to (5):

Formula (2)

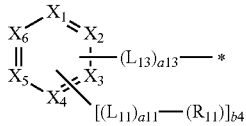

Formula (3)

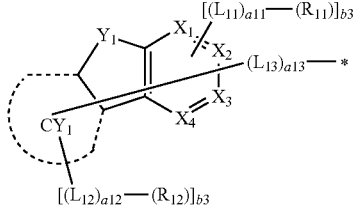

Formula (4)

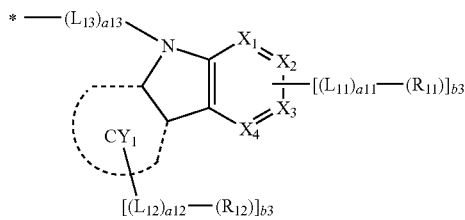

Formula (5)

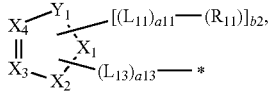

wherein, in Formulae (2) to (5), $X_1$ may be N, carbon linked to *-$(L_{11})_{a11}$-$(R_{11})$, or carbon linked to $L_{13}$, $X_2$ may be N, carbon linked to *-$(L_{11})_{a11}$-$(R_{11})$, or carbon linked to $L_{13}$, $X_3$ may be N, carbon linked to *-$(L_{11})_{a11}$-$(R_{11})$, or carbon linked to $L_{13}$, $X_4$ may be N, carbon linked to *-$(L_{11})_{a11}$-$(R_{11})$, or carbon linked to $L_{13}$, $X_5$ may be N, carbon linked to *-$(L_{11})_{a11}$-$(R_{11})$, or carbon linked to $L_{13}$, and $X_6$ may be N, carbon linked to *-$(L_{11})_{a11}$-$(R_{11})$, or carbon linked to $L_{13}$, provided that $X_1$ to $X_4$ in Formula (4) are not carbon linked to $L_{13}$, $Y_1$ may O, S, N($R_{13}$), or C($R_{14}$)($R_{15}$), and $R_{14}$ and $R_{15}$ may optionally be linked to form a saturated or unsaturated ring, $CY_1$ may be a $C_5$-$C_{30}$ carbocyclic group or a $C_2$-$C_{30}$ heterocyclic group, at least one of $X_1$ to $X_6$ in Formula (2) may be N, in Formulae (3) and (4), at least one $X_1$ to $X_4$ may be N, or $CY_1$ may be a π electron-depleted nitrogen-containing $C_2$-$C_{30}$ heterocyclic group, at least one of $X_1$ to $X_4$ in Formula (5) may be N, $L_{11}$ to $L_{13}$ may each independently be selected from a single bond, a substituted or unsubstituted $C_2$-$C_{60}$ alkylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11 to a13 may each independently be an integer selected from 1 to 10, $R_{11}$ to $R_{15}$ may each independently be selected from hydrogen, deuterium, —F, —Cl, —Br, —I, -$CD_3$, -$CD_2H$, -$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), and —C(=O)($Q_1$), b2 may be an integer selected from 0 to 2, b3 may be an integer selected from 0 to 3, b4 may be an integer selected from 0 to 4, and

* indicates a binding site to a neighboring atom.

The compound represented by Formula (1) may satisfy at least one of conditions (i) and (ii) below:

(i) the group represented by *-$(L_2)_{a2}$-$(A_2)$ in Formula (1) is linked to the third or fourth carbon of the carbazole core of Formula (1), and the group represented by *-$(L_3)_{a3}$-$(A_3)$ is linked to the fifth or sixth carbon of the carbazole core of Formula (1); and (ii) the group represented by *-$(L_1)_{a1}$-$(A_1)$ in Formula (1) is linked to $(L_5)_{a5}$, is a single bond linked to $(L_5)_{a5}$, or does not include a π electron-depleted nitrogen-containing cyclic group.

$L_1$ to $L_3$, $L_5$, and $L_{11}$ to $L_{13}$ in Formulae (1) to (5) may each independently be selected from:

a single bond, *—C(=O)—*', *—C(=S)—*', and *—N($R_5$)—*'; and a phenylene group, an indenylene group, a naphthylene group, an acenaphthylene group, a fluorenylene group, a spiro-bifluorenylene group, a phenanthrenylene group, an anthracenylene group, a fluoranthrenylene group, a triphenylenylene group, a pyrenylene group, a chrysenylene group, a pyrrolylene group, an imidazolylene group, a pyrazolylene group, a triazolylene group, a pyridinylene group, a pyrazinylene group, a pyrimidinylene group, a pyridazinylene group, a triazinylene group, a furanylene group, a thienylene group, an oxazolylene group, an isoxazolylene group, a thiazolylene group, an isothiazolylene group, an oxadiazolylene group, an isoxadiazolylene group, a thiadiazolylene group, an isothiadiazolylene group, a pyranylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoxazolylene group, a benzothiazolylene group, a benzimidazolylene group, an isoindolylene group, an indolylene group, a benzofuranylene group, a benzothiophenylene group, a carbazolylene group, a dibenzofuranylene group, a dibenzothiophenylene group, a benzocarbazolylene group, a naphthobenzofuranylene group, a naphthobenzothiophenylene group, an imidazopyrimidinylene group, and an imidazopyridinylene group, each unsubstituted or substituted with at least one selected from deuterium, —F, -CD$_3$, -CD$_2$H, -CDH$_2$, —CF$_3$, —CF$_2$H, —CFH$_2$, —NCS, a cyano group, a C$_1$-C$_{20}$ alkyl group, a C$_1$-C$_{20}$ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group,

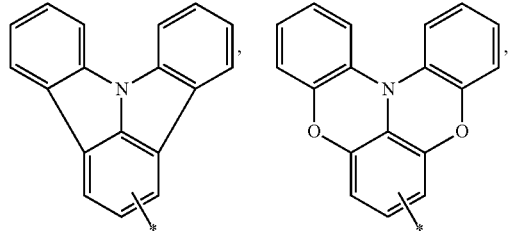

—Si(Q$_{31}$)(Q$_{32}$)(Q$_{33}$), —N(Q$_{31}$)(Q$_{32}$), and —C(=O)(Q$_{31}$), provided that L$_{11}$ to L$_{13}$ are not *—C(=O)—*', *—C(=S)—*', and *—N(R$_5$)—*'.

For example, L$_1$ to L$_3$ in Formula (1) may each independently be selected from:

a single bond; and a phenylene group, an indenylene group, a naphthylene group, an acenaphthylene group, a fluorenylene group, a spiro-bifluorenylene group, a phenanthrenylene group, an anthracenylene group, a fluoranthrenylene group, a triphenylenylene group, a pyrenylene group, a chrysenylene group, a pyrrolylene group, a furanylene group, a thienylene group, an isoindolylene group, an indolylene group, a benzofuranylene group, a benzothiophenylene group, a carbazolylene group, a dibenzofuranylene group, a dibenzothiophenylene group, a benzocarbazolylene group, a naphthobenzofuranylene group, and a naphthobenzothiophenylene group, each unsubstituted or substituted with at least one selected from deuterium, -CD$_3$, -CD$_2$H, -CDH$_2$, a C$_1$-C$_{20}$ alkyl group, a C$_1$-C$_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group,

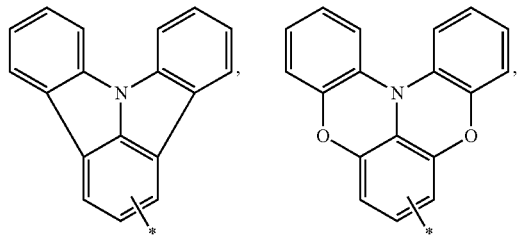

—Si(Q$_{31}$)(Q$_{32}$)(Q$_{33}$), —N(Q$_{31}$)(Q$_{32}$), and —C(=O)(Q$_{31}$), L$_5$ in Formula (1) may be selected from:

a single bond, *—C(=O)—*', *—C(=S)—*', and *—N(R$_5$)—*'; and, a phenylene group, an indenylene group, a naphthylene group, an acenaphthylene group, a fluorenylene group, a spiro-bifluorenylene group, a phenanthrenylene group, an anthracenylene group, a fluoranthrenylene group, a triphenylenylene group, a pyrenylene group, a chrysenylene group, a pyrrolylene group, an imidazolylene group, a pyrazolylene group, a triazolylene group, a pyridinylene group, a pyrazinylene group, a pyrimidinylene group, a pyridazinylene group, a triazinylene group, a furanylene group, a thienylene group, an oxazolylene group, an isoxazolylene group, a thiazolylene group, an isothiazolylene group, an oxadiazolylene group, an isoxadiazolylene group, a thiadiazolylene group, an isothiadiazolylene group, a pyrenylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoxazolylene group, a benzothiazolylene group, a benzimidazolylene group, an isoindolylene group, an indolylene group, a benzofuranylene group, a benzothiophenylene group, a carbazolylene group, a dibenzofuranylene group, a dibenzothiophenylene group, a benzocarbazolylene group, a naphthobenzofuranylene group, a naphthobenzothiophenylene group, an imidazopyrimidinylene group, and an imidazopyridinylene group, each unsubstituted or substituted with at least one selected from deuterium, —F, -CD$_3$, -CD$_2$H, -CDH$_2$, —CF$_3$, —CF$_2$H, —CFH$_2$, —NCS, a cyano group, a C$_1$-C$_{20}$ alkyl group, a C$_1$-C$_{20}$ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group,

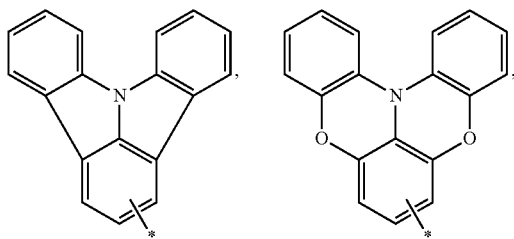

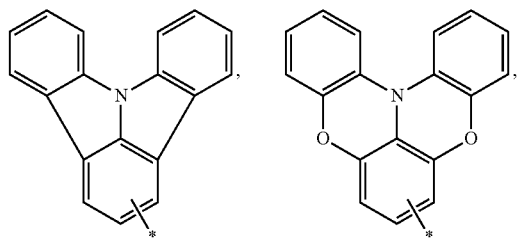

—Si($Q_{31}$)($Q_{32}$)($Q_{33}$), —N($Q_{31}$)($Q_{32}$), and —C(=O)($Q_{31}$), and $L_{11}$ to $L_{13}$ in Formulae (2) to (5) may each independently be selected from a phenylene group, an indenylene group, a naphthylene group, an acenaphthylene group, a fluorenylene group, a spiro-bifluorenylene group, a phenanthrenylene group, an anthracenylene group, a fluoranthrenylene group, a triphenylenylene group, a pyrenylene group, a chrysenylene group, a pyrrolylene group, an imidazolylene group, a pyrazolylene group, a triazolylene group, a pyridinylene group, a pyrazinylene group, a pyrimidinylene group, a pyridazinylene group, a triazinylene group, a furanylene group, a thienylene group, an oxazolylene group, an isoxazolylene group, a thiazolylene group, an isothiazolylene group, an oxadiazolylene group, an isoxadiazolylene group, a thiadiazolylene group, an isothiadiazolylene group, a pyranylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoxazolylene group, a benzothiazolylene group, a benzimidazolylene group, an isoindolylene group, an indolylene group, a benzofuranylene group, a benzothiophenylene group, a carbazolylene group, a dibenzofuranylene group, a dibenzothiophenylene group, a benzocarbazolylene group, a naphthobenzofuranylene group, a naphthobenzothiophenylene group, an imidazopyrimidinylene group, and an imidazopyridinylene group, each unsubstituted or substituted with at least one selected from deuterium, —F, -CD$_3$, -CD$_2$H, -CDH$_2$, —CF$_3$, —CF$_2$H, —CFH$_2$, —NCS, a cyano group, a $C_1$-$C_{20}$ alkyl group, a $C_1$-$C_{20}$ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group, —Si($Q_{31}$)($Q_{32}$)($Q_{33}$), —N($Q_{31}$)($Q_{32}$), and —C(=O)($Q_{31}$), but embodiments of the present disclosure are not limited thereto.

In one or more embodiments, $L_1$ to $L_3$ in Formula (1) may each independently be selected from a single bond, groups represented by Formulae 6-1 to 6-3, and groups represented by Formulae 6-20 to 6-27, $L_5$ in Formula (1) may be selected from a single bond, *—C(=O)—*', *—C(=S)—*', *—N(R$_5$)—*', and groups represented by Formulae 6-1 to 6-27, and $L_{11}$ to $L_{13}$ in Formulae (2) to (5) may each independently be selected from a single bond and groups represented by Formulae 6-1 to 6-27, but embodiments of the present disclosure are not limited thereto:

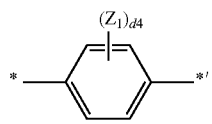

Formula 6-1

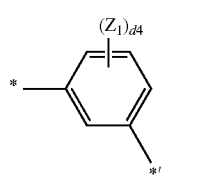

Formula 6-2

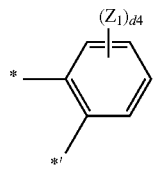

Formula 6-3

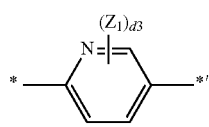

Formula 6-4

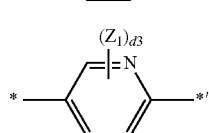

Formula 6-5

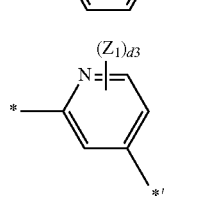

Formula 6-6

Formula 6-7 through Formula 6-23

-continued

Formula 6-24
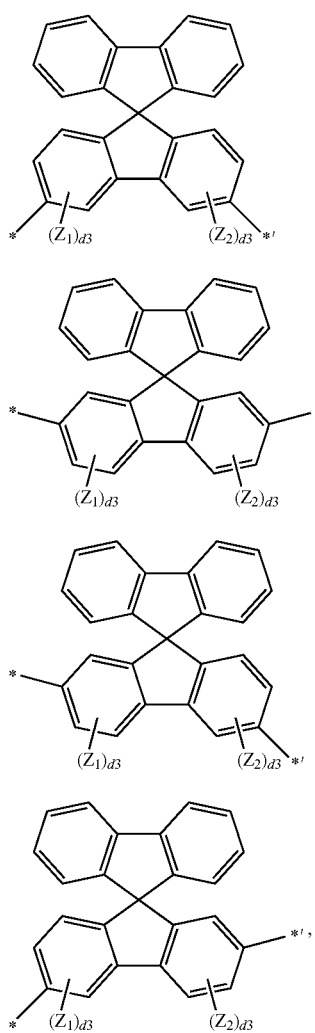

Formula 6-25

Formula 6-26

Formula 6-27 wherein, in Formulae 6-1 to 6-27, $Y_2$ may be O, S, $C(Z_3)(Z_4)$, or $N(Z_5)$, $Z_1$ to $Z_5$ may each independently be hydrogen, deuterium, $-CD_3$, $-CD_2H$, $-CDH_2$, a $C_1$-$C_{20}$ alkyl group, a $C_1$-$C_{20}$ alkoxy group, a phenyl group, a biphenyl group, a trimethylsilyl group, or a triphenylsilyl group, d2 may be 1 or 2, d3 may be 1, 2, or 3, d4 may be 1, 2, 3, or 4, and

* and *' each indicate a binding site to a neighboring atom.

In one or more embodiments, $L_1$ to $L_3$ in Formula (1) may each independently be selected from a single bond and a group represented by Formula 6(1), $L_5$ in Formula (1) may be selected from a single bond, *—C(=O)—*', *—C(=S)—*', *—N($R_5$)—*', and groups represented by Formulae 6(1) to 6(10), $L_{11}$ to $L_{13}$ in Formulae (2) to (5) may each independently be selected from a single bond and groups represented by Formulae 6(1) to 6(9), but embodiments of the present disclosure are not limited thereto:

Formula 6(1)
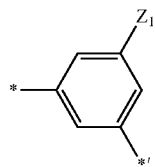

Formula 6(2)
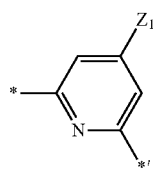

Formula 6(3)
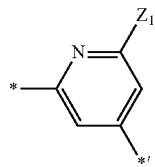

Formula 6(4)
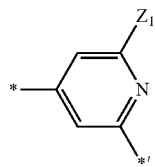

Formula 6(5)
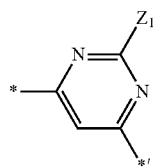

Formula 6(6)
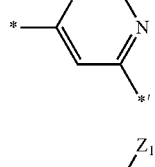

Formula 6(7)
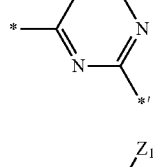

Formula 6(8)
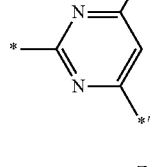

Formula 6(9)
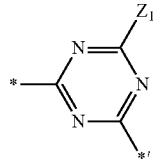

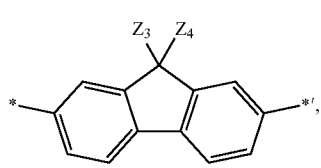

Formula 6(10)

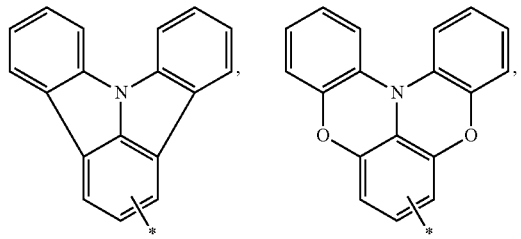

wherein $Z_1$, $Z_3$, and $Z_5$ in Formulae 6(1) to 6(10) may each independently be hydrogen, deuterium, -CD$_3$, -CD$_2$H, -CDH$_2$, a $C_1$-$C_{20}$ alkyl group, a $C_1$-$C_{20}$ alkoxy group, a phenyl group, a biphenyl group, a trimethylsilyl group, or a triphenylsilyl group, and * and *' each indicate a binding site to a neighboring atom.

a1, a2, a3, a5, a11, a12, and a13 in Formulae (1) to (5) respectively indicate the number of groups $L_1$, the number of groups $L_2$, the number of groups $L_3$, the number of groups $L_5$, the number of groups $L_{11}$, the number of groups $L_{12}$, and the number of groups $L_{13}$ and may each independently be selected from an integer from 1 to 5 or an integer from 1 to 3, but embodiments of the present disclosure are not limited thereto. When a1 is two or more, two or more groups $L_1$ may be identical to or different from each other. This may be equally applied to each of a2 to a3, a5, and a11 to a13 and each of $L_2$ to $L_3$, $L_5$, and $L_{11}$ to $L_{13}$.

n may be a natural number from 1 to 10. For example, n may be 1, 2, 3, or 4, or may be 1 or 2, but embodiments of the present disclosure are not limited thereto.

In one or more embodiments, in Formula (1), 1) n may be one, or 2) n may be two and $(L_5)_{a5}$ may be a group represented by *—Ar$_1$-T$_1$-Ar$_2$—*', and Ar$_1$, T$_1$, and Ar$_2$ are the same as described in connection with $L_5$, provided that Ar$_1$ and Ar$_2$ are not a single bond, *—C(=O)—*', *—C(=S)—*', *—O—*', *—S—*', or *—N(R$_5$)—*' but embodiments of the present disclosure are not limited thereto.

In one or more embodiments, i) $A_1$ to $A_3$ and $R_5$ in Formula (1) may each independently be linked to $(L_5)_{a5}$;

ii) $A_1$ to $A_3$ and $R_5$ in Formula (1) may each independently be a single bond linked to $(L_5)_{a5}$;

iii) $A_1$ to $A_3$ and $R_5$ in Formula (1) may each independently be a group represented by one of Formulae (2) to (5); or iv) $A_1$ to $A_3$ and $R_5$ in Formula (1) may each independently be selected from a phenyl group, an indenyl group, a naphthyl group, an acenaphthyl group, a fluorenyl group, a spiro-bifluorenyl group, a phenanthrenyl group, an anthracenyl group, a fluoranthenyl group, a triphenylenyl group, a pyrenyl group, a chrysenyl group, a pyrrolyl group, a furanyl group, a thienyl group, an isoindolyl group, an indolyl group, a benzofuranyl group, a benzothiophenyl group, a carbazolyl group, a dibenzofuranyl group, a dibenzothiophenyl group, a benzocarbazolyl group, a naphthobenzofuranyl group, and a naphthobenzothiophenyl group, each unsubstituted or substituted with at least one selected from deuterium, -CD$_3$, -CD$_2$H, -CDH$_2$, a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group, —Si(Q$_{31}$)(Q$_{32}$)(Q$_{33}$), —N(Q$_{31}$)(Q$_{32}$), and —C(=O)(Q$_{31}$), and $R_{11}$ to $R_{15}$ in Formulae (2) to (5) may each independently be selected from:

hydrogen, deuterium, —F, -CD$_3$, -CD$_2$H, -CDH$_2$, —CF$_3$, —CF$_2$H, —CFH$_2$, —NCS, a cyano group, a $C_1$-$C_{20}$ alkyl group, and $C_1$-$C_{20}$ alkoxy group; and a phenyl group, an indenyl group, a naphthyl group, an acenaphthyl group, a fluorenyl group, a spiro-bifluorenyl group, a phenanthrenyl group, an anthracenyl group, a fluoranthenyl group, a triphenylenyl group, a pyrenyl group, a chrysenyl group, a pyrrolyl group, an imidazolyl group, a pyrazolyl group, a triazolyl group, a pyridinyl group, a pyrazinyl group, a pyrimidinyl group, a pyridazinyl group, a triazinyl group, a furanyl group, a thienyl group, an oxazolyl group, an isoxazolyl group, a thiazolyl group, an isothiazolyl group, an oxadiazolyl group, an isoxadiazolyl group, a thiadiazolyl group, an isothiadiazolyl group, a pyranyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzothiazolyl group, a benzimidazolyl group, an isoindolyl group, an indolyl group, a benzofuranyl group, a benzothiophenyl group, a carbazolyl group, a dibenzofuranyl group, a dibenzothiophenyl group, a benzocarbazolyl group, a naphthobenzofuranyl group, a naphthobenzothiophenyl group, an imidazopyrimidinyl group, and an imidazopyridinyl group, each unsubstituted or substituted with at least one selected from deuterium, —F, -CD$_3$, -CD$_2$H, -CDH$_2$, —CF$_3$, —CF$_2$H, —CFH$_2$, —NCS, a cyano group, a $C_1$-$C_{20}$ alkyl group, a $C_1$-$C_{20}$ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group,

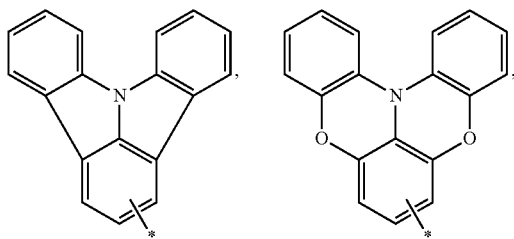

—Si($Q_{31}$)($Q_{32}$)($Q_{33}$), —N($Q_{31}$)($Q_{32}$), and —C(=O)($Q_{31}$), but embodiments of the present disclosure are not limited thereto.

At least one of $A_1$ to $A_3$ may be selected from groups represented by Formulae (2) to (5), provided that, when i) n is two, ii) $(L_5)_{a5}$ is a single bond, and iii) *-$(L_3)_{a3}$-($A_3$) is a single bond linked to $(L_5)_{a5}$, $A_2$ is selected from groups represented by Formulae (2) to (5).

For example, $A_2$ in Formula (1) may be a group represented by one of Formulae (2) to (5), and none, one, or two of $A_1$ and $A_3$ may each independently be a group represented by one of Formulae (2) to (5).

In one or more embodiments, in Formula (1), $A_2$ may be a group represented by one of Formulae (2) to (5), and $A_1$ and $A_3$ may not be groups represented by Formulae (2) to (5).

In one or more embodiments, in Formula (1), $A_1$ and $A_2$ may each independently be a group represented by one of Formulae (2) to (5), and $A_3$ may not be groups represented by Formulae (2) to (5).

In one or more embodiments, in Formula (1), $A_2$ and $A_3$ may each independently be a group represented by one of Formulae (2) to (5), and $A_1$ may not be groups represented by Formulae (2) to (5).

In one or more embodiments, in Formula (1), $A_1$ to $A_3$ may each independently be a group represented by one of Formulae (2) to (5).

In one or more embodiments, $CY_1$ in Formulae (3) and (4) may be a 6-membered cyclic group. For example, $CY_1$ may be a benzene group, a pyridine group, a pyrimidine group, a pyrazine group, or a pyridazine group, but embodiments of the present disclosure are not limited thereto.

In one or more embodiments, the group represented by Formula (2) may be selected from groups represented by Formulae (2)-1 to (2)-7:

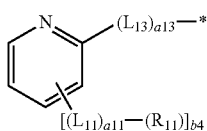

Formula (2)-1

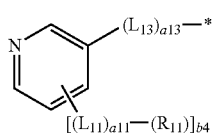

Formula (2)-2

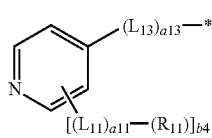

Formula (2)-3

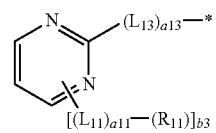

Formula (2)-4

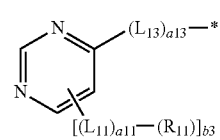

Formula (2)-5

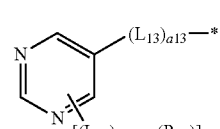

Formula (2)-6

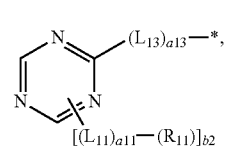

Formula (2)-7 wherein, in Formulae (2)-1 to (2)-7, $L_{11}$, $L_{13}$, a11, a13, $R_{11}$, and $(L_{11})_{a11}$-$(R_{11})$ are each independently the same as described above, b4 may be an integer selected from 0 to 4, b3 may be an integer selected from 0 to 3, b2 may be an integer selected from 0 to 2, and * indicates a binding site to a neighboring atom.

In one or more embodiments, the group represented by Formula (2) may be selected from groups represented by Formulae (2)-A to (2)-F:

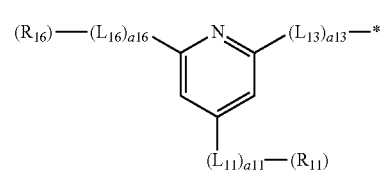

Formula (2)-A

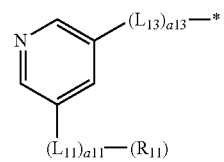

Formula (2)-B

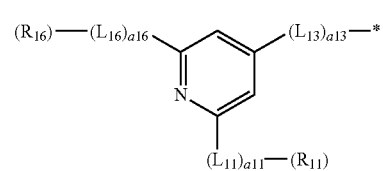

Formula (2)-C

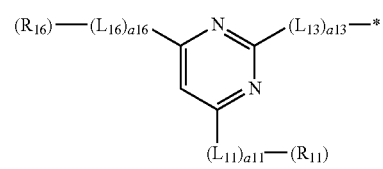

Formula (2)-D

Formula (2)-E

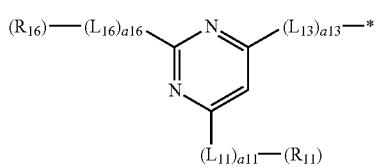

Formula (2)-F

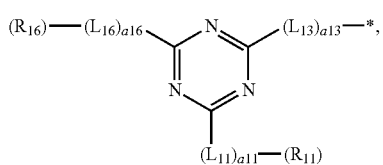

wherein, in Formulae (2)-A to (2)-F, $L_{11}$, $L_{13}$, a11, a13, $R_{11}$, and $(L_{11})_{a11}$-$(R_{11})$ are each independently the same as described above, $L_{16}$, a16, $R_{16}$, and $(L_{16})_{a16}$-$(R_{16})$ are each independently the same as described in connection with $L_{11}$, a11, $R_{11}$, and $(L_{11})_{a11}$-$(R_{11})$, and * indicates a binding site to a neighboring atom.

In one or more embodiments, a core represented by

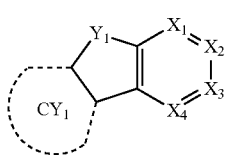

in Formula (3) may be selected from groups represented by Formulae 3-1 to 3-20, a core represented by

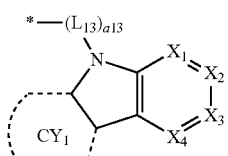

in Formula (4) may be selected from groups represented by Formulae 4-1 to 4-10, and a core represented by

in Formula (5) may be selected from groups represented by Formulae 5-1 to 5-6:

3-1

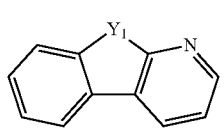

3-2

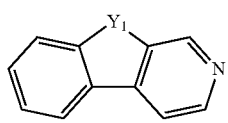

3-3

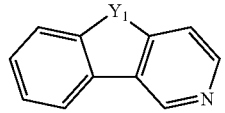

3-4

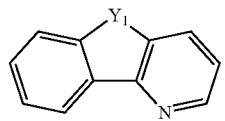

3-5

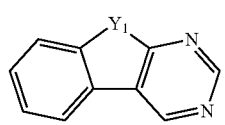

3-6

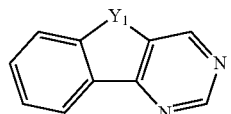

3-7

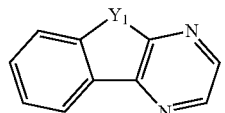

3-8

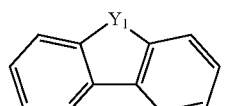

3-9

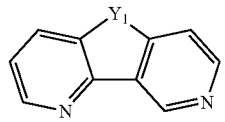

3-10

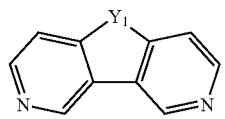

3-11

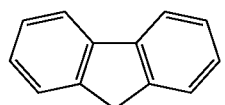

3-12

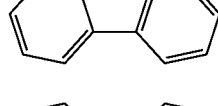

3-13 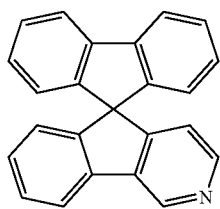
3-14 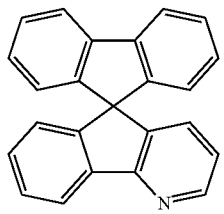
3-15 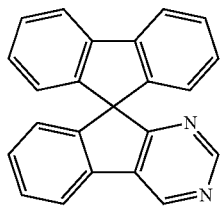
3-16 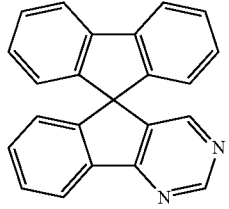
3-17 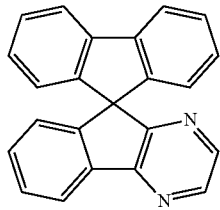
3-18 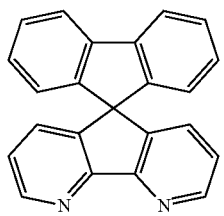
3-19 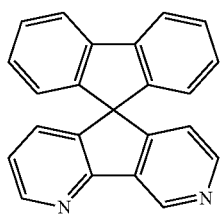
3-20 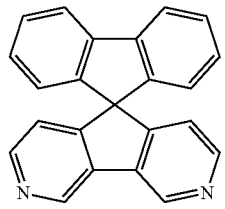
4-1 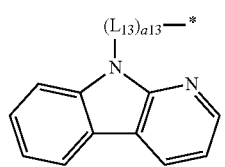
4-2 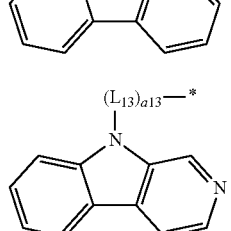
4-3 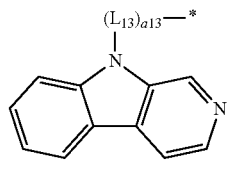
4-4 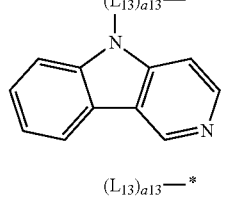
4-5 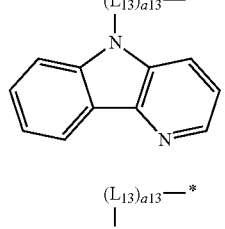
4-6 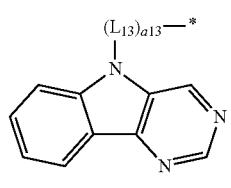
4-7 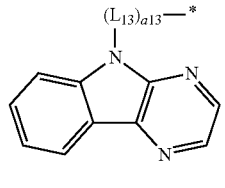
4-8

4-9

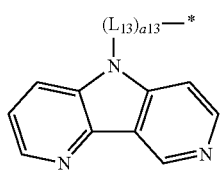

4-10

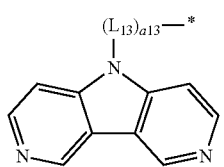

5-1

5-2

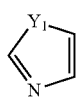

5-3

5-4

5-5

5-6

wherein $Y_1$ in Formulae 3-1 to 3-20, 4-1 to 4-10, and 5-1 to 5-6 are the same as described above.

In one or more embodiments, the group represented by Formula (3) may be selected from groups represented by Formulae (3)-1 to (3)-11, and the group represented by Formula (4) may be selected from groups represented by Formulae (4)-1 and (4)-2, but embodiments of the present disclosure are not limited thereto:

Formula (3)-1

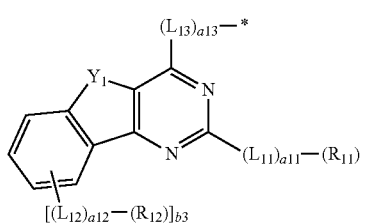

Formula (3)-2

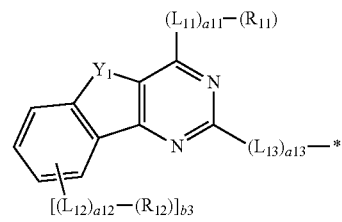

Formula (3)-3

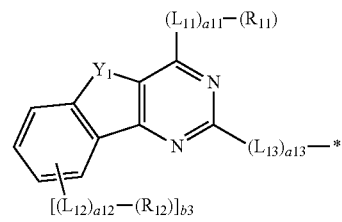

Formula (3)-4

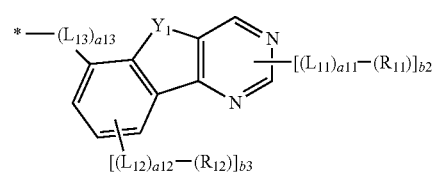

Formula (3)-5

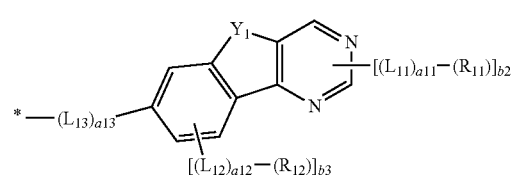

Formula (3)-6

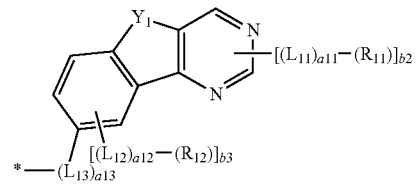

Formula (3)-7

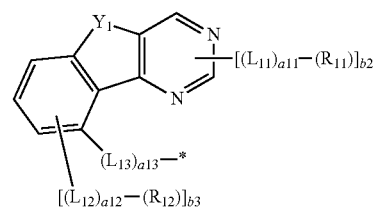

Formula (3)-8

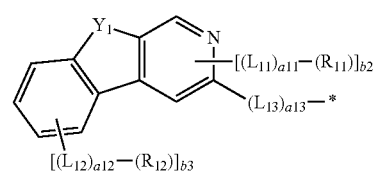

Formula (3)-9

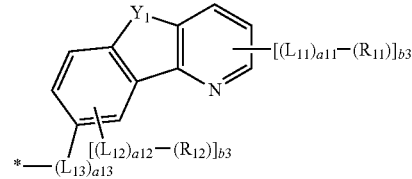

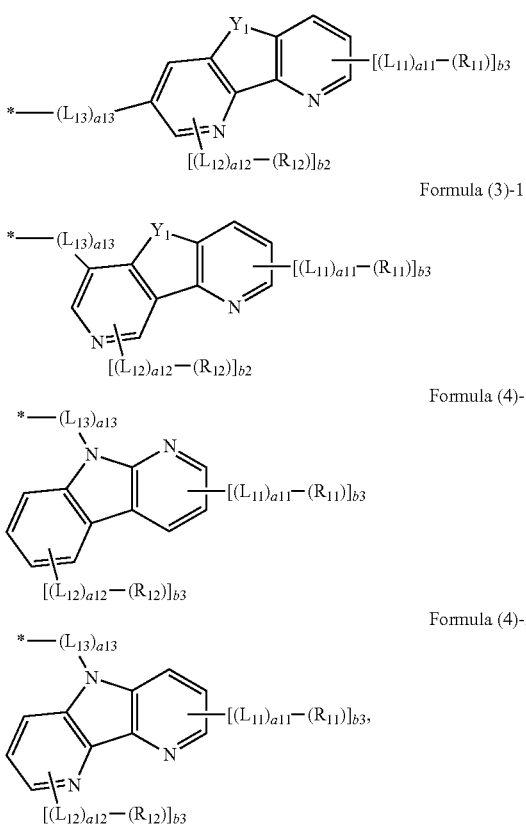

wherein, in Formulae (3)-1 to (3)-11, (4)-1, and (4)-2, $L_{11}$ to $L_{13}$, a11 to a13, $R_{11}$, $R_{12}$, and $Y_1$ are each independently the same as described above, b2 may be an integer selected from 0 to 2, b3 may be an integer selected from 0 to 3, and * indicates a binding site to a neighboring atom.

In one or more embodiments, in Formula (1), $A_1$ to $A_3$, which are not groups represented by Formulae (2) to (5), may not include a π electron-depleted nitrogen-containing cyclic group.

Accordingly, four embodiments may be provided as follows:

First Embodiment $A_2$ in Formula (1) may be selected from groups represented by Formulae (2) to (5),
  i) the groups represented by *-$(L_1)_{a1}$-$(A_1)$ and *-$(L_3)_{a3}$-$(A_3)$ in Formula (1) may each independently be linked to $(L_5)_{a5}$ or may be a single bond linked to $(L_5)_{a5}$, or
  ii) in *-$(L_1)_{a1}$-$(A_1)$ and *-$(L_3)_{a3}$-$(A_3)$ of Formula (1),
  $L_1$ and $L_3$ may each independently be a single bond, or may each independently be selected from a phenylene group, a fluorenylene group, a spiro-bifluorenylene group, a carbazolylene group, a dibenzofuranylene group, and a dibenzothiophenylene group, each unsubstituted or substituted with at least one selected from deuterium, -$CD_3$, -$CD_2H$, -$CDH_2$, a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group, —$Si(Q_{31})(Q_{32})(Q_{33})$, —$N(Q_{31})(Q_{32})$, and —$C(=O)(Q_{31})$,
  a1 and a3 may each independently be 1, 2, or 3, and
  $A_1$ and $A_3$ may each independently be selected from a phenyl group, a fluorenyl group, a spiro-bifluorenyl group, a carbazolyl group, a dibenzofuranyl group, and a dibenzothiophenyl group, each unsubstituted or substituted with at least one selected from deuterium, -$CD_3$, -$CD_2H$, -$CDH_2$, a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group, —$Si(Q_{31})(Q_{32})(Q_{33})$, —$N(Q_{31})(Q_{32})$, and —$C(=O)(Q_{31})$.

Second Embodiment $A_1$ and $A_2$ in Formula (1) may each independently be selected from groups represented by Formulae (2) to (5),
  i) the group represented by *-$(L_3)_{a3}$-$(A_3)$ in Formula (1) may be linked to $(L_5)_{a5}$ or may be a single bond linked to $(L_5)_{a5}$, or
  ii) in *-$(L_3)_{a3}$-$(A_3)$ of Formula (1),
  $L_3$ may be a single bond, or may be selected from a phenylene group, a fluorenylene group, a spiro-bifluorenylene group, a carbazolylene group, a dibenzofuranylene group, and a dibenzothiophenylene group, each unsubstituted or substituted with at least one selected from deuterium, -$CD_3$, -$CD_2H$, -$CDH_2$, a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group, —$Si(Q_{31})(Q_{32})(Q_{33})$, —$N(Q_{31})(Q_{32})$, and —$C(=O)(Q_{31})$,
  a3 may be 1, 2, or 3, and
  $A_3$ may be selected from a phenyl group, a fluorenyl group, a spiro-bifluorenyl group, a carbazolyl group, a dibenzofuranyl group, and a dibenzothiophenyl group, each unsubstituted or substituted with at least one selected from deuterium, -$CD_3$, -$CD_2H$, -$CDH_2$, a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group, —$Si(Q_{31})(Q_{32})(Q_{33})$, —$N(Q_{31})(Q_{32})$, and —$C(=O)(Q_{31})$.

Third Embodiment $A_2$ and $A_3$ in Formula (1) may each independently be selected from groups represented by Formulae (2) to (5),
  i) the group represented by *-$(L_1)_{a1}$-$(A_1)$ in Formula (1) may be linked to $(L_5)_{a5}$ or may be a single bond linked to $(L_5)_{a5}$, or
  ii) in *-$(L_1)_{a1}$-$(A_1)$ of Formula (1),
  $L_1$ may be a single bond, or may be selected from a phenylene group, a fluorenylene group, a spiro-bifluorenylene group, a carbazolylene group, a dibenzofuranylene group, and a dibenzothiophenylene group, each unsubstituted or substituted with at least one selected from deuterium, -CD$_3$, -CD$_2$H, -CDH$_2$, a C$_1$-C$_{20}$ alkyl group, a C$_1$-C$_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group, —Si(Q$_{31}$)(Q$_{32}$)(Q$_{33}$), —N(Q$_{31}$)(Q$_{32}$), and —C(=O)(Q$_{31}$), a1 may be 1, 2, or 3, A$_1$ may be selected from a phenyl group, a fluorenyl group, a spiro-bifluorenyl group, a carbazolyl group, a dibenzofuranyl group, and a dibenzothiophenyl group, each unsubstituted or substituted with at least one selected from deuterium, -CD$_3$, -CD$_2$H, -CDH$_2$, a C$_1$-C$_{20}$ alkyl group, a C$_1$-C$_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group, —Si(Q$_{31}$)(Q$_{32}$)(Q$_{33}$), —N(Q$_{31}$)(Q$_{32}$), and —C(=O)(Q$_{31}$).

Fourth Embodiment

A$_1$ to A$_3$ in Formula (1) may each independently be selected from groups represented by Formulae (2) to (5).

In one or more embodiments, in Formula (1),

1) A$_2$ may be selected from groups represented by Formulae (2) to (5), and i) the groups represented by *-(L$_1$)$_{a1}$-(A$_1$) and *-(L$_3$)$_{a3}$-(A$_3$) may each independently be linked to (L$_5$)$_{a5}$; ii) the groups represented by *-(L$_1$)$_{a1}$-(A$_1$) and *-(L$_3$)$_{a3}$-(A$_3$) may each independently be a single bond linked to (L$_5$)$_{a5}$; or iii) the groups represented by *-(L$_1$)$_{a1}$-(A$_1$) and *-(L$_3$)$_{a3}$-(A$_3$) may each independently be selected from groups represented by Formulae 7-1 to 7-29, 2) A$_1$ and A$_2$ may each independently be selected from groups represented by Formulae (2) to (5), and i) the group represented by *-(L$_3$)$_{a3}$-(A$_3$) may be linked to (L$_5$)$_{a5}$; ii) the group represented by *-(L$_3$)$_{a3}$-(A$_3$) may be a single bond linked to (L$_5$)$_{a5}$; or iii) the group represented by *-(L$_3$)$_{a3}$-(A$_3$) may be selected from groups represented by Formulae 7-1 to 7-29, 3) A$_2$ and A$_3$ may each independently be selected from groups represented by Formulae (2) to (5), and i) the group represented by *-(L$_1$)$_{a1}$-(A$_1$) may be linked to (L$_5$)$_{a5}$; ii) the group represented by *-(L$_1$)$_{a1}$-(A$_1$) may be a single bond linked to (L$_5$)$_{a5}$; or iii) the group represented by *-(L$_1$)$_{a1}$-(A$_1$) may be selected from groups represented by Formulae 7-1 to 7-29, or 4) A$_1$ to A$_3$ may each independently be selected from groups represented by Formulae (2) to (5), and the groups represented by *-(L$_{11}$)$_{a11}$-(R$_{11}$) and *-(L$_{12}$)$_{a12}$-(R$_{12}$) in Formulae (2) to (5) may each independently be selected from groups represented by Formulae 7-1 to 7-57, but embodiments of the present disclosure are not limited thereto:

7-1

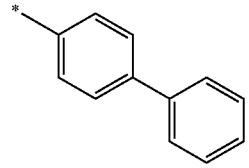

7-2

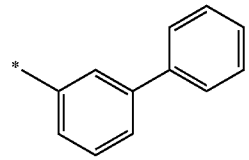

7-3

7-4

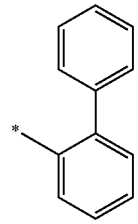

7-5

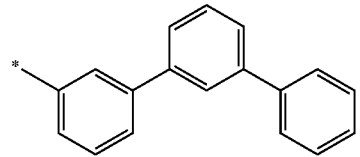

7-6

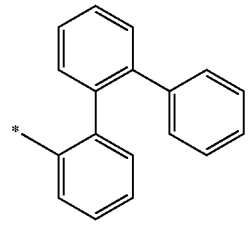

7-7

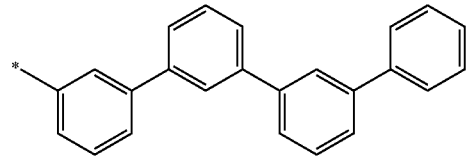

7-8

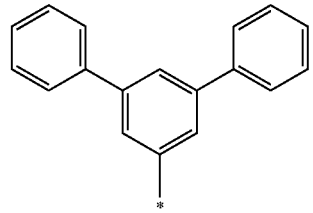

-continued
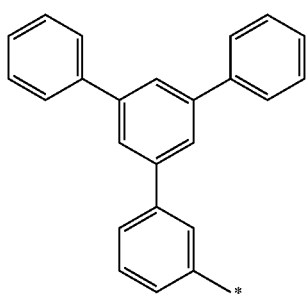
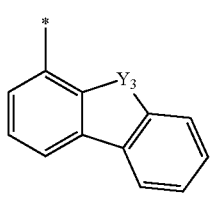
7-10
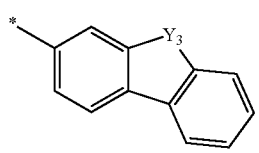
7-11
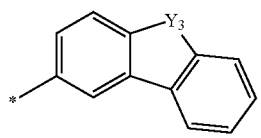
7-12
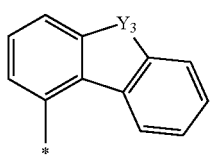
7-13
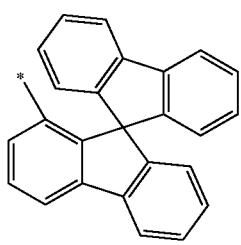
7-14
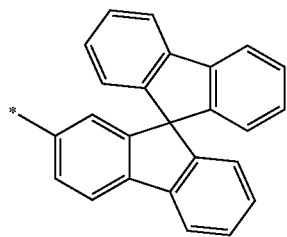
7-15
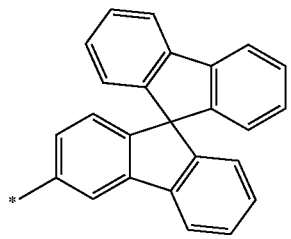
7-16
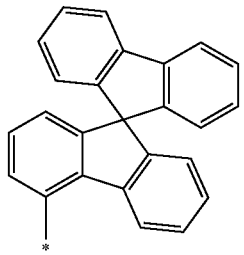
7-17
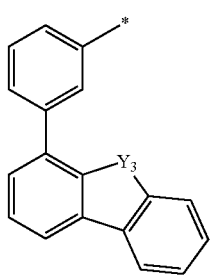
7-18
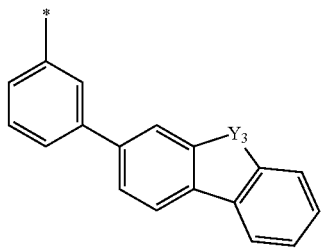
7-19
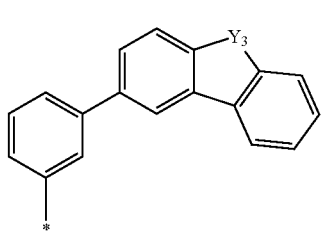
7-20
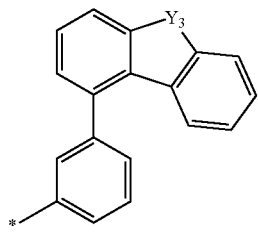
7-21

7-22 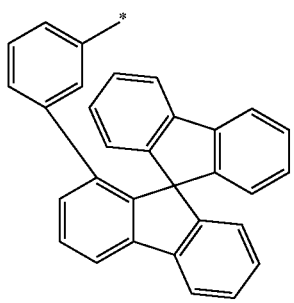
7-23 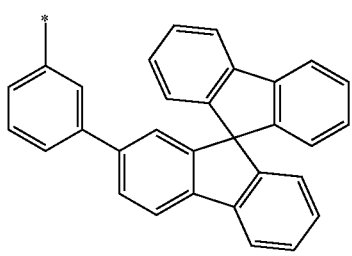
7-24 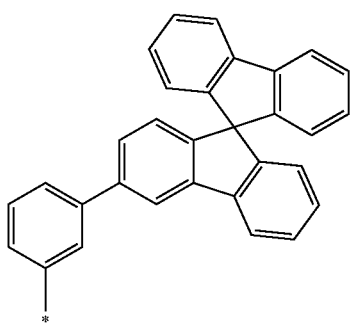
7-25 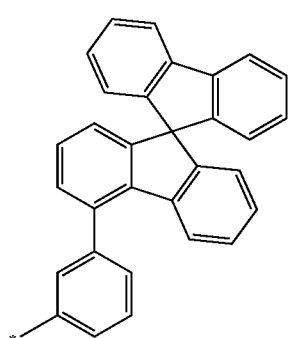
7-26 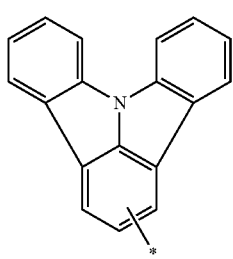
7-27 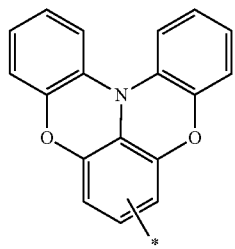
7-28 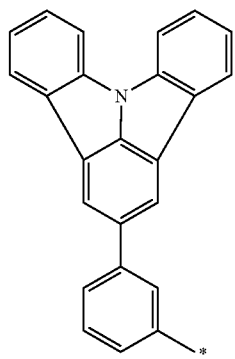
7-29 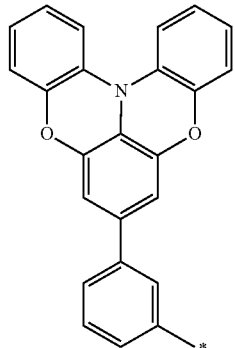
7-30 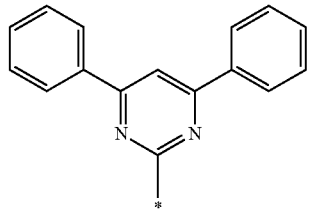
7-31

7-32 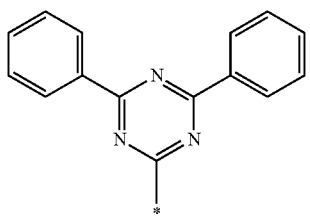
7-33 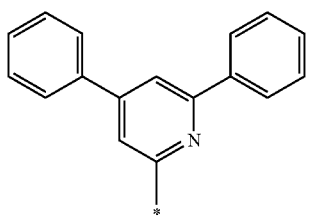
7-34 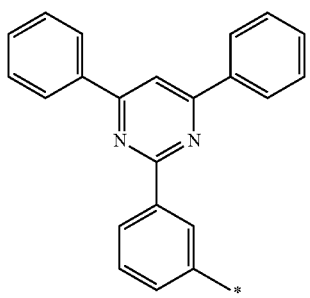
7-35 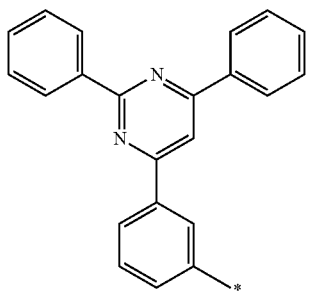
7-36 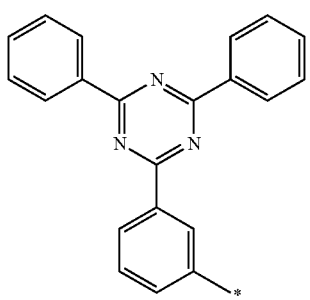
7-37 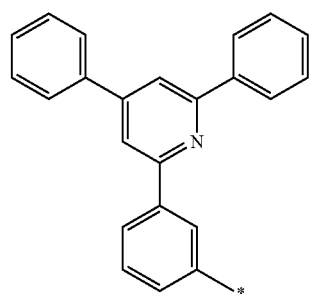
7-38 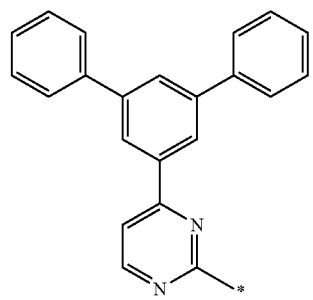
7-39 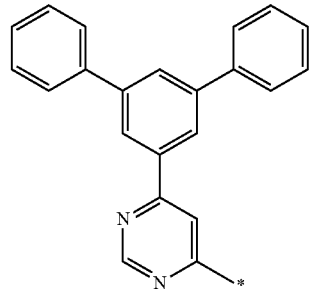
7-40 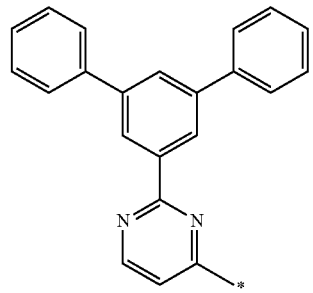
7-41 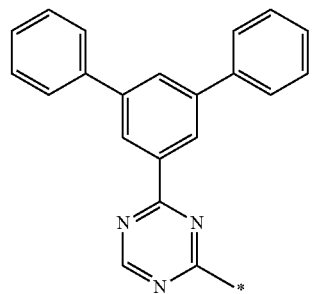

7-42 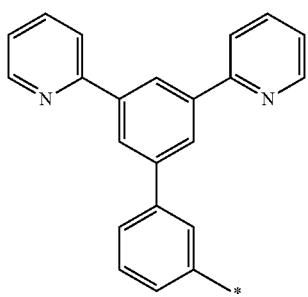
7-43 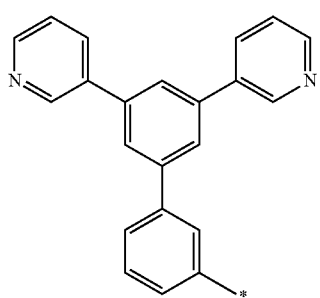
7-44 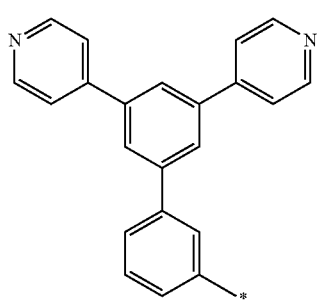
7-45 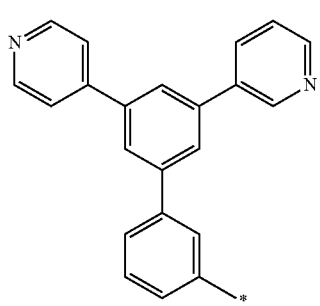
7-46 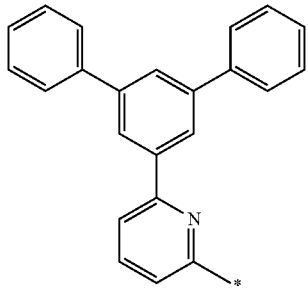
7-47 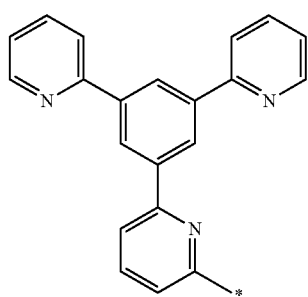
7-48 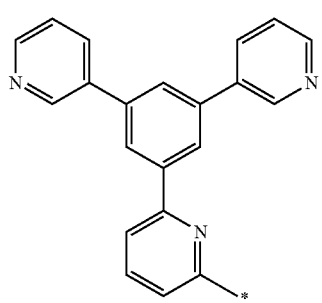
7-49 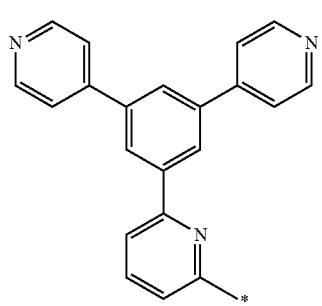
7-50 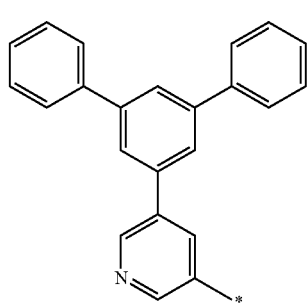
7-51 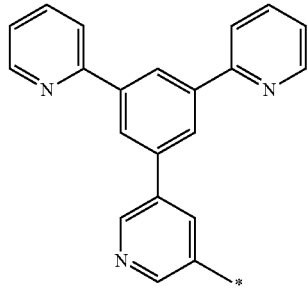

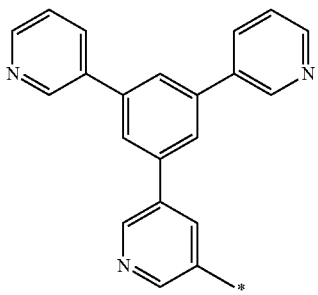

7-52

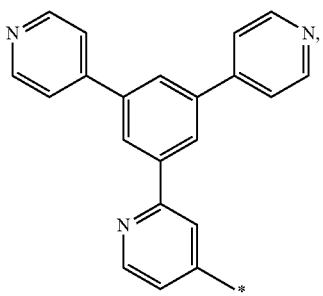

7-53

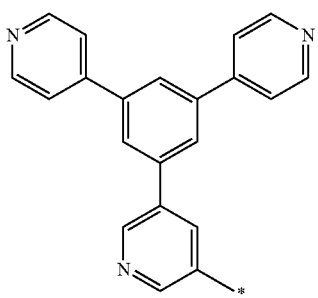

7-54

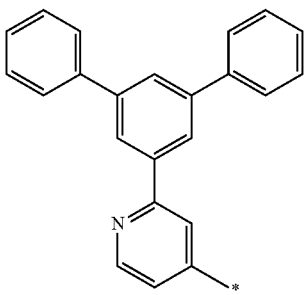

7-55

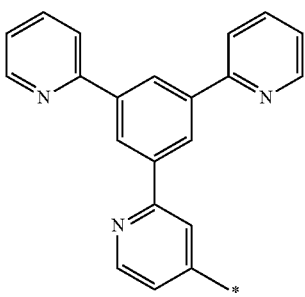

7-56

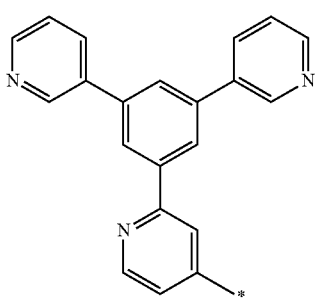

7-57 wherein, in Formulae 7-1 to 7-57, $Y_3$ may be O, S, $C(Z_{13})(Z_{14})$, or $N(Z_{15})$, $Z_{13}$ to $Z_{15}$ may each independently be selected from -$CD_3$, -$CD_2H$, -$CDH_2$, a $C_1$-$C_{20}$ alkyl group, a $C_1$-$C_{20}$ alkoxy group, a phenyl group, and a biphenyl group, and * indicates a binding site to a neighboring atom.

The group represented by *-$(L_2)_{a2}$-$(A_2)$ and the group represented by *-$(L_3)_{a3}$-$(A_3)$ in Formula (1) may be linked to the carbazole core, such that a linking position of the group represented by *-$(L_2)_{a2}$-$(A_2)$ and the carbazole core is asymmetric to a linking position of the group represented by *-$(L_3)_{a3}$-$(A_3)$ and the carbazole core with respect to a reverse central axis passing through a nitrogen atom of the carbazole core of Formula (1).

When b2 to b4 in Formulae (2) to (5), (2)-1 to (2)-7, (3)-1 to (3)-11, (4)-1, and (4)-2 are each two or more, two or more groups *-$(L_{11})_{a11}$-$(R_{11})$ may be identical to or different from each other and two or more groups *-$(L_{12})_{a12}$-$(R_{12})$ may be identical to or different from each other. Also, two or more neighboring groups selected from groups $R_{11}$ and/or two or more neighboring groups selected from groups $R_{12}$ may optionally be linked to form a $C_2$-$C_{10}$ carbocyclic group or a $C_2$-$C_{10}$ heterocyclic group, but embodiments of the present disclosure are not limited thereto.

The term "hydrogen atom" as used herein is a concept encompassing "deuterium atom" even when there is no special parallel representation of "deuterium atom", and each existing hydrogen atom may be an arbitrary number of deuterium atoms.

The condensed cyclic compound represented by Formulae (1) has excellent thermal stability due to a relatively high glass transition temperature. Thus, an organic light-emitting device including the condensed cyclic compound is relatively stable with respect to driving heat. Also, since degradation and deformation to the condensed cyclic compound caused by the driving heat of the organic light-emitting device are suppressed, the light emitting lifespan of the organic light-emitting device including the condensed cyclic compound may be improved.

Also, the condensed cyclic compound represented by Formula (1) may have, due to inclusion of azine-containing groups represented by Formulae (2) to (5), excellent electron transport and injection characteristics. Accordingly, the condensed cyclic compound represented by Formula (1) is suitable for use in an organic light-emitting device.

Furthermore, solution coating described above is expected as a more efficient method of manufacturing an organic light-emitting device. An organic material applicable to solution coating is required to have a high solubility to a solvent and excellent film stability after coating.

The condensed cyclic compound represented by Formula (1) includes azine-containing groups represented by Formulae (2) to (5) and has excellent solubility to a solvent. Also, as described above, the condensed cyclic compound represented by Formula (1) has a relatively high glass transition temperature (Tg), and degeneration and/or deformation thereof caused by heat generated when the solvent is removed after the formation of the coating film may be substantially prevented. Accordingly, the condensed cyclic compound may be easily applicable to solution coating. Furthermore, an organic layer formed by solution coating using a composition including the condensed cyclic compound has a uniform thickness, and thus, the surface of the organic layer is substantially flat. Therefore, an organic light-emitting device manufactured by solution coating using the composition including the condensed cyclic compound represented by Formula (1) has no application spot of a driving voltage and no light emission spot and has a long light emission lifespan.

Examples of the condensed cyclic compound represented by Formula (1) are Compounds 1-1 to 1-126, but embodiments of the present disclosure are not limited thereto:

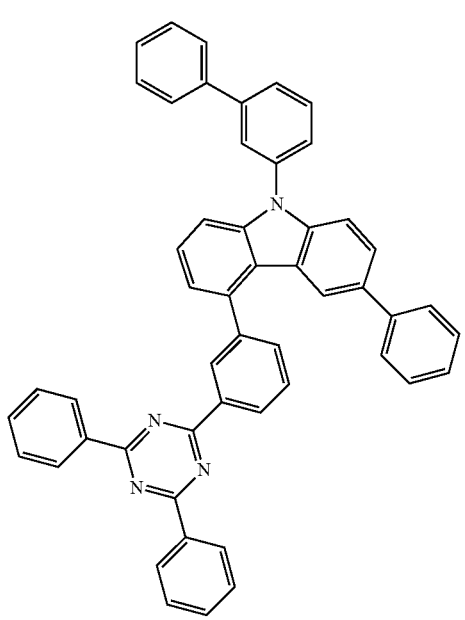

1-1

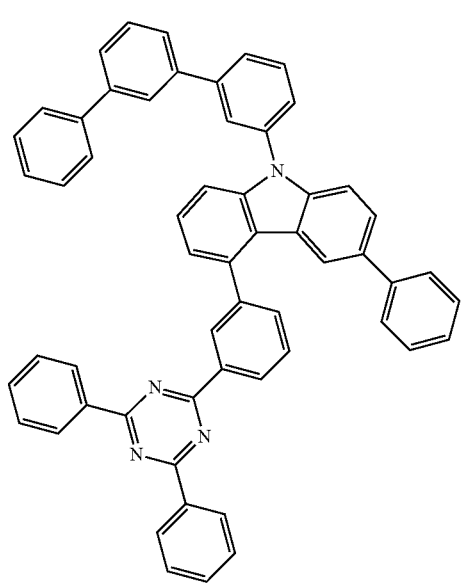

1-2

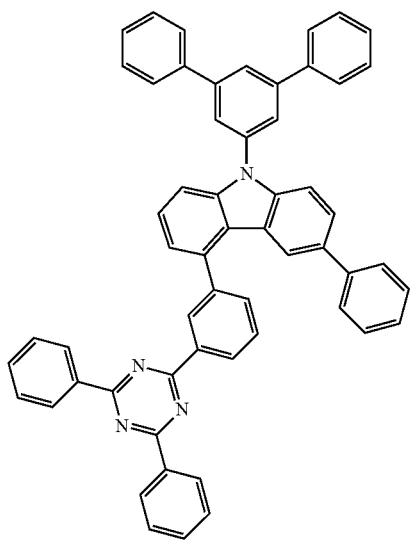

1-3

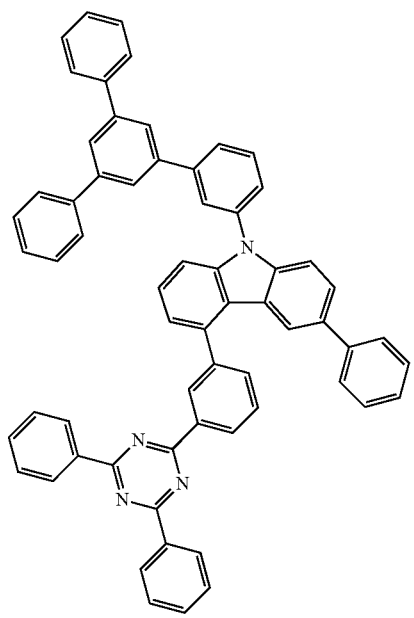

1-4

-continued
1-5
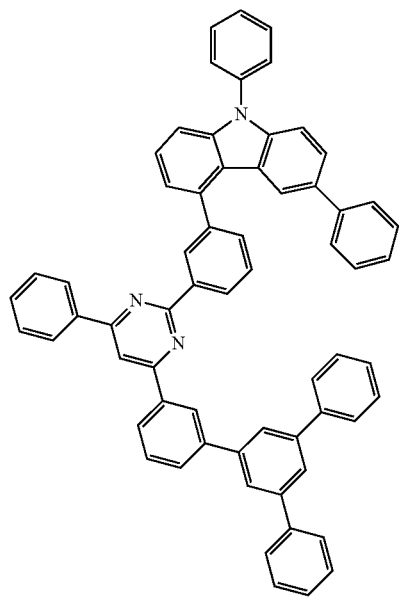
1-6
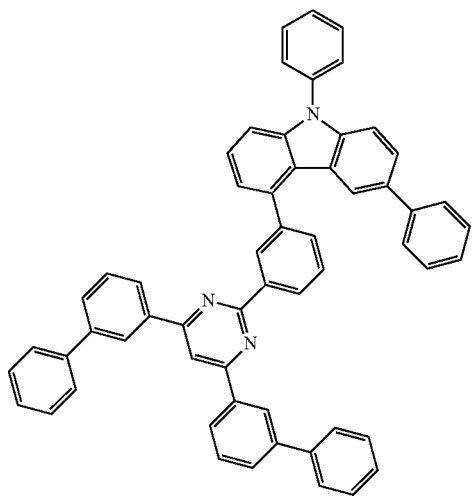
1-7
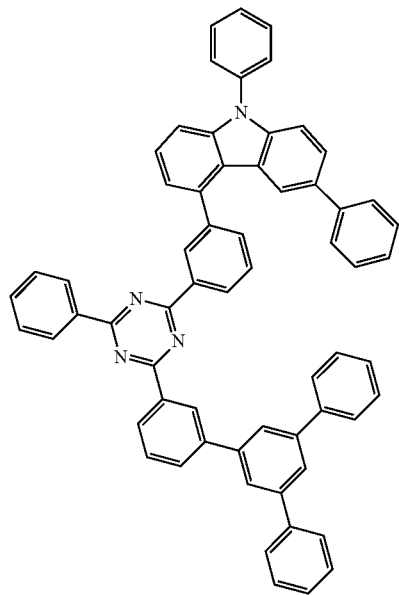
1-8
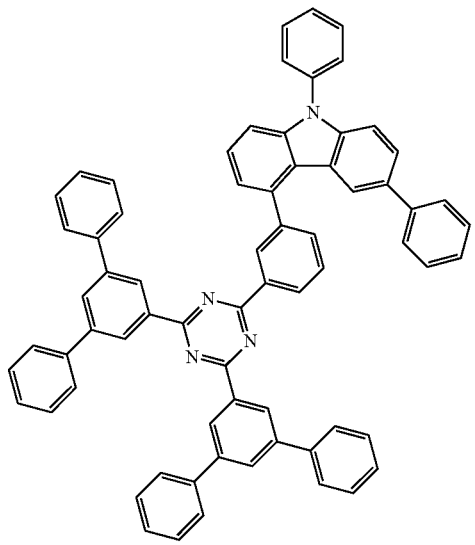

-continued
1-9
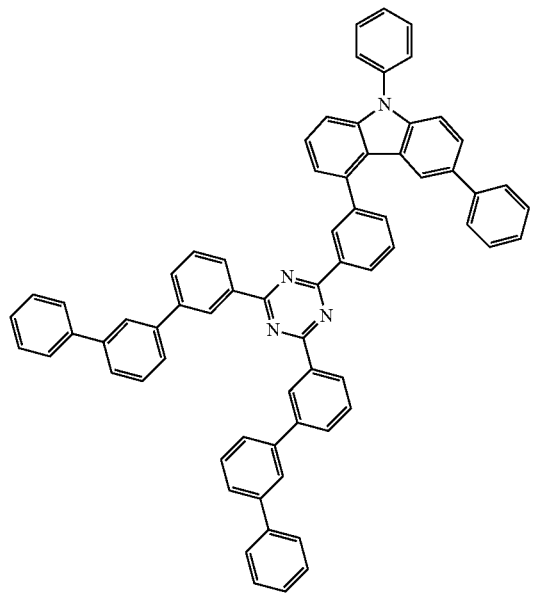
1-10
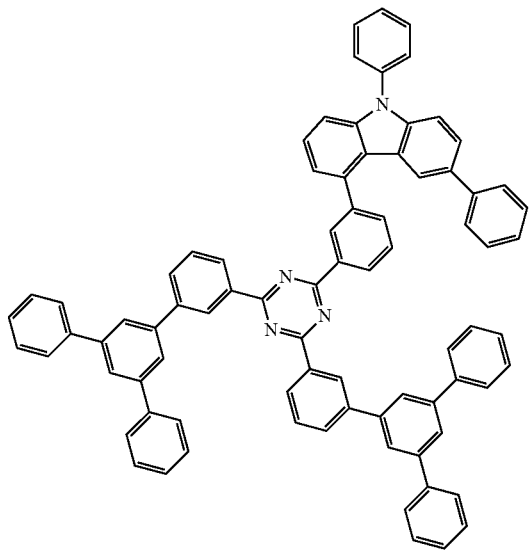
1-11
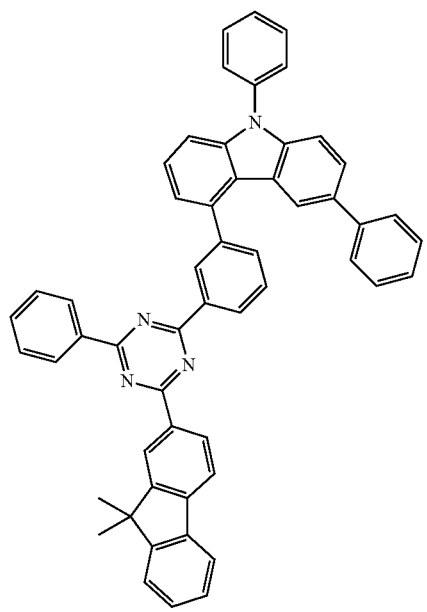
1-12
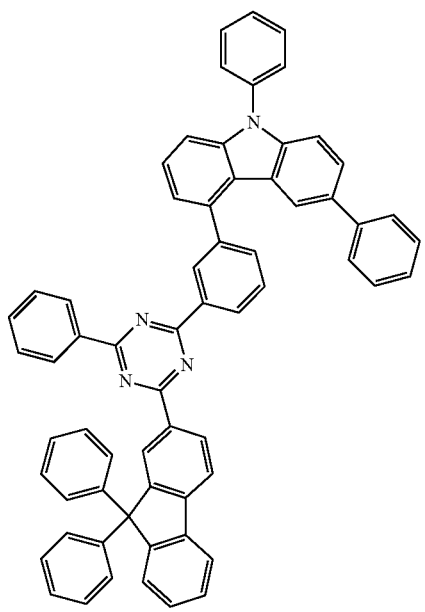

-continued
1-13
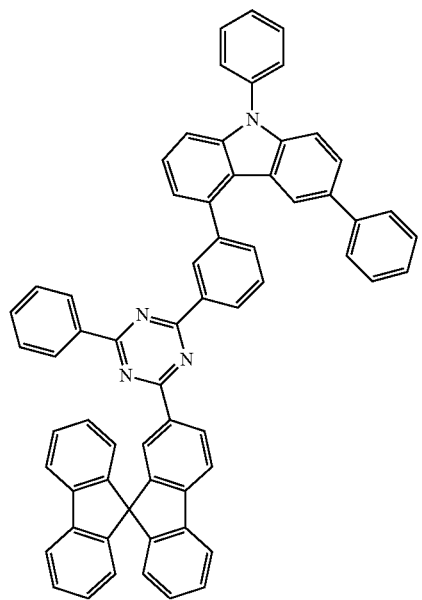
1-14
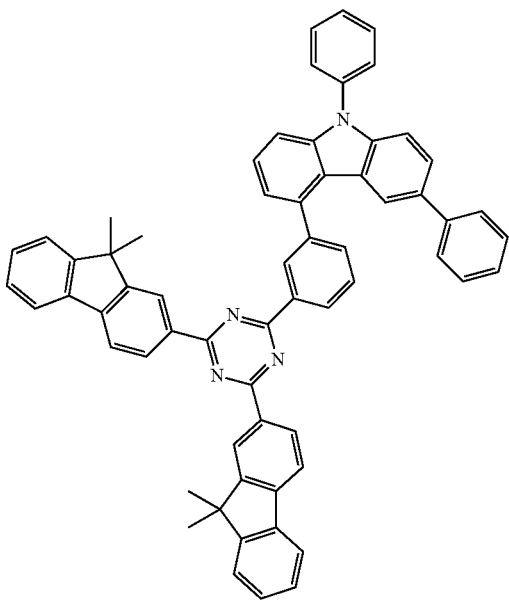
1-15
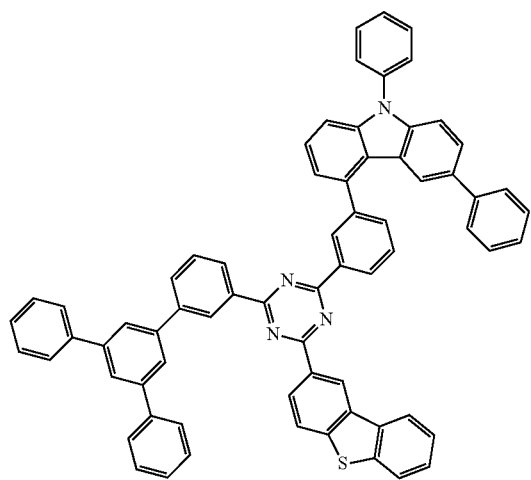
1-16
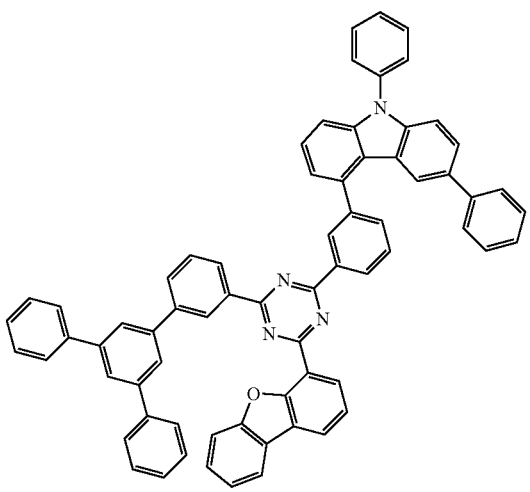

1-17
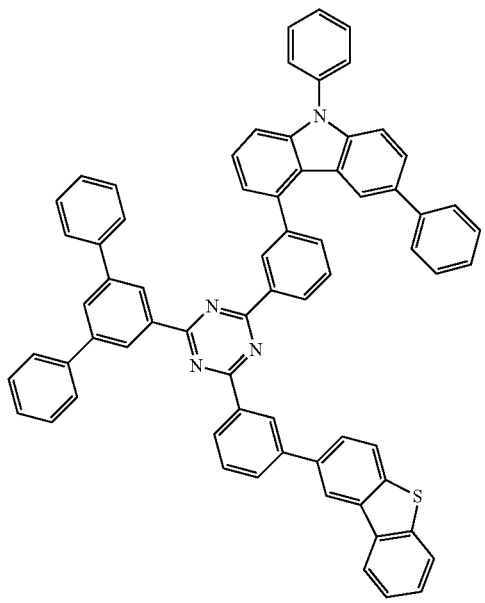
1-18
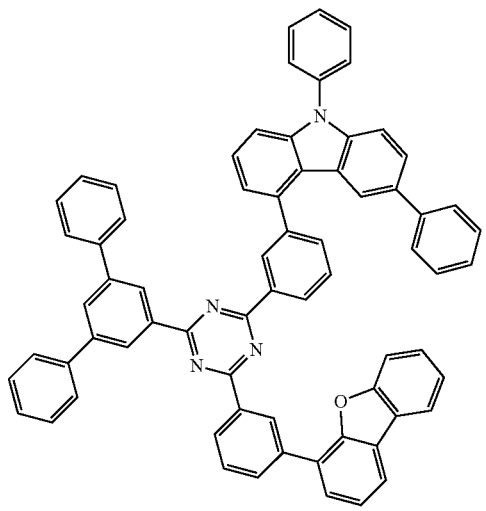
1-19
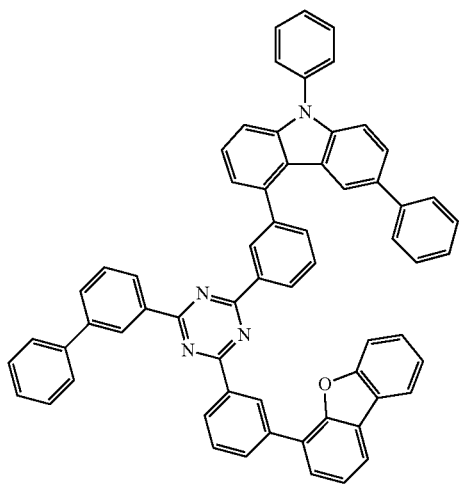
1-20
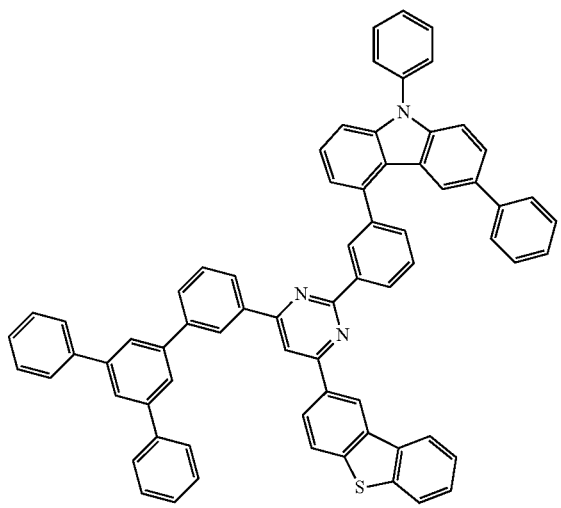

1-21
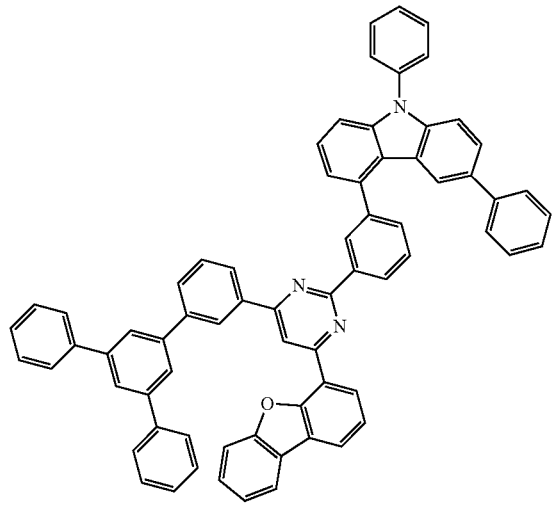
1-22
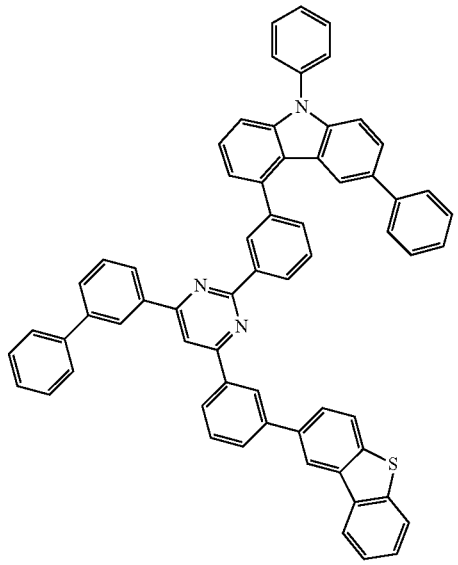
1-23
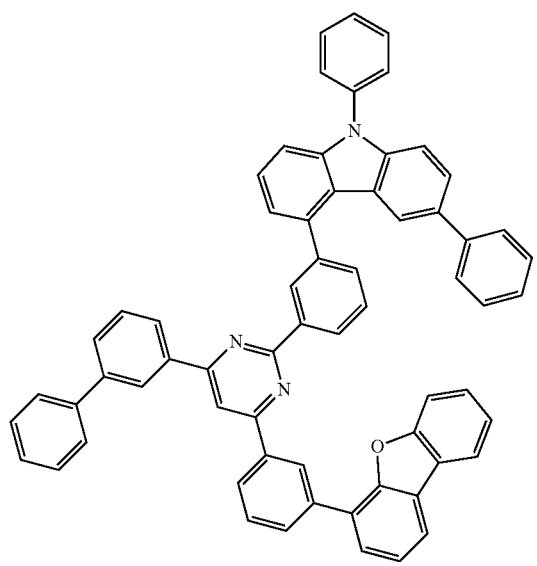
1-24
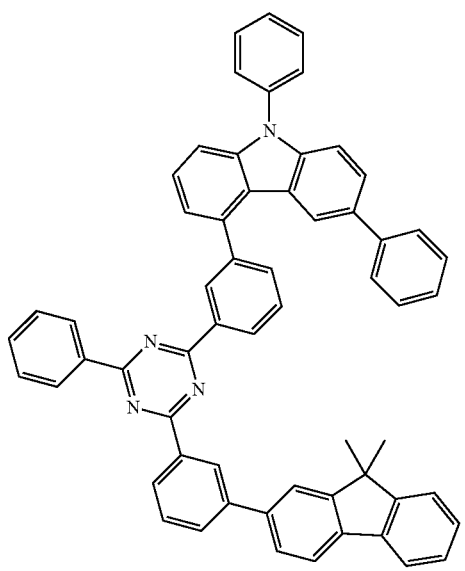

1-25
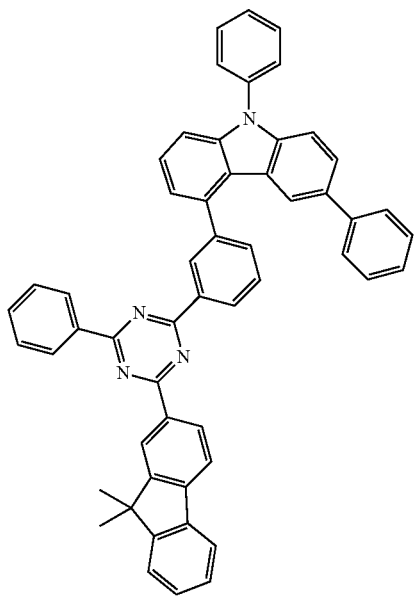
1-26
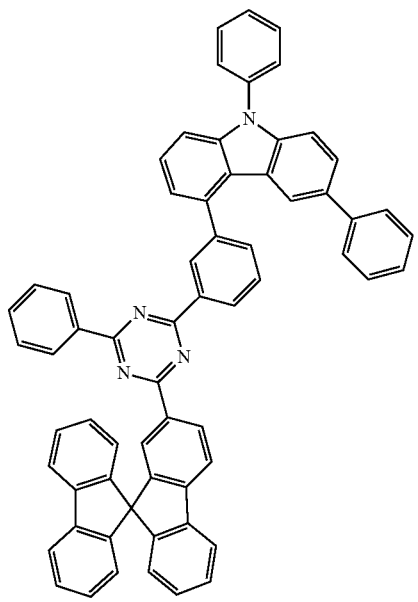
1-27
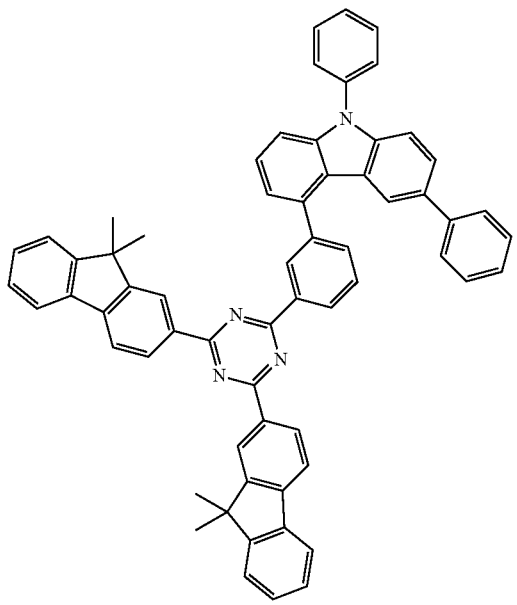
1-28
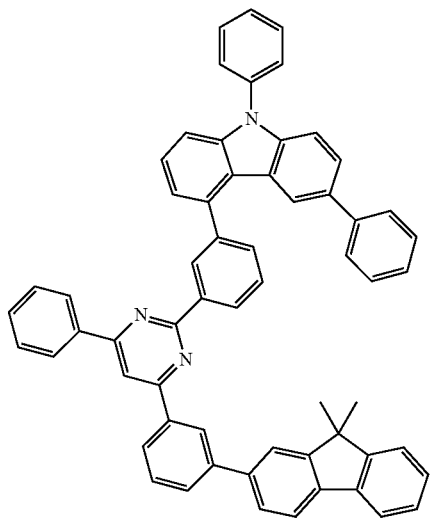

1-29
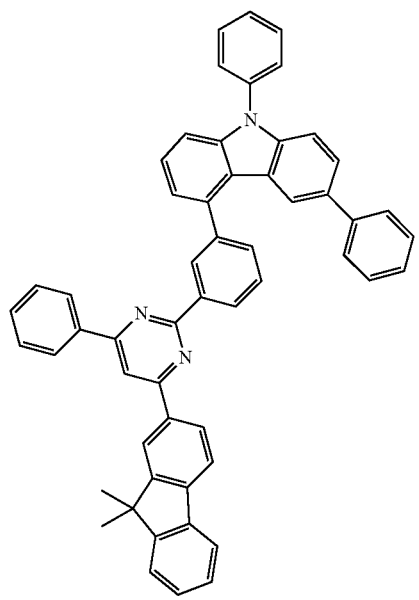
1-30
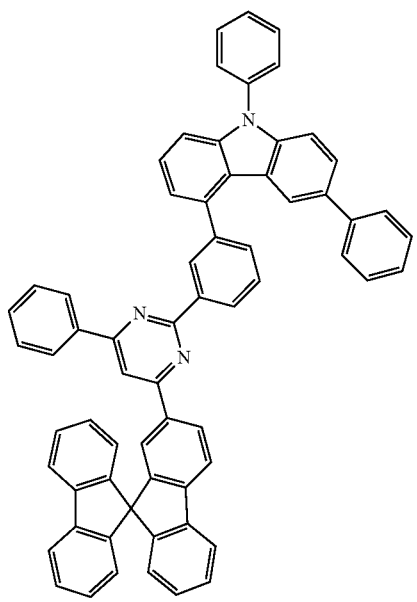
1-31
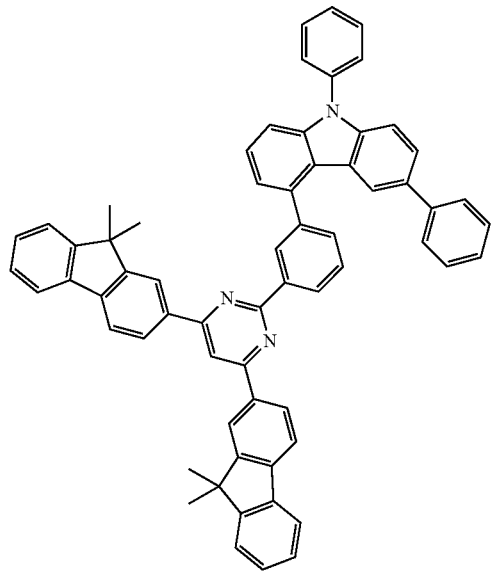
1-32
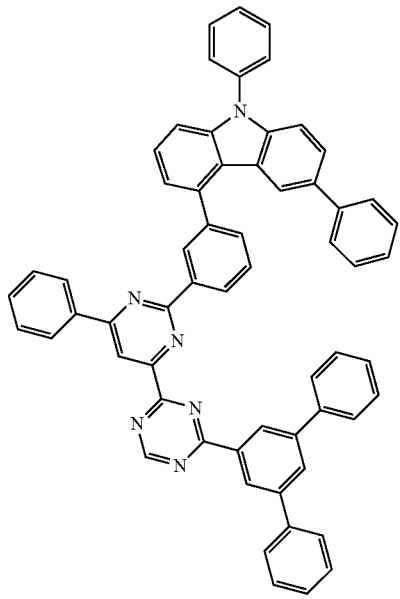

-continued
1-33
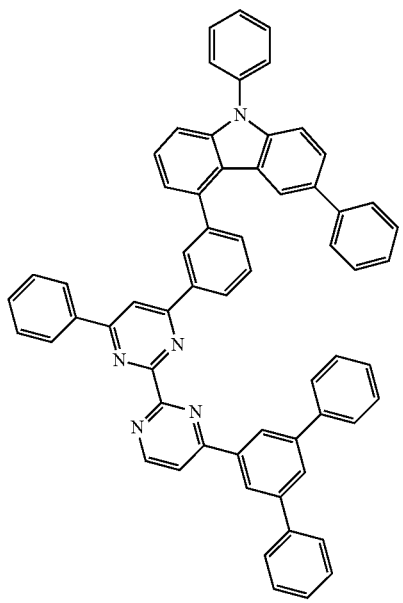
1-34
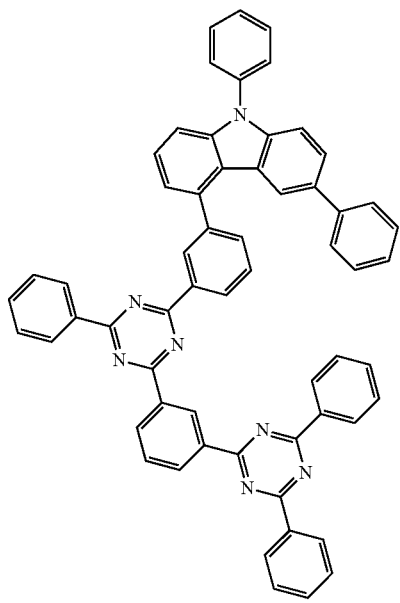
1-35
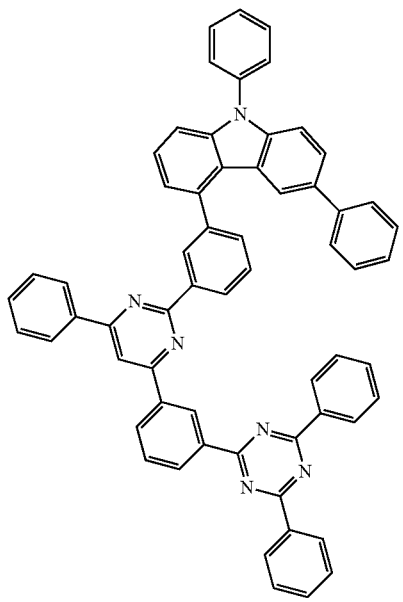
1-36
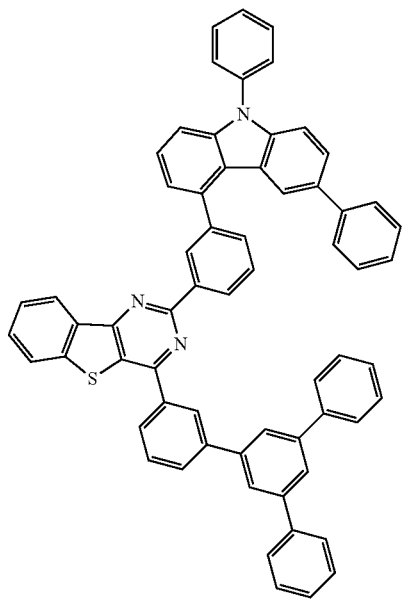

-continued
1-37
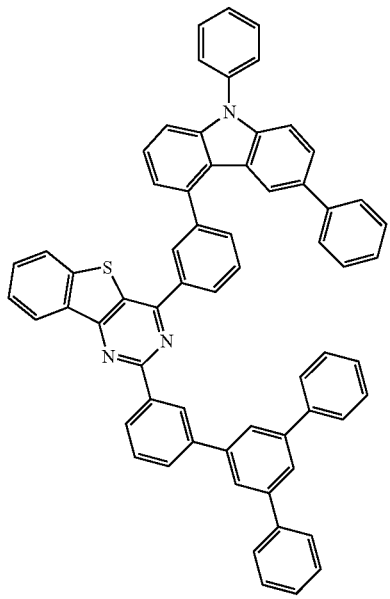
1-38
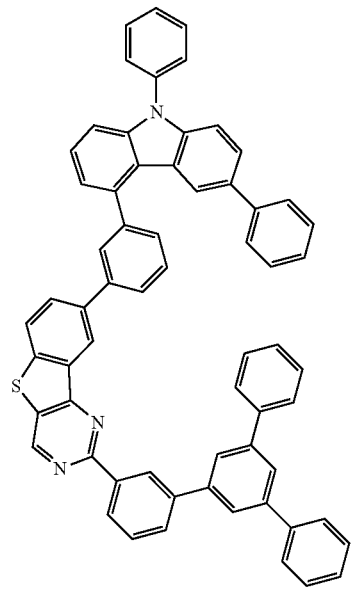
1-39
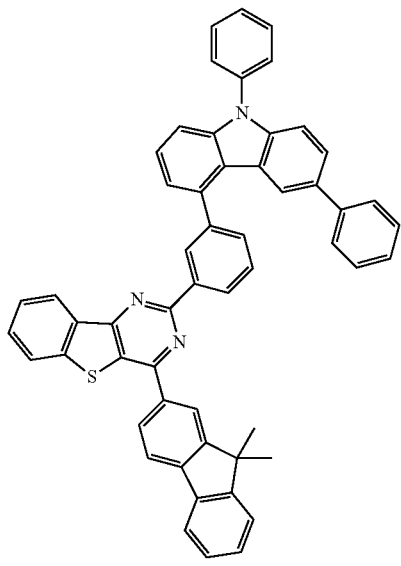
1-40
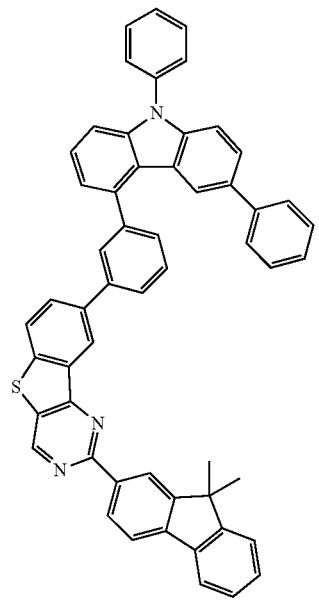

1-41
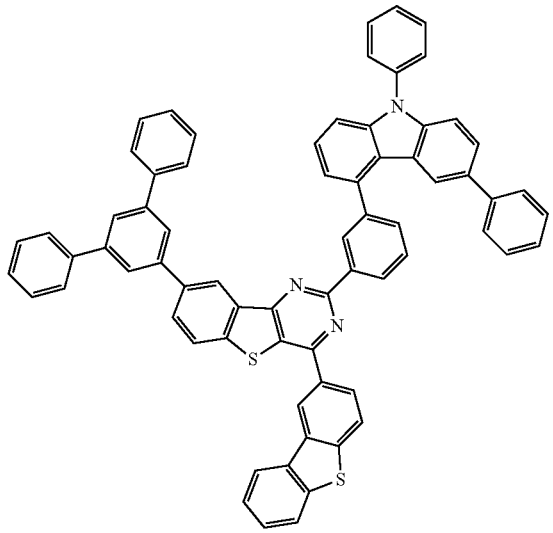
1-42
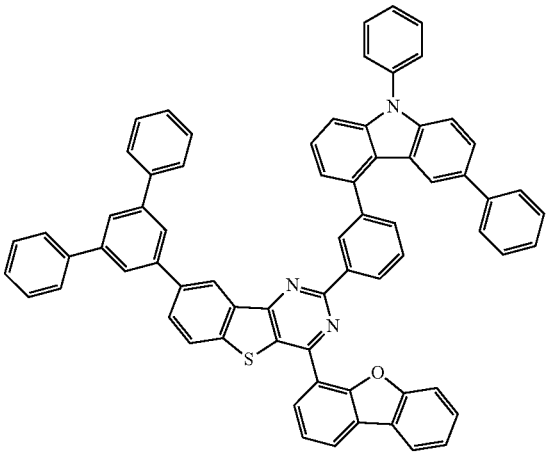
1-43
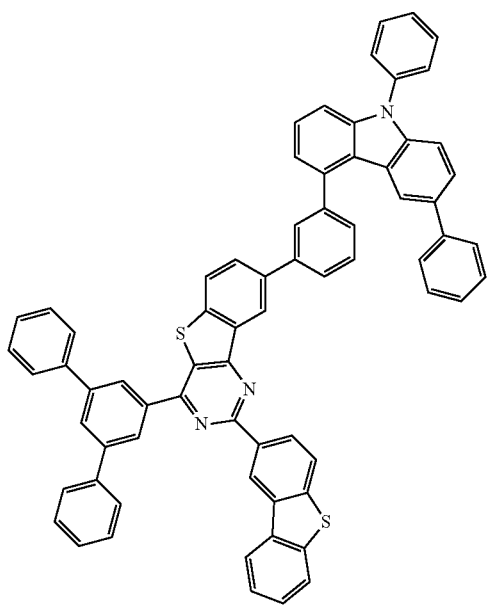
1-44
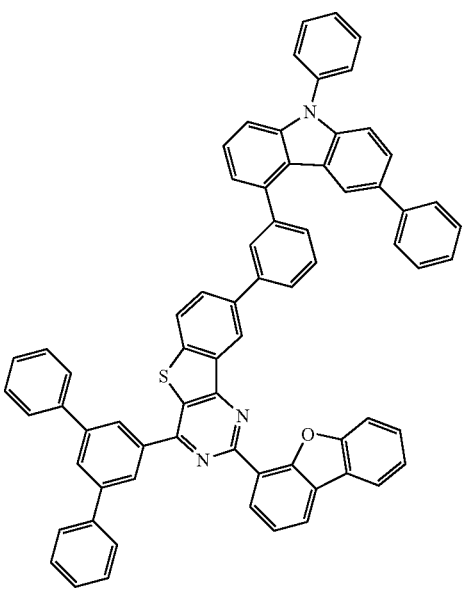

-continued
1-45
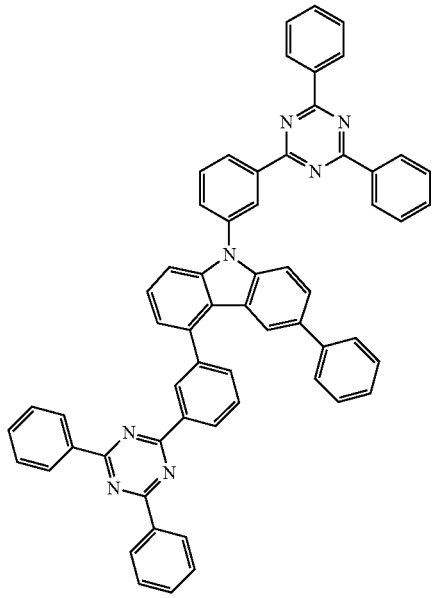
1-46
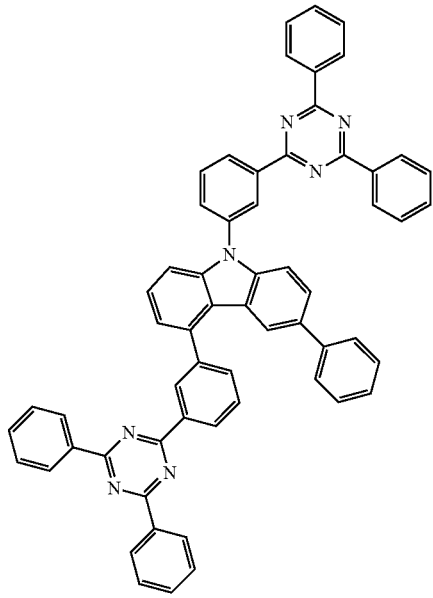
1-47
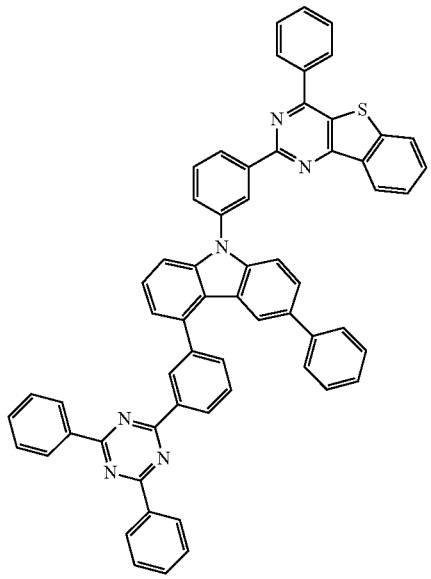
1-48
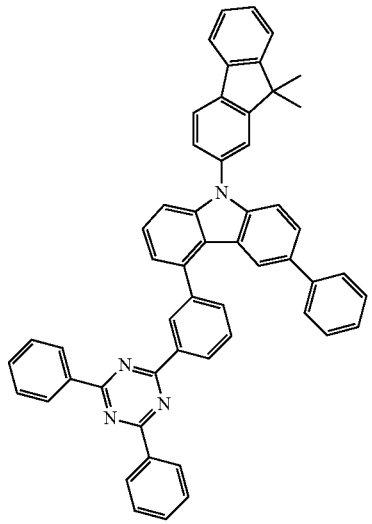

1-49
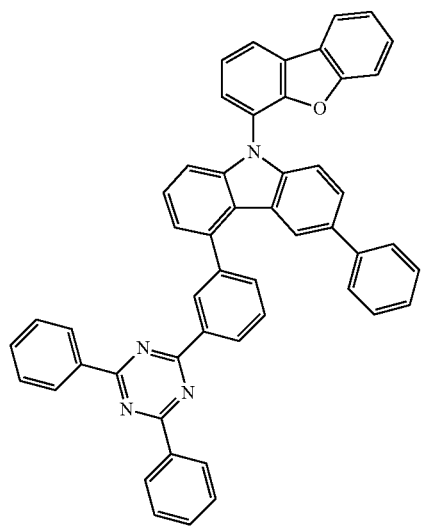
1-50
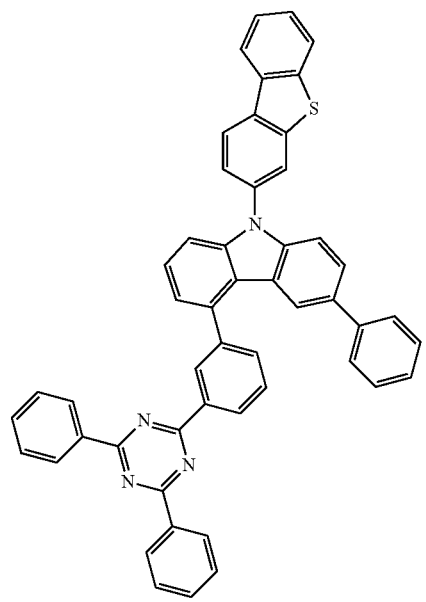
1-51
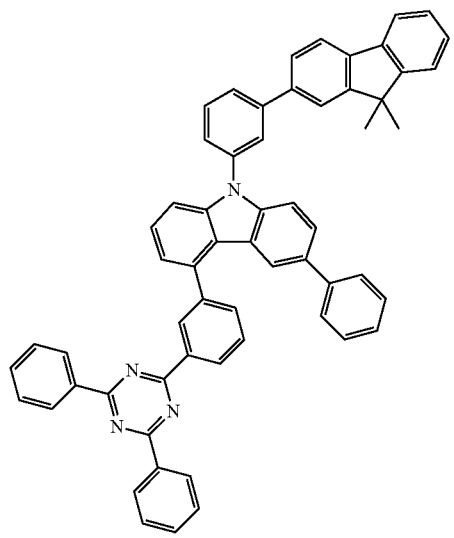
1-52
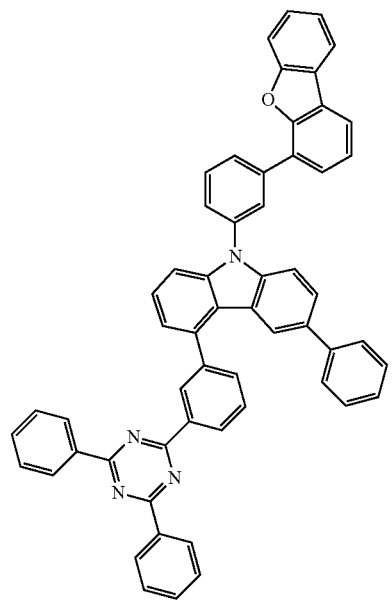

1-53
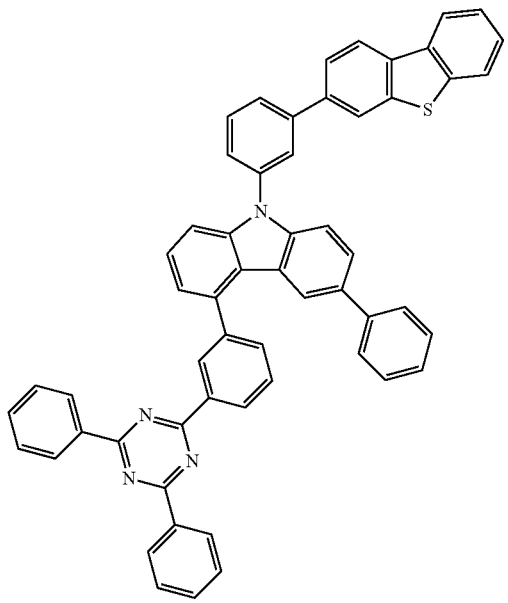
1-54
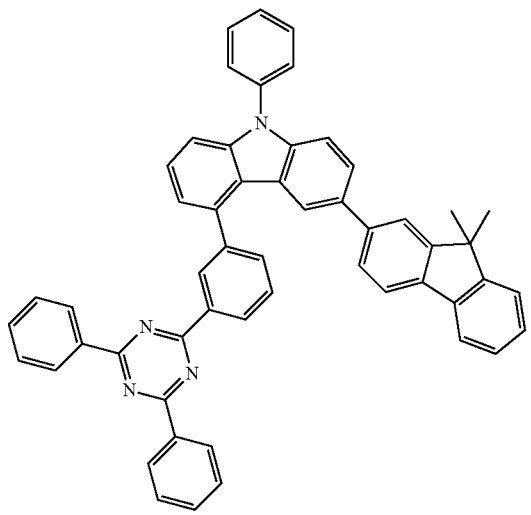
1-55
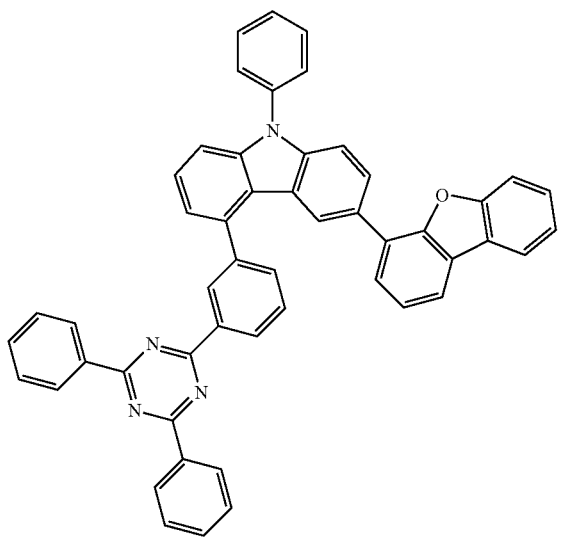
1-56
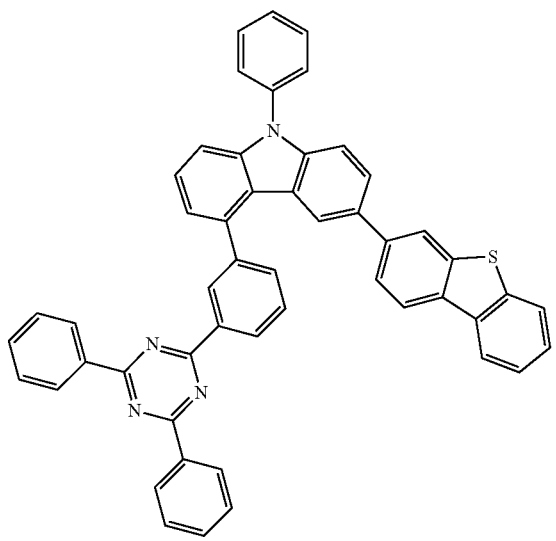

1-57
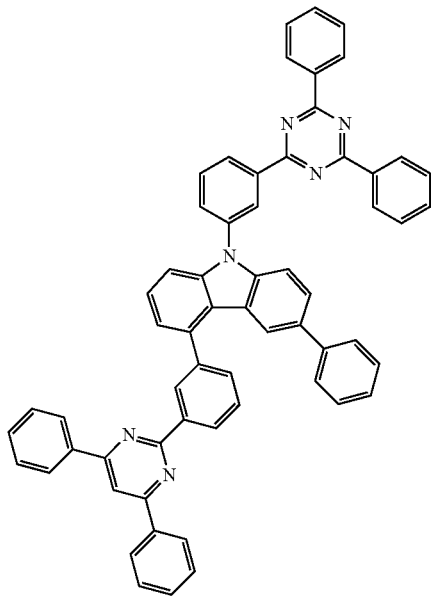
1-58
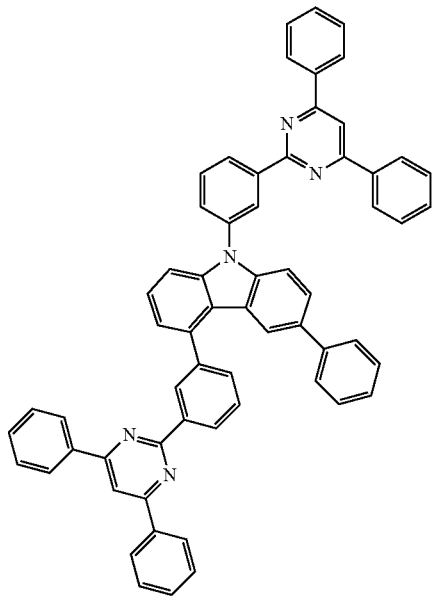
1-59
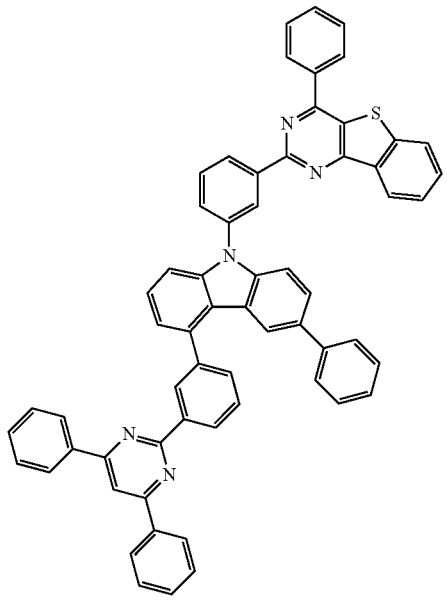
1-60
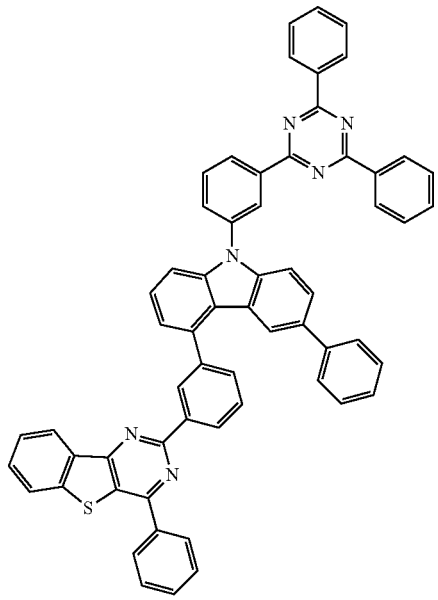

-continued
1-61
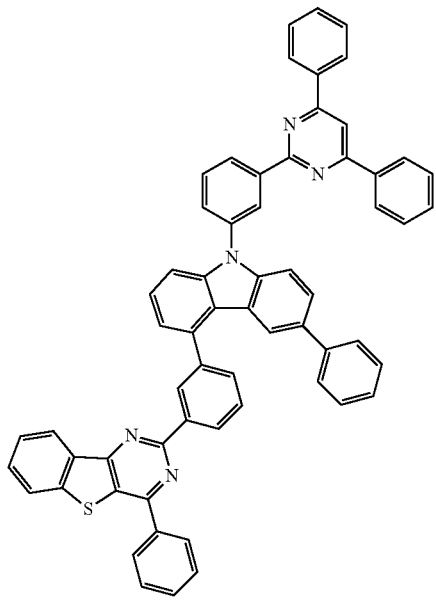
1-62
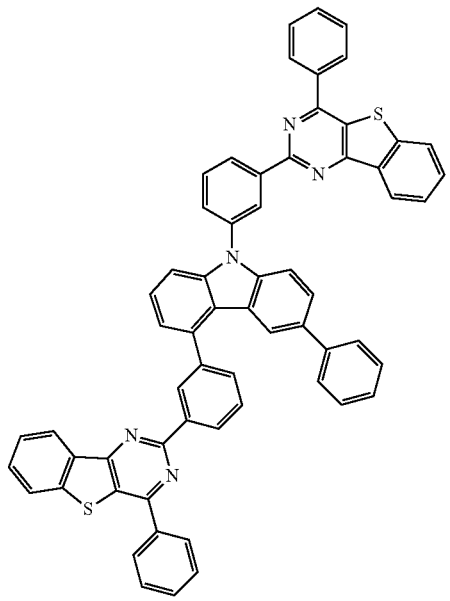
1-63
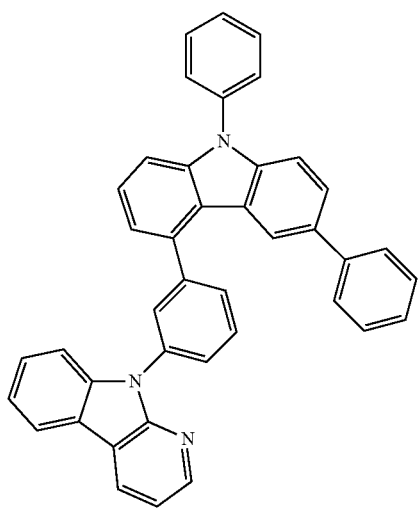
1-64
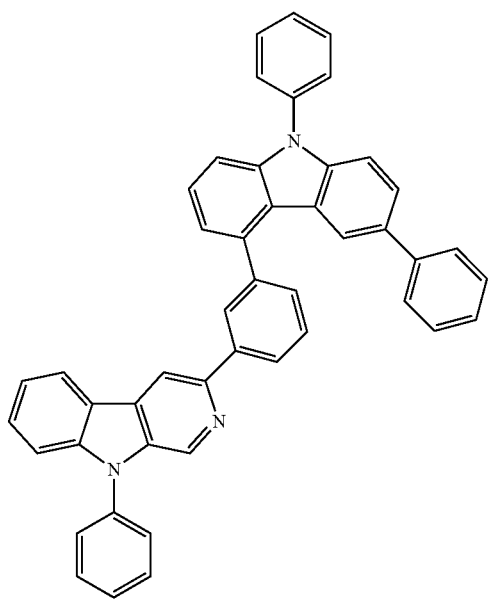

-continued
1-65
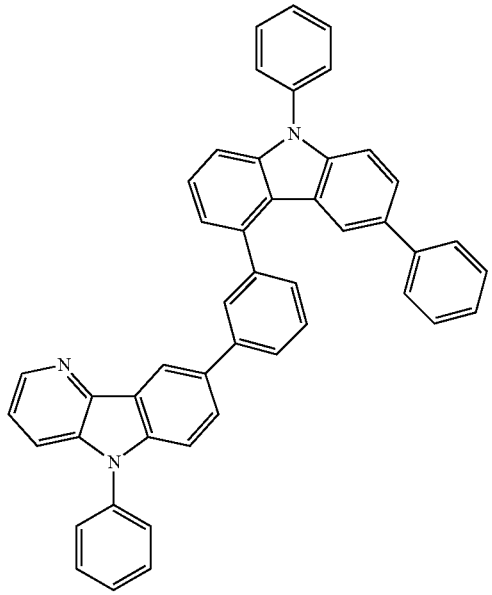
1-66
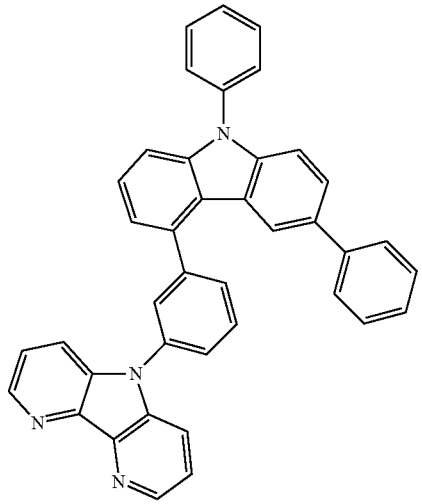
1-67
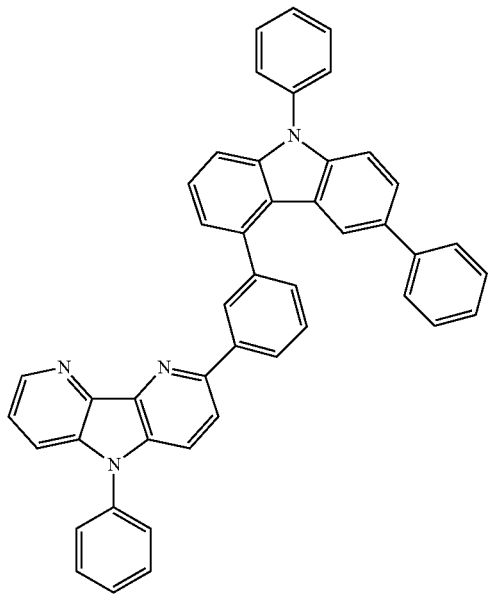
1-68
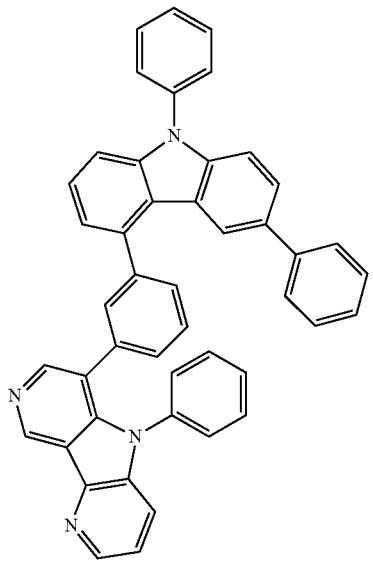

-continued
1-69
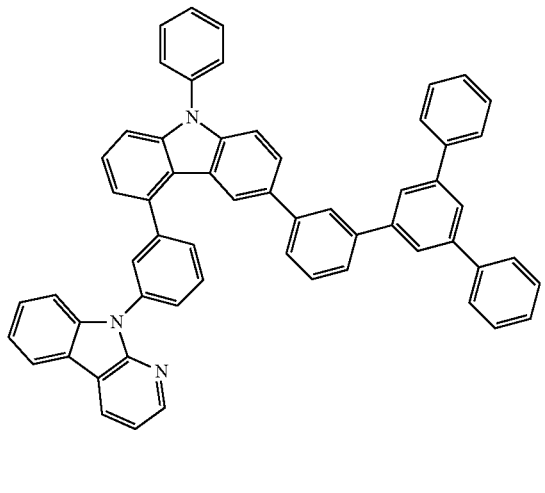
1-70
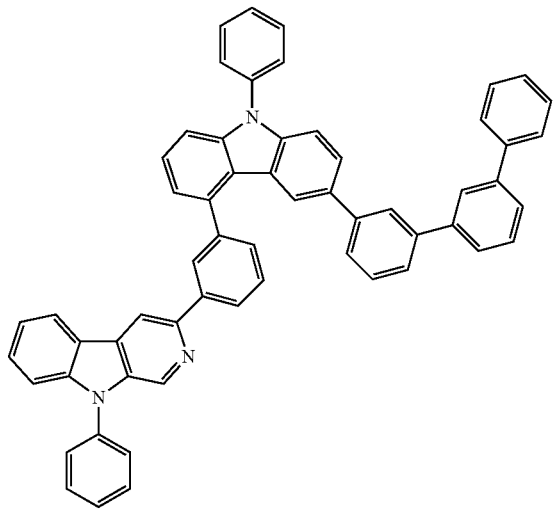
1-71
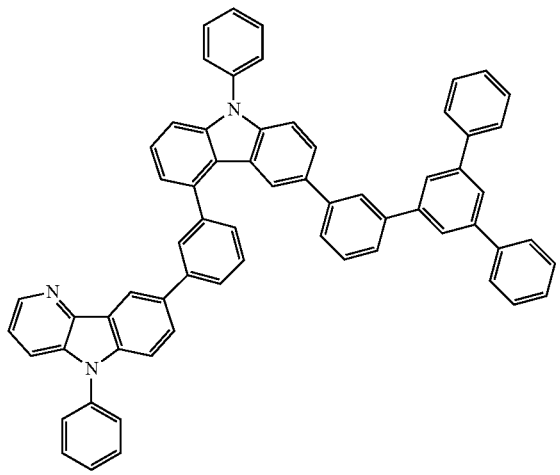
1-72
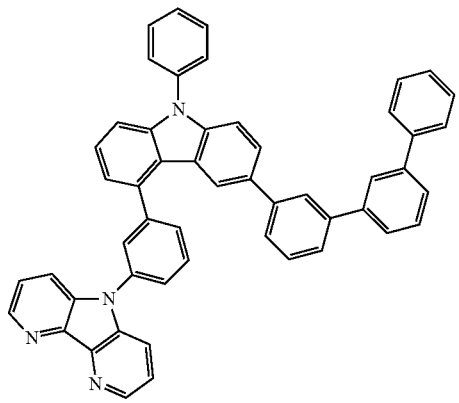
1-73
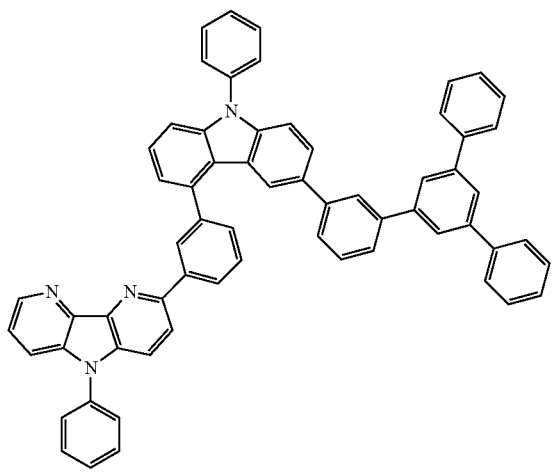
1-74
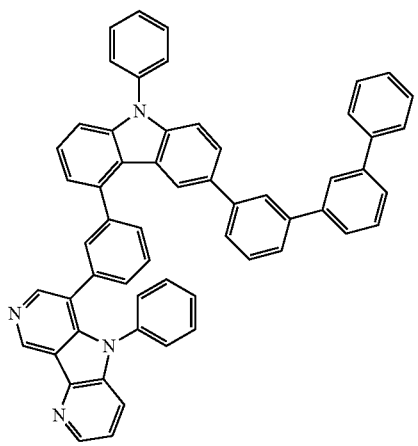

1-75
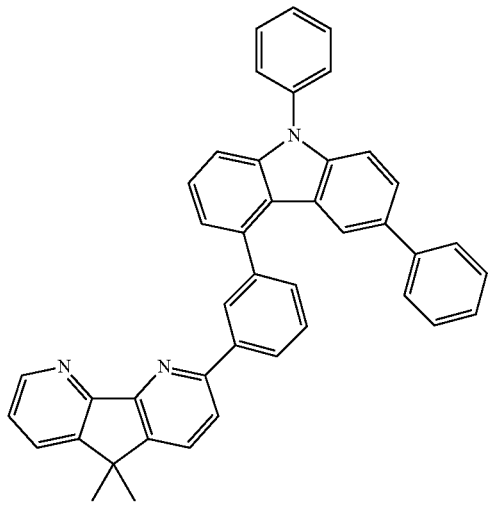
1-76
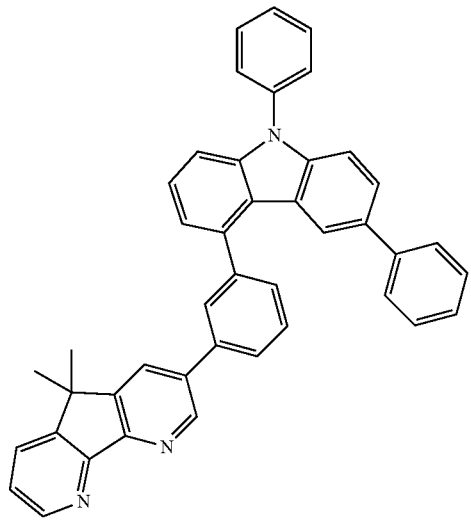
1-77
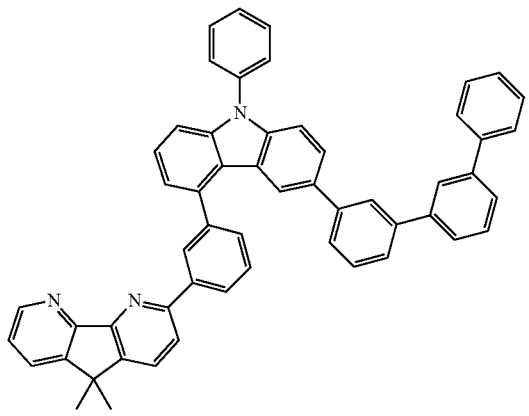
1-78
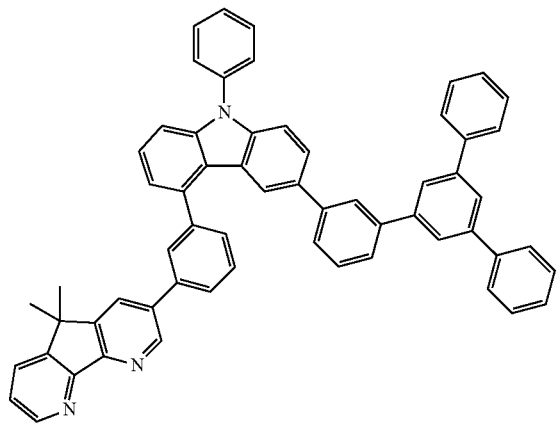
1-79
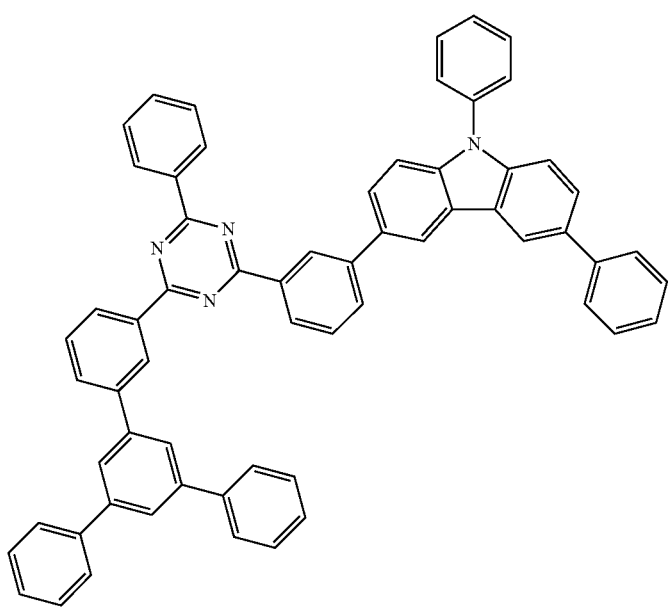

1-80
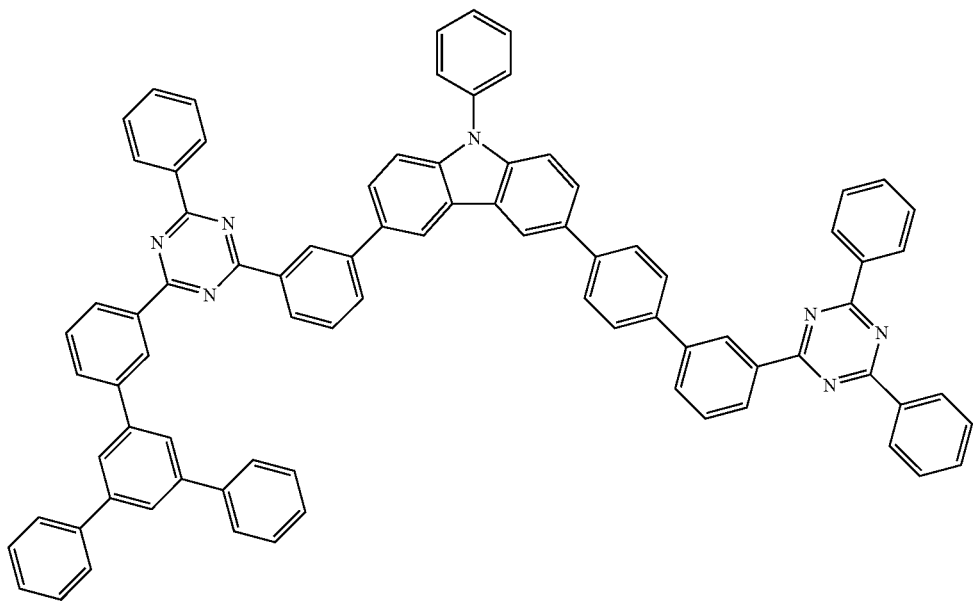
1-81
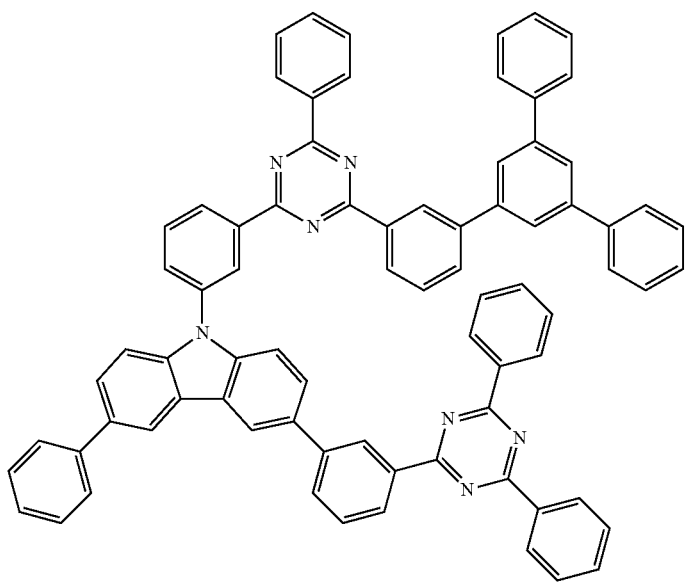

1-82
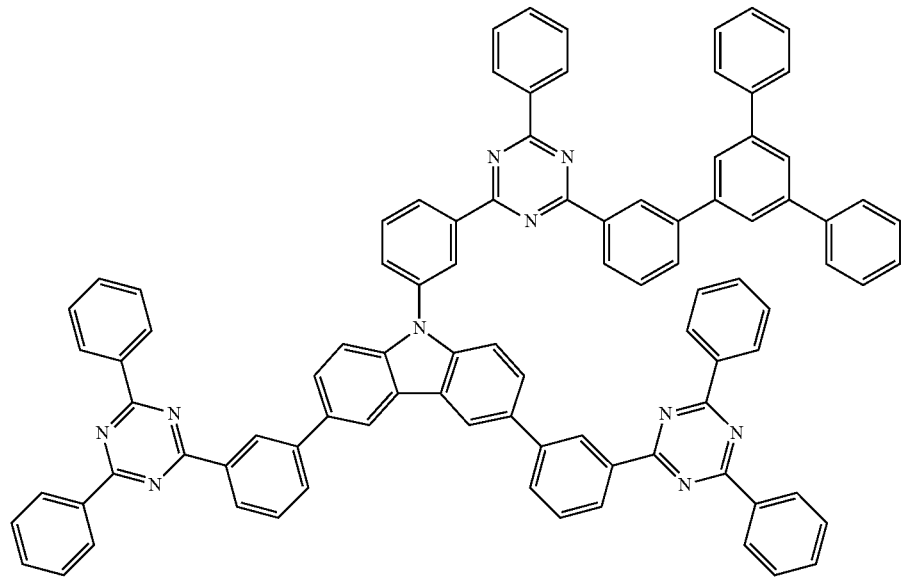
1-83
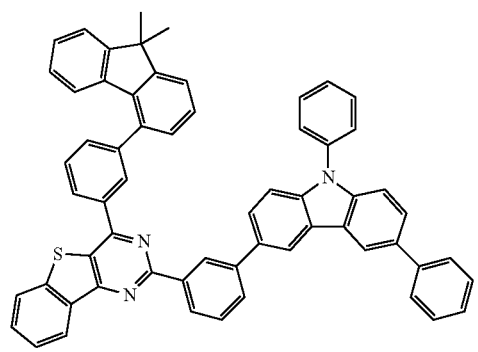
1-84
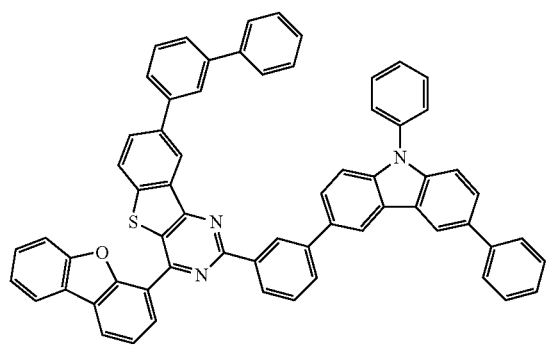
1-85
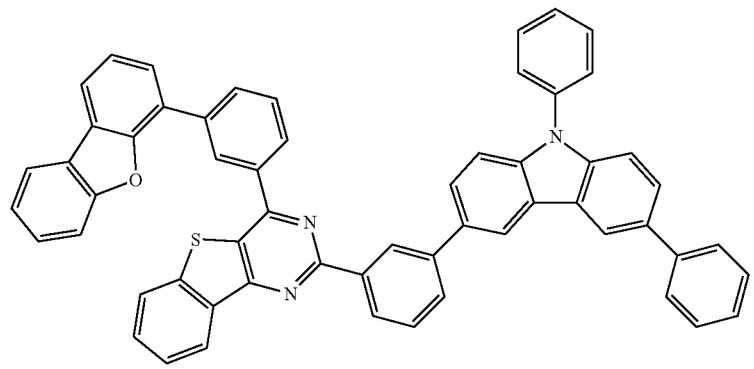

-continued
1-86
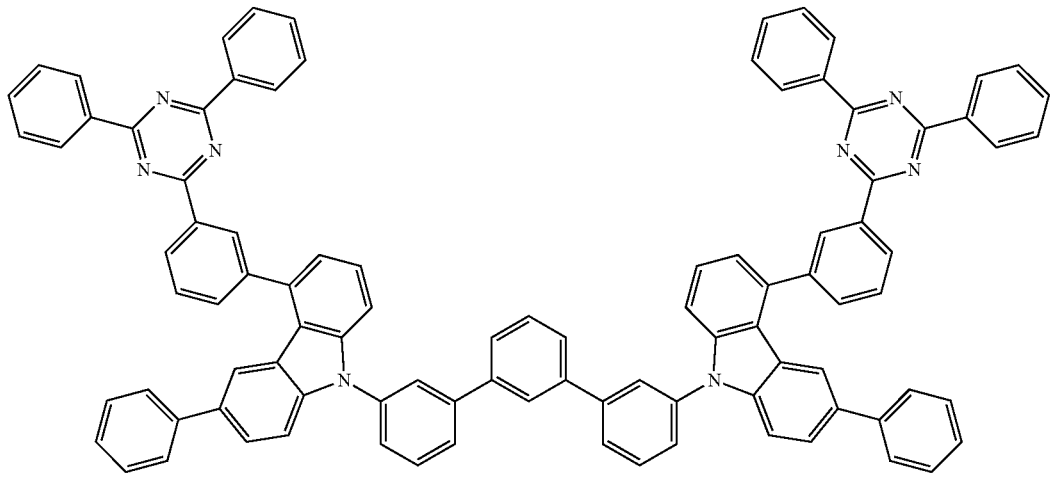
1-87
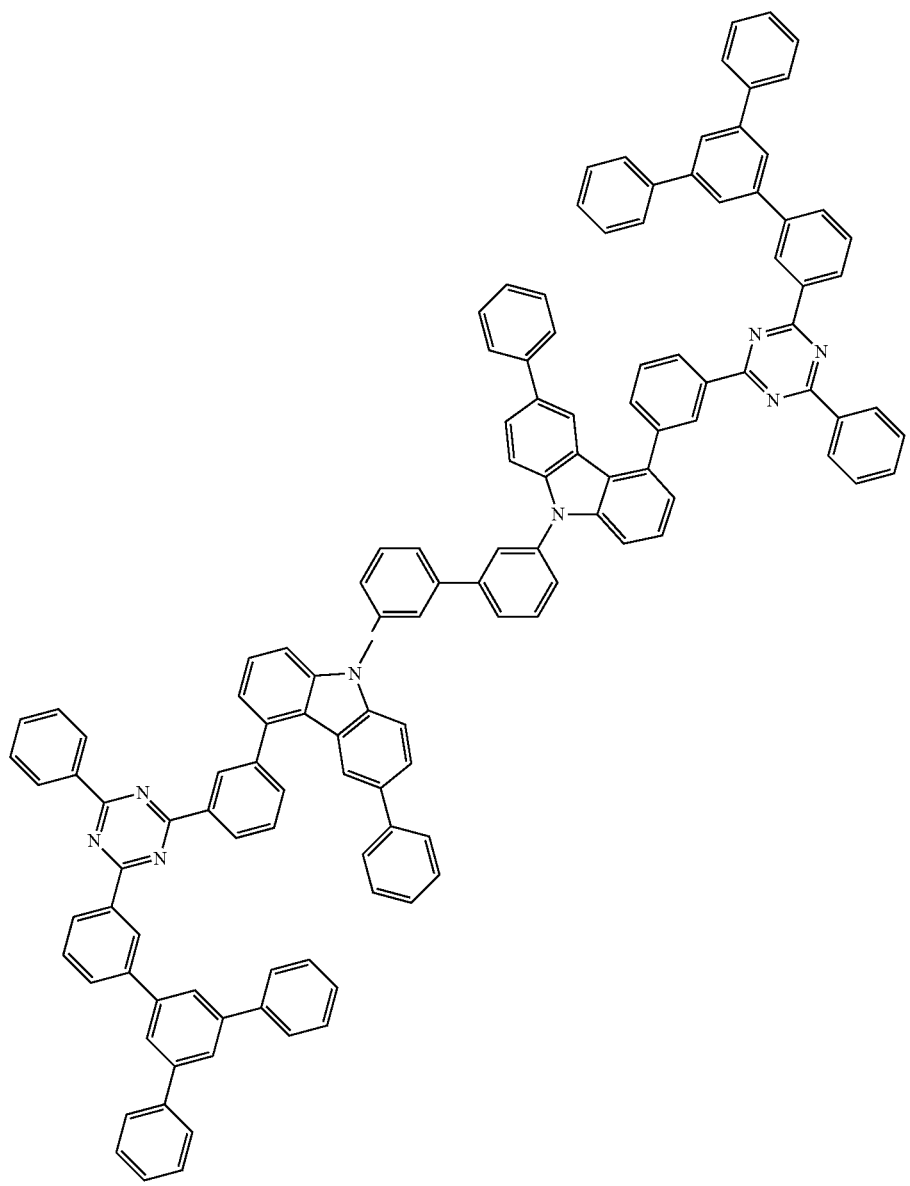

1-88
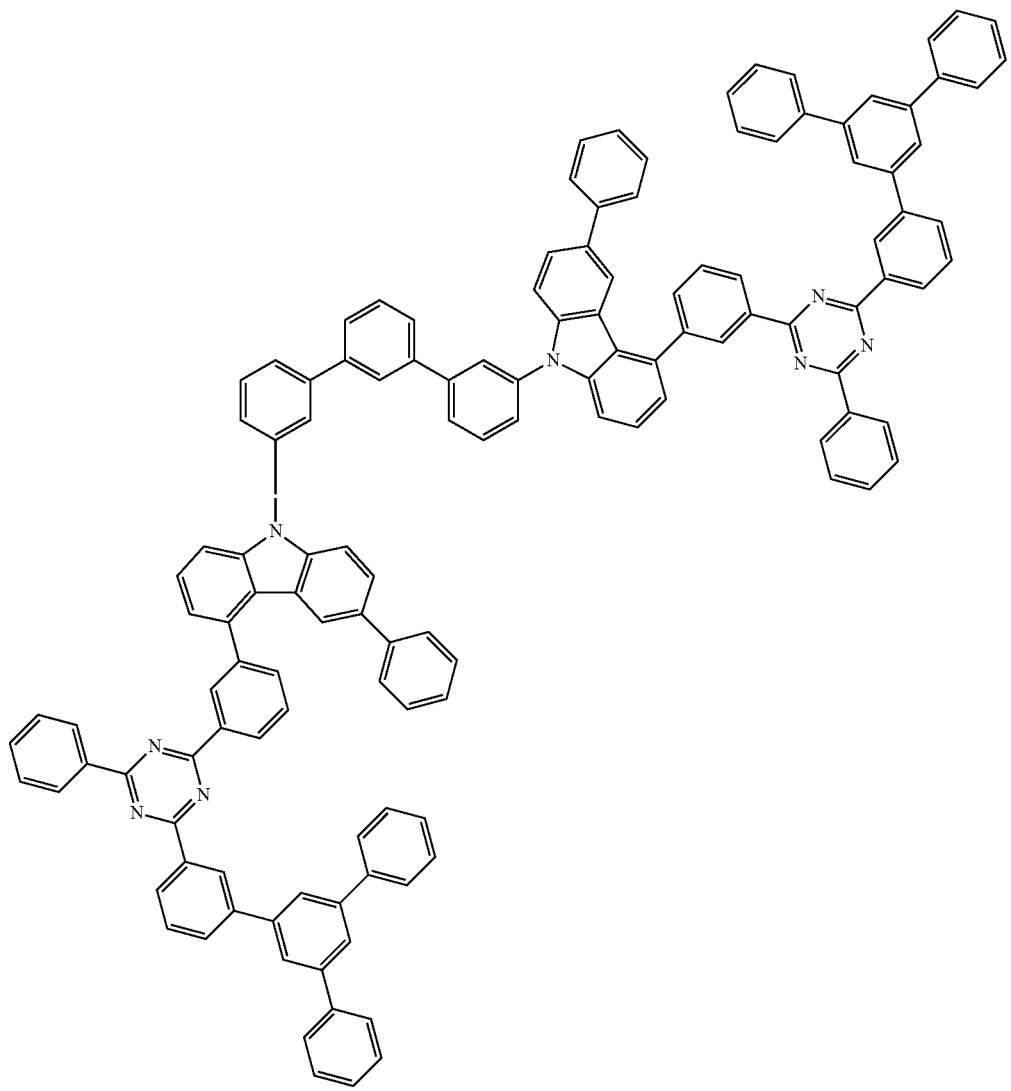
1-89
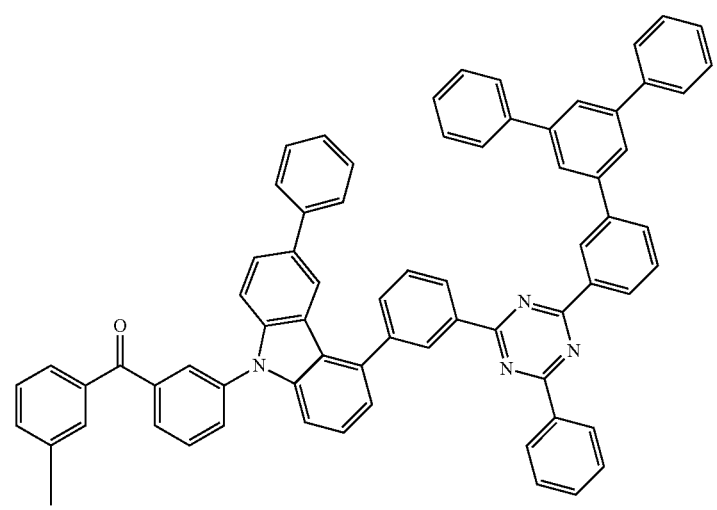

-continued
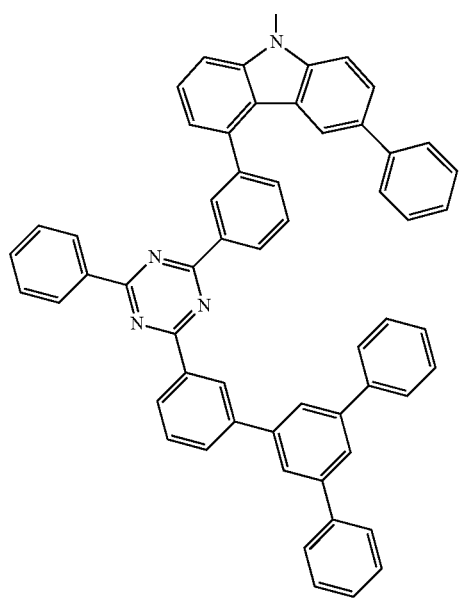
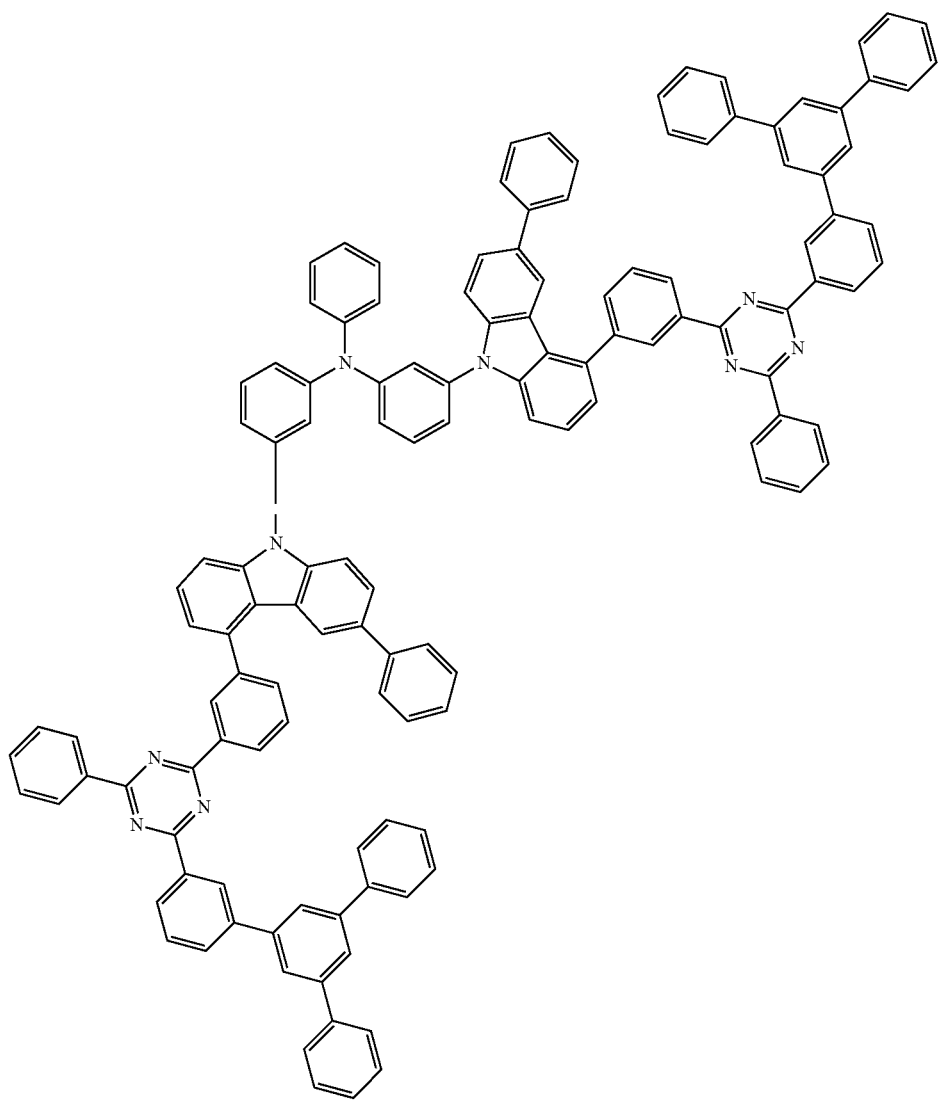
1-90

-continued
1-91
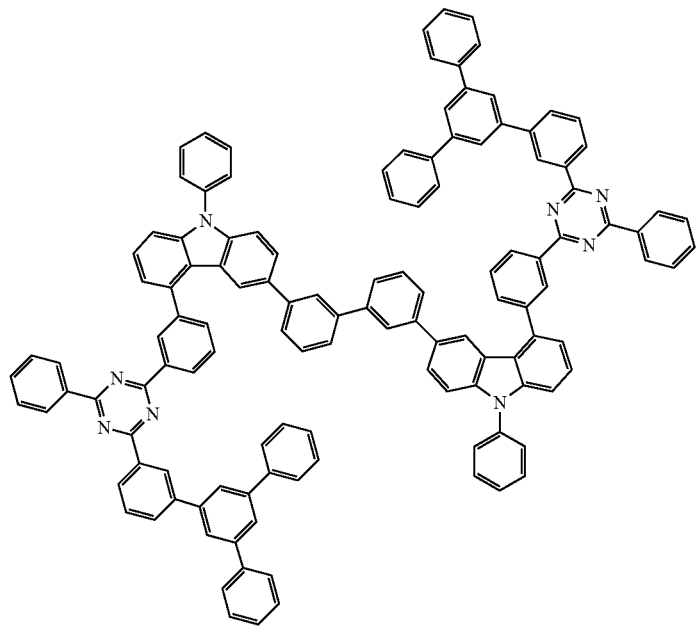
1-92
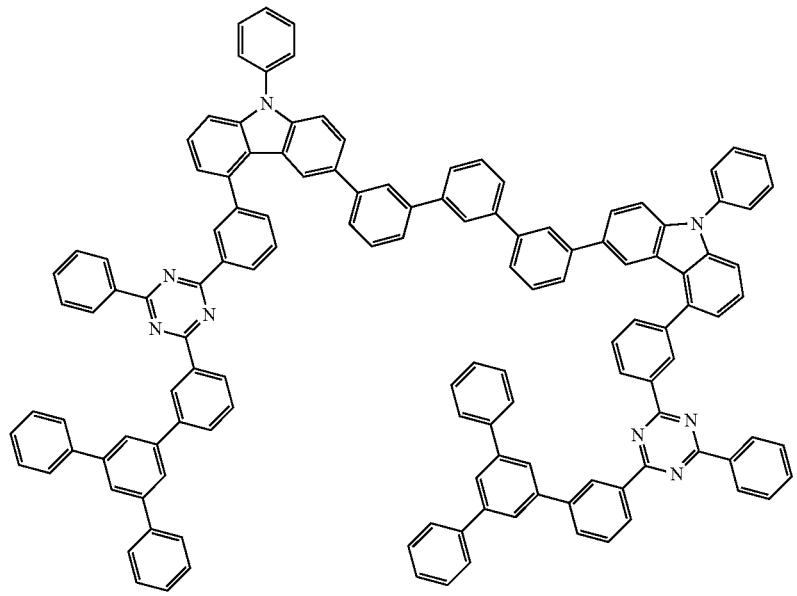

1-93
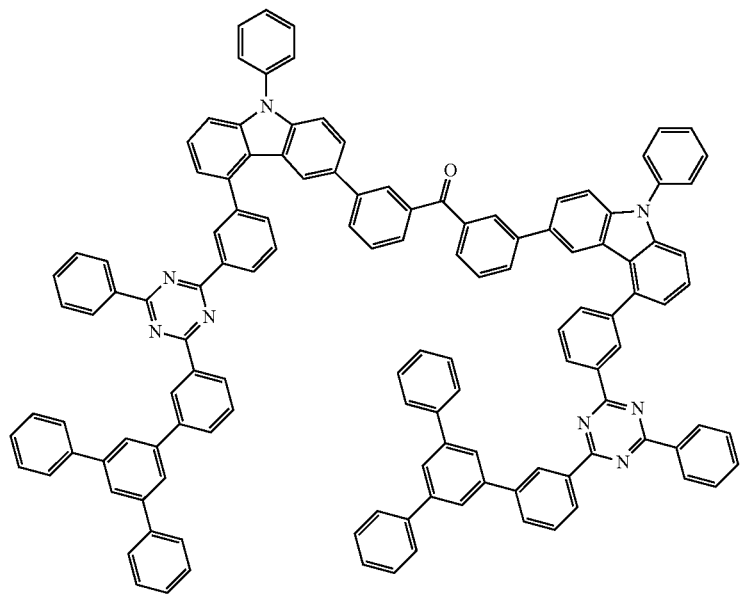
1-94
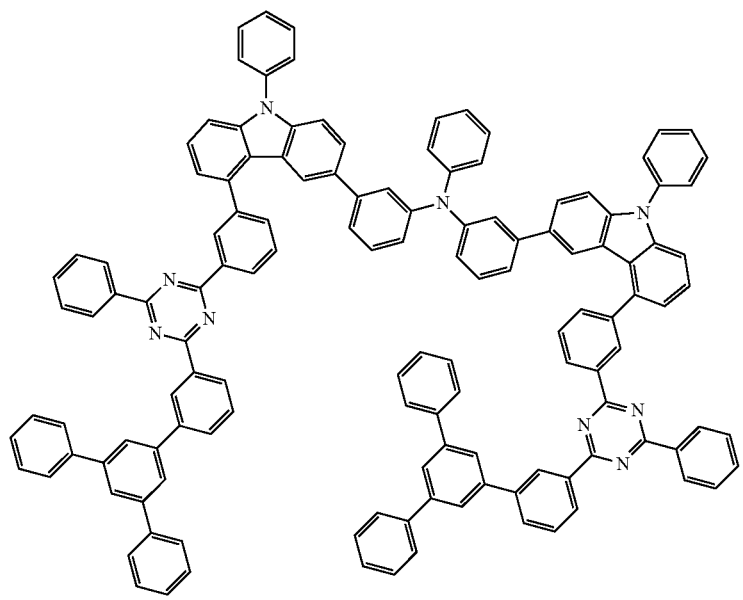

-continued
1-95
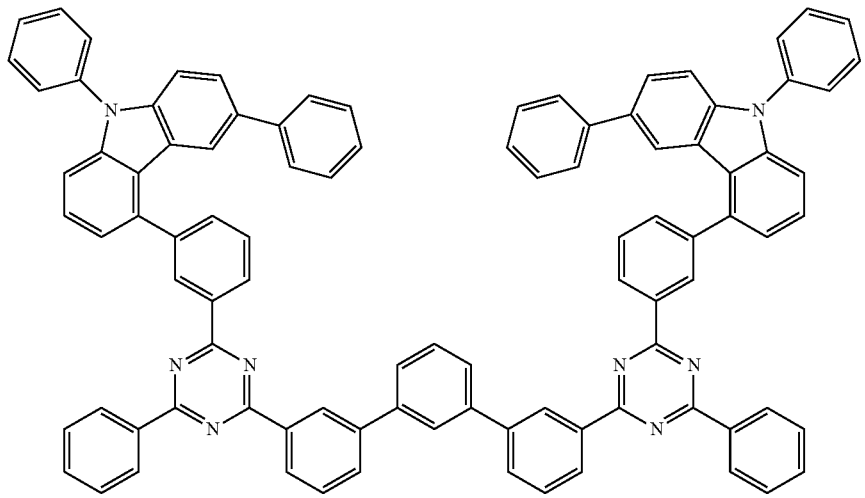
1-96
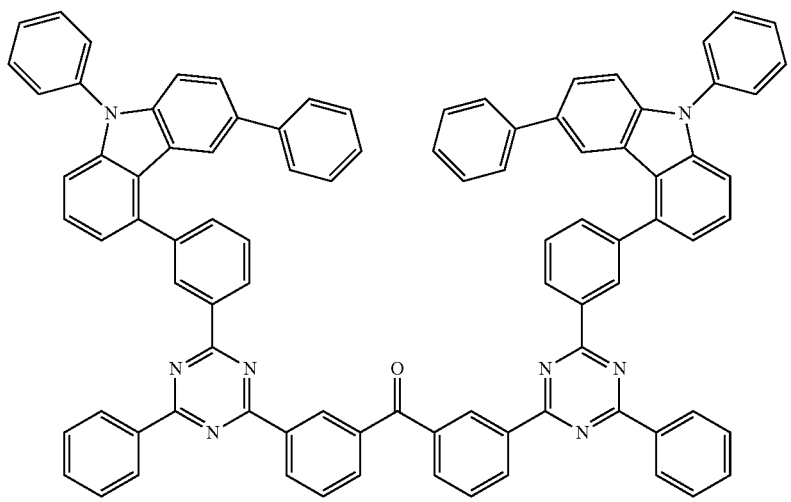
1-97
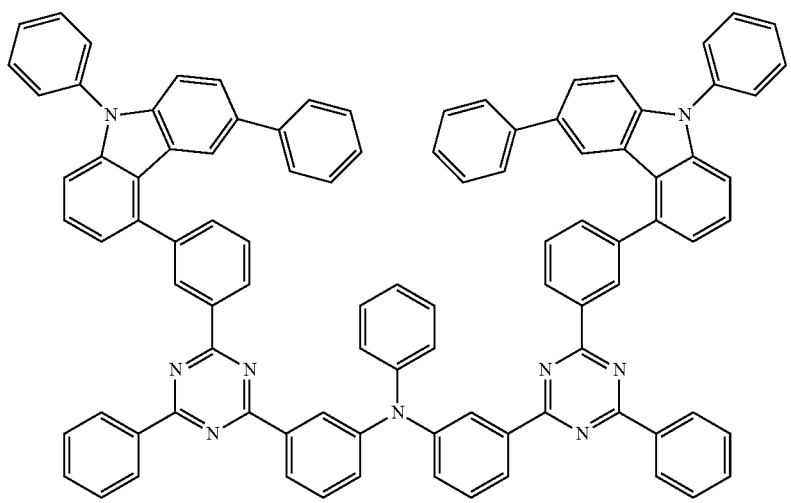

1-98
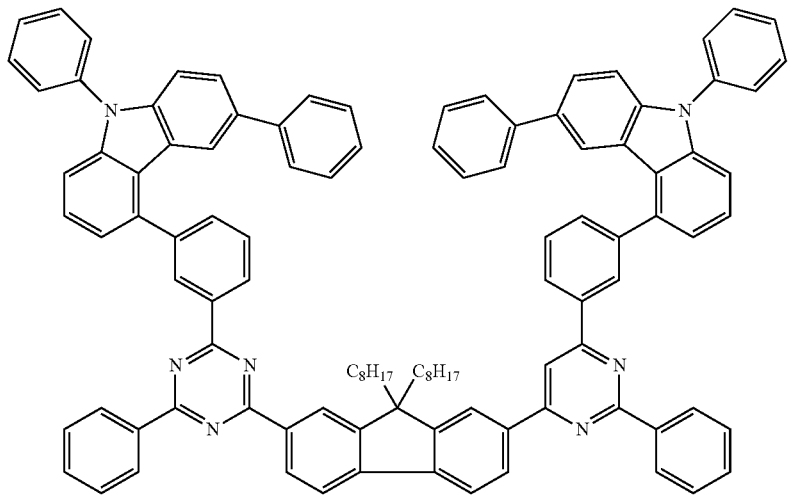
1-99
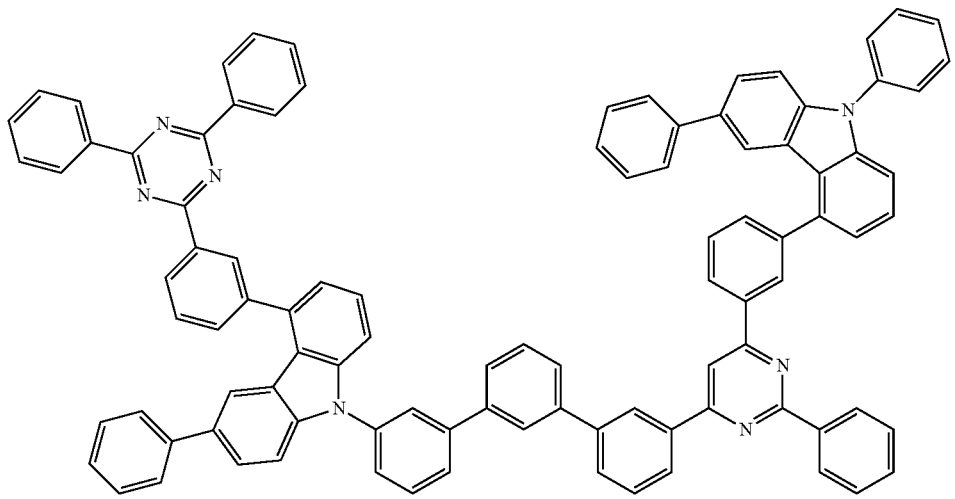
1-100
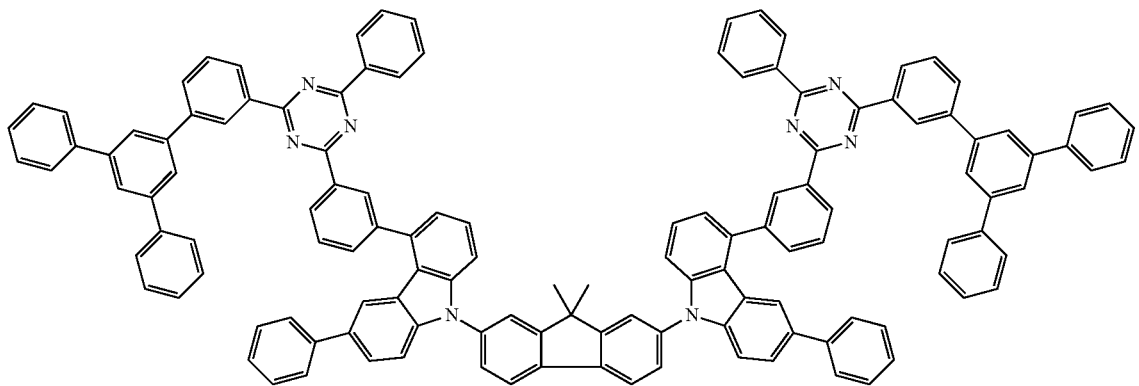

-continued
1-101
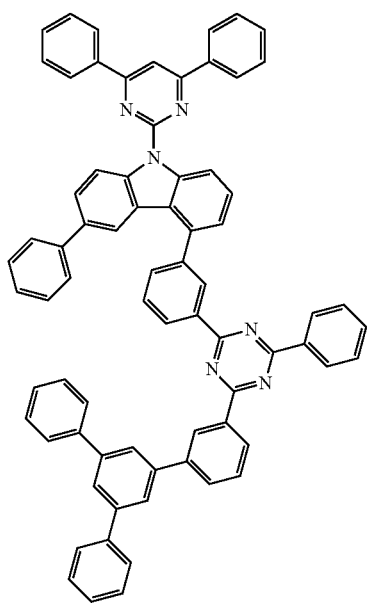
1-102
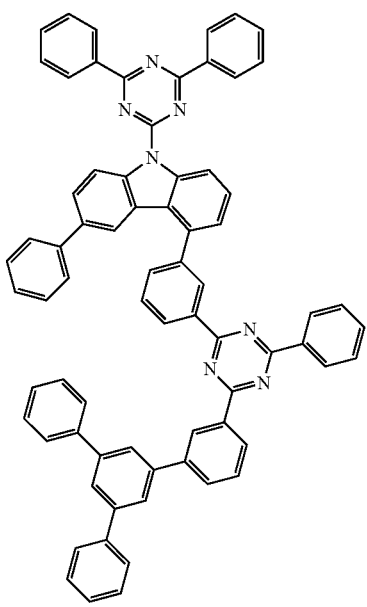
1-103
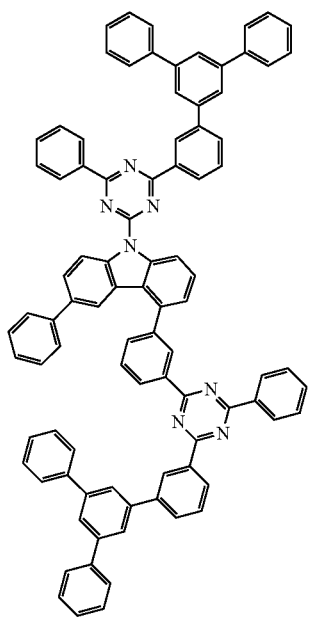
1-104
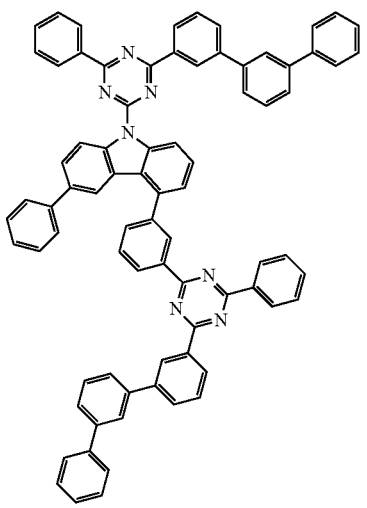

-continued
1-105
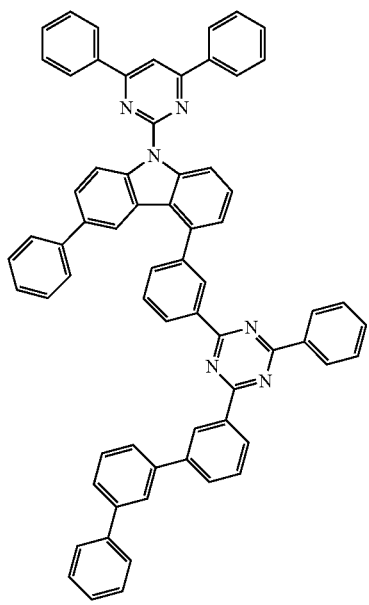
1-106
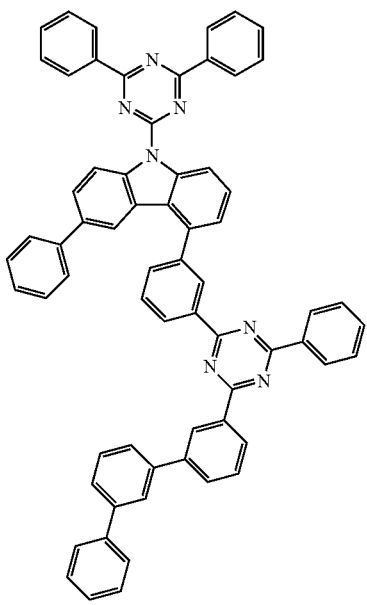
1-107
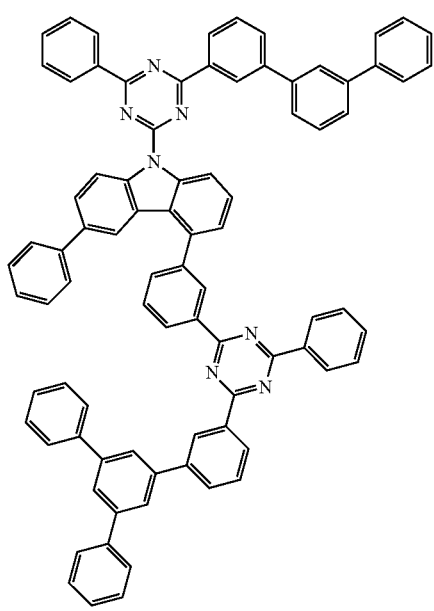
1-108
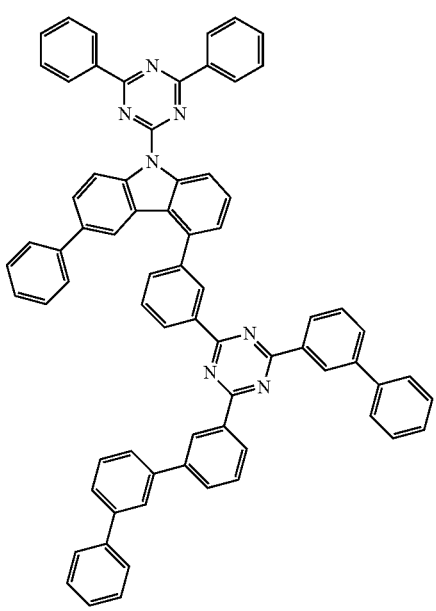

1-109
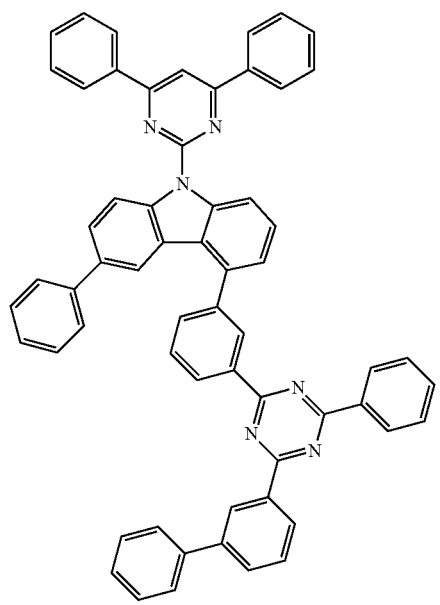
1-110
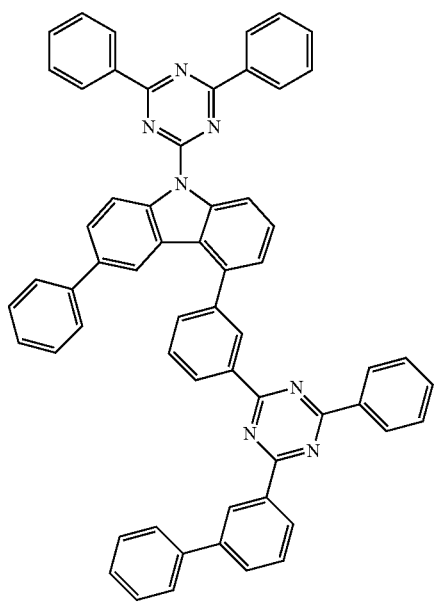
1-111
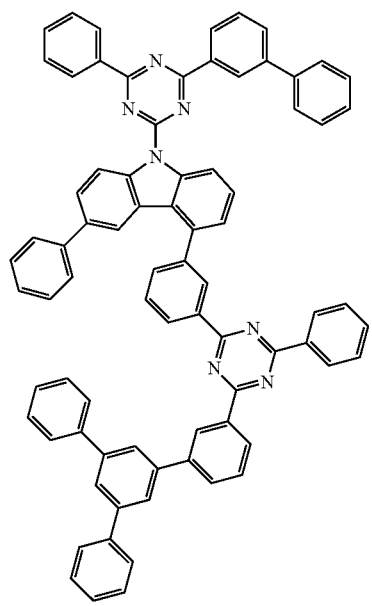
1-112
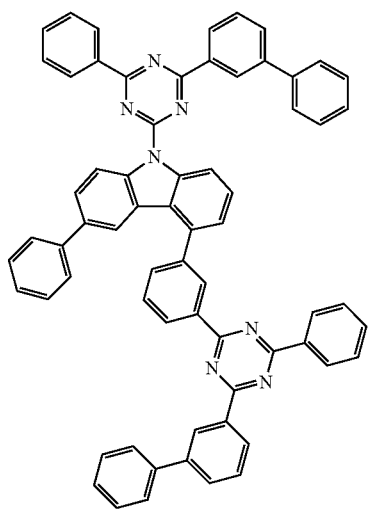

-continued
1-113
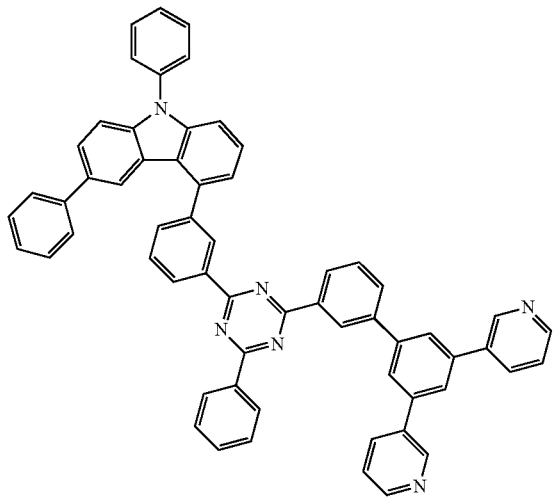
1-114
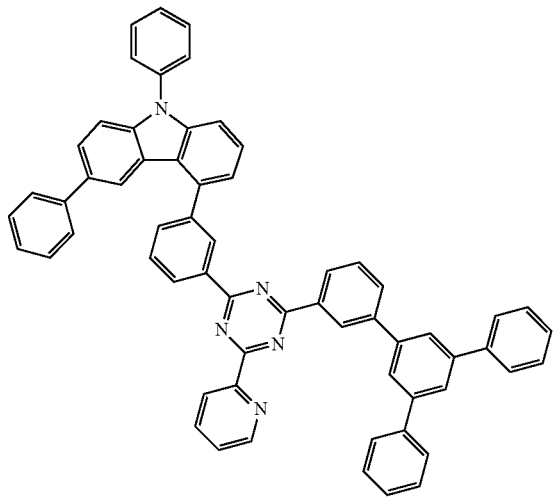
1-115
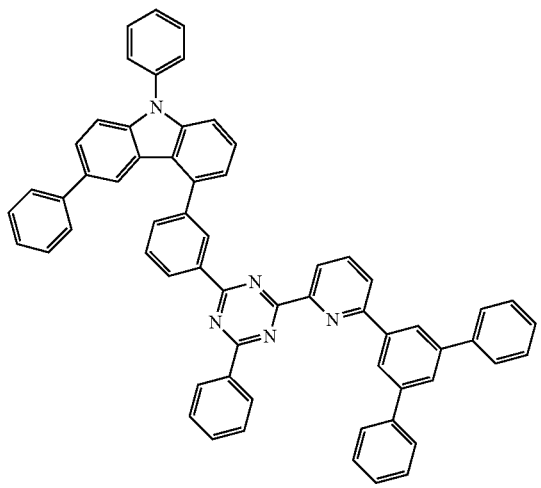
1-116
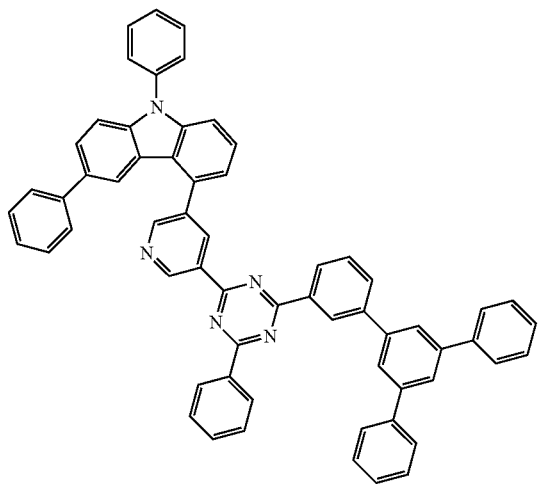
1-117
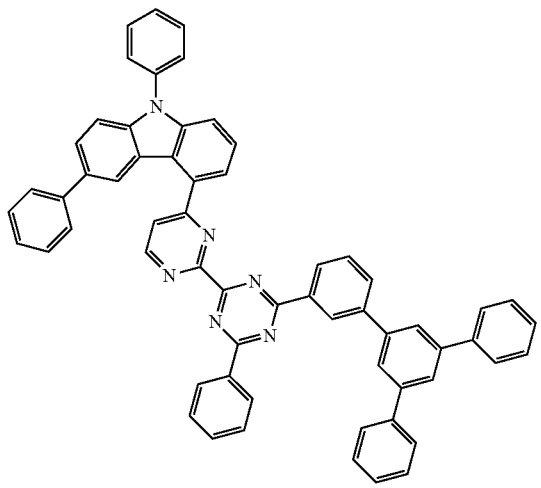
1-118
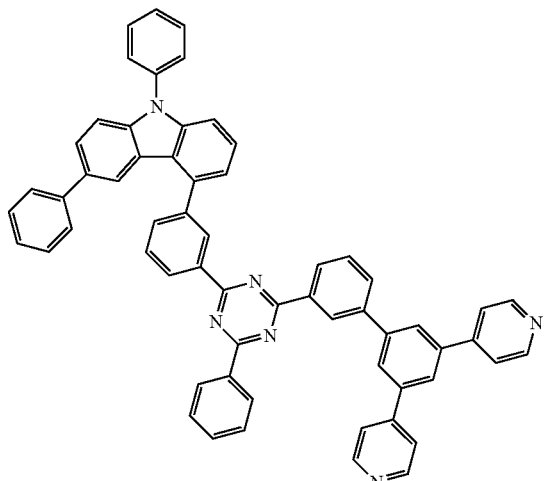

1-119
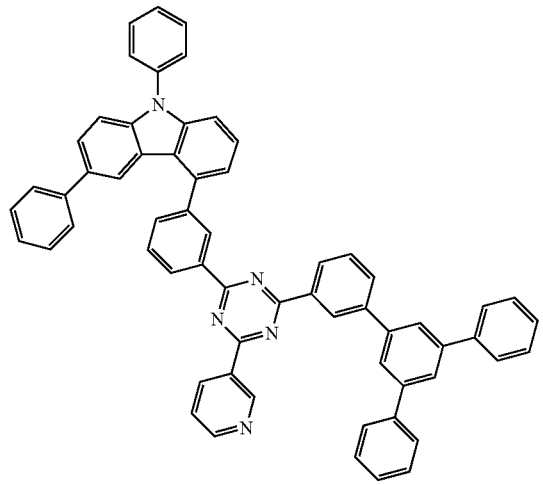
1-120
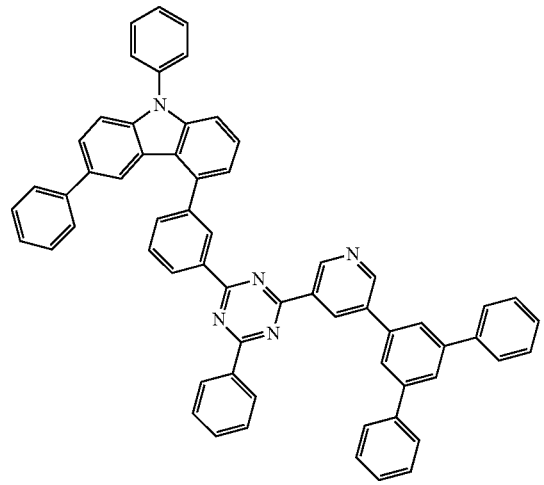
1-121
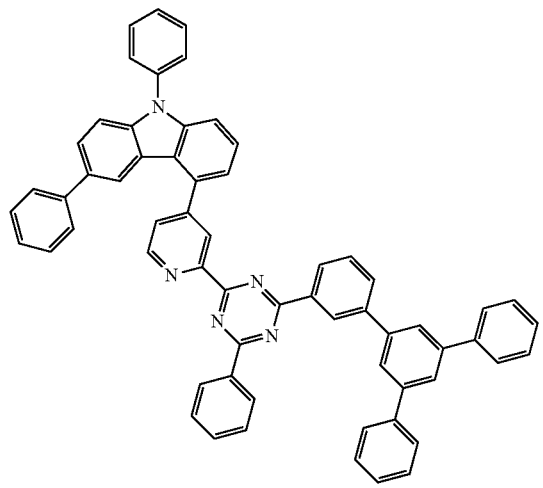
1-122
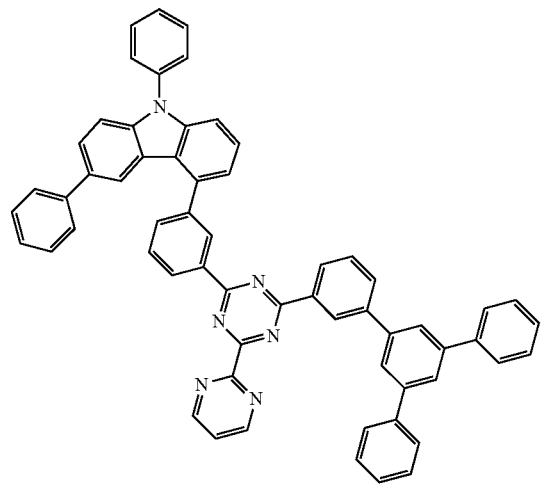
1-123
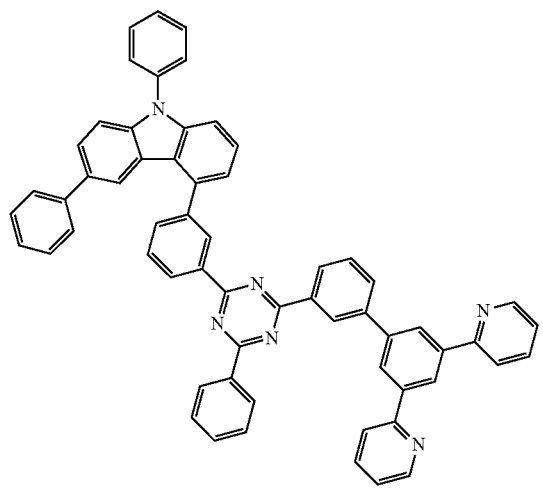
1-124
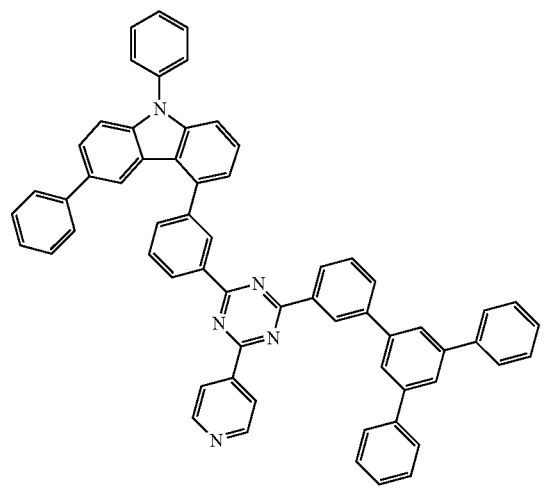

-continued
1-126

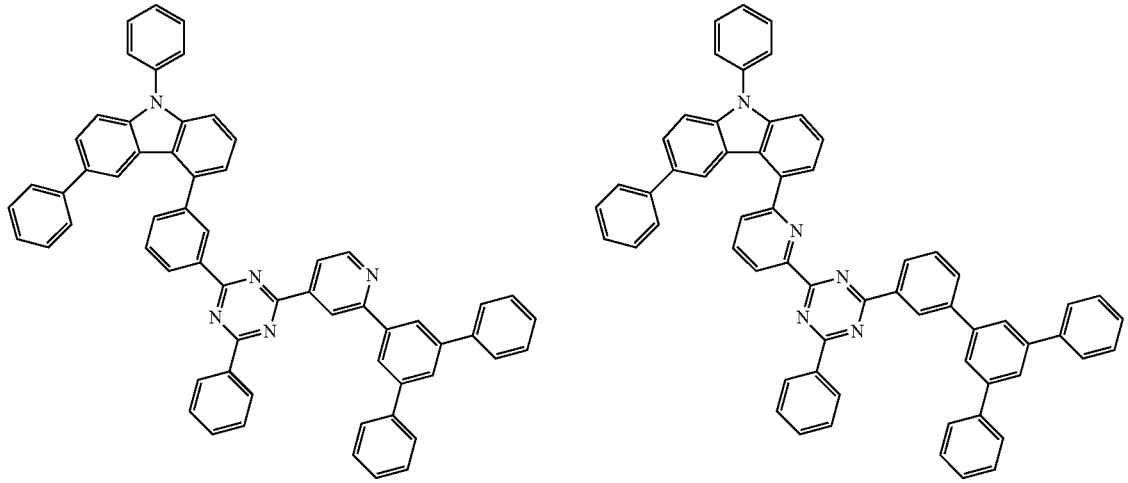

The condensed cyclic compound represented by Formula (1) may have a glass transition temperature of about 120° C. or higher, for example, 125° C. or higher, and for example, 145° C. or higher. The glass transition temperature may be measured by a method defined in JIS K 7121 or ISO 3146 corresponding thereto. In the following examples, the glass transition temperature was measured by a scanning calorimetric measurement method.

In the condensed cyclic compound represented by Formula (1), a solubility to toluene or xylene at 1 atm and 25° C. may be 1.0 wt % or more, for example, 2.0 wt % or more, and for example, 3.0 wt % or more.

An organic light-emitting device including the condensed cyclic compound represented by Formula (1) may have an improved light emission lifespan. Also, when a film including the condensed cyclic compound is formed by solution coating using a composition including the condensed cyclic compound represented by Formula (1), the film may have a uniform thickness.

The condensed cyclic compound may be synthesized using a known organic synthesis method. More specific synthesis methods may be understood in connection with the following examples by those of ordinary skill in the art.

2. Material for Forming Organic Light-Emitting Device

In one or more embodiments, the material for forming the organic light-emitting device includes the condensed cyclic compound represented by Formula (1). The condensed cyclic compound is applicable as the material for forming the organic light-emitting device. Also, since the condensed cyclic compound has electron transport and injection capabilities, the condensed cyclic compound may be used as materials for forming the electron transport layer, the electron injection layer, and the emission layer.

When the material for forming the organic light-emitting device is a material for forming the emission layer, the condensed cyclic compound represented by Formula (1), which is included in the material for forming the emission layer, may be a host material. In this case, the material for forming the emission layer may include only one condensed cyclic compound represented by Formula (1), or may include two or more different condensed cyclic compounds represented by Formula (1). Various modifications may be made to the material for forming the emission layer. For example, the material for forming the emission layer may include i) only Compound 1-7 as the condensed cyclic compound represented by Formula (1) or ii) a mixture of Compounds 1-5 and 1-7 as the condensed cyclic compound represented by Formula (1). In this regard, the material for forming the organic light-emitting device may further include a hole transport compound.

For use as the hole transport compound, a known hole injection material, a known hole transport material, or a known host material may be used. For example, a carbazole-containing compound or a bicarbazole-containing compound may be used. A linking position between two carbazole groups in the bicarbazole-containing compound may be variously changed to, for example, 3, 4-, 3, 3-, 3, 2-, 3, 1-, 2, or 2-.

For example, the hole transport compound may be a compound represented by Formula (6):

Formula (6)

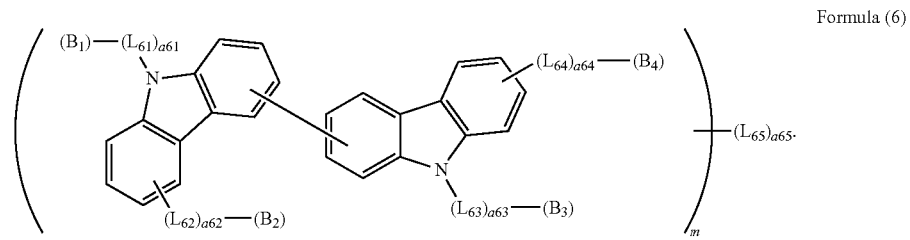

In one or more embodiments, the hole transport compound may be a compound represented by Formula (6)-1:

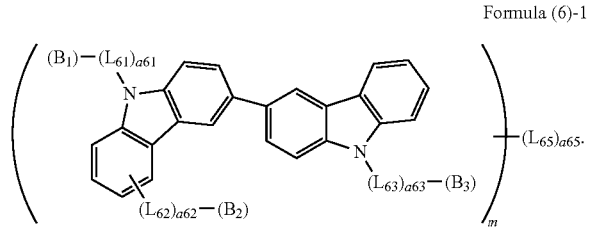

Formula (6)-1

In Formulae (6) and (6)-1, $L_{61}$ to $L_{65}$ may each independently be selected from a single bond, *—C(=O)—*', *—C(=S)—*', *—O—*', *—S—*', *—N($R_{65}$)—', a substituted or unsubstituted $C_2$-$C_{60}$ alkylene group, a substituted or unsubstituted $C_3$-$C_{10}$ cycloalkylene group, a substituted or unsubstituted π electron-depleted nitrogen-free $C_1$-$C_{10}$ heterocycloalkylene group, a substituted or unsubstituted $C_3$-$C_{10}$ cycloalkenylene group, a substituted or unsubstituted π electron-depleted nitrogen-free $C_1$-$C_{10}$ heterocycloalkenylene group, a substituted or unsubstituted $C_6$-$C_{60}$ arylene group, a substituted or unsubstituted π electron-depleted nitrogen-free $C_1$-$C_{60}$ heteroarylene group, a substituted or unsubstituted divalent non-aromatic condensed polycyclic group, and a substituted or unsubstituted divalent π electron-depleted nitrogen-free non-aromatic condensed heteropolycyclic group,

* and *' each indicate a binding site to a neighboring atom, a61 to a65 may each independently be an integer from 1 to 10, $(L_{65})_{a65}$ may be an m-valent linking group or a single bond, wherein m may be a natural number greater than or equal to one, when m is one, $(L_{65})_{a65}$ may not exist, when m is two or more, at least one of groups represented by *-$(L_{61})_{a61}$-$(B_1)$, *-$(L_{62})_{a62}$-$(B_2)$, *-$(L_{63})_{a63}$-$(B_3)$, and *-$(L_{64})_{a64}$-$(B_4)$ may be linked to $(L_{65})_{a65}$, or may be a single bond linked to $(L_{65})_{a65}$, i) $B_1$ to $B_4$ and $R_{65}$ may each independently be linked to $(L_{65})_{a65}$, ii) $B_1$ to $B_4$ and $R_{65}$ may each independently be a single bond linked to $(L_{65})_{a65}$, or iii) $B_1$ to $B_4$ and $R_{65}$ may each independently be selected from hydrogen, deuterium, a substituted or unsubstituted $C_1$-$C_{60}$ alkyl group, a substituted or unsubstituted $C_1$-$C_{60}$ alkoxy group, a substituted or unsubstituted $C_3$-$C_{10}$ cycloalkyl group, a substituted or unsubstituted π electron-depleted nitrogen-free $C_1$-$C_{10}$ heterocycloalkyl group, a substituted or unsubstituted $C_3$-$C_{10}$ cycloalkenyl group, a substituted or unsubstituted π electron-depleted nitrogen-free $C_1$-$C_{10}$ heterocycloalkenyl group, a substituted or unsubstituted $C_6$-$C_{60}$ aryl group, a substituted or unsubstituted π electron-depleted nitrogen-free $C_1$-$C_{60}$ heteroaryl group, a substituted or unsubstituted monovalent non-aromatic condensed polycyclic group, a substituted or unsubstituted π electron-depleted nitrogen-free monovalent non-aromatic condensed heteropolycyclic group, —Si($Q_1$)($Q_2$)($Q_3$), —N($Q_1$)($Q_2$), and —C(=O)($Q_1$), provided that $B_1$ and $B_2$ are not hydrogen, deuterium, a substituted or unsubstituted $C_1$-$C_{60}$ alkyl group, or a substituted or unsubstituted $C_1$-$C_{60}$ alkoxy group, and at least one substituent of the substituted $C_2$-$C_{60}$ alkylene group, the substituted $C_3$-$C_{10}$ cycloalkylene group, the substituted π electron-depleted nitrogen-free $C_1$-$C_{10}$ heterocycloalkylene group, the substituted $C_3$-$C_{10}$ cycloalkenylene group, the substituted π electron-depleted nitrogen-free $C_1$-$C_{10}$ heterocycloalkenylene group, the substituted $C_6$-$C_{60}$ arylene group, the substituted π electron-depleted nitrogen-free $C_1$-$C_{60}$ heteroarylene group, the substituted divalent non-aromatic condensed polycyclic group, the substituted divalent π electron-depleted nitrogen-free non-aromatic condensed heteropolycyclic group, the substituted $C_1$-$C_{60}$ alkyl group, the substituted $C_1$-$C_{60}$ alkoxy group, the substituted $C_3$-$C_{10}$ cycloalkyl group, the substituted π electron-depleted nitrogen-free $C_1$-$C_{10}$ heterocycloalkyl group, the substituted $C_3$-$C_{10}$ cycloalkenyl group, the substituted π electron-depleted nitrogen-free $C_1$-$C_{10}$ heterocycloalkenyl group, the substituted $C_6$-$C_{60}$ aryl group, the substituted π electron-depleted nitrogen-free $C_1$-$C_{60}$ heteroaryl group, the substituted monovalent non-aromatic condensed polycyclic group, and the substituted π electron-depleted nitrogen-free monovalent non-aromatic condensed heteropolycyclic group may be selected from:

deuterium and a $C_1$-$C_{60}$ alkyl group;

a $C_3$-$C_{10}$ cycloalkyl group, a π electron-depleted nitrogen-free $C_1$-$C_{10}$ heterocycloalkyl group, a $C_3$-$C_{10}$ cycloalkenyl group, a π electron-depleted nitrogen-free $C_1$-$C_{10}$ heterocycloalkenyl group, a $C_6$-$C_{60}$ aryl group, a π electron-depleted nitrogen-free $C_1$-$C_{60}$ heteroaryl group, a monovalent non-aromatic condensed polycyclic group, and a π electron-depleted nitrogen-free monovalent non-aromatic condensed heteropolycyclic group;

a $C_3$-$C_{10}$ cycloalkyl group, a π electron-depleted nitrogen-free $C_1$-$C_{10}$ heterocycloalkyl group, a $C_3$-$C_{10}$ cycloalkenyl group, a π electron-depleted nitrogen-free $C_1$-$C_{10}$ heterocycloalkenyl group, a $C_6$-$C_{60}$ aryl group, a π electron-depleted nitrogen-free $C_1$-$C_{60}$ heteroaryl group, a monovalent non-aromatic condensed polycyclic group, and a π electron-depleted nitrogen-free monovalent non-aromatic condensed heteropolycyclic group, each substituted with at least one selected from deuterium, a $C_1$-$C_{60}$ alkyl group, a $C_3$-$C_{10}$ cycloalkyl group, a π electron-depleted nitrogen-free $C_1$-$C_{10}$ heterocycloalkyl group, a $C_3$-$C_{10}$ cycloalkenyl group, a π electron-depleted nitrogen-free $C_1$-$C_{10}$ heterocycloalkenyl group, a $C_6$-$C_{60}$ aryl group, a π electron-depleted nitrogen-free $C_1$-$C_{60}$ heteroaryl group, a monovalent non-aromatic condensed polycyclic group, a π electron-depleted nitrogen-free monovalent non-aromatic condensed heteropolycyclic group, —Si($Q_{21}$)($Q_{22}$)($Q_{23}$), —N($Q_{21}$)($Q_{22}$), and —C(=P) ($Q_{21}$); and —Si($Q_{31}$)($Q_{32}$)($Q_{33}$), —N($Q_{31}$)($Q_{32}$), and —C(=O) ($Q_{31}$), wherein $Q_1$ to $Q_3$, $Q_{21}$ to $Q_{23}$, and $Q_{31}$ to $Q_{33}$ may each independently be selected from a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, and a diphenyldibenzothiophenyl group.

In one or more embodiments, all of $B_1$ to $B_3$ in Formulae (6) and (6)-1 may not be hydrogen, deuterium, a substituted or unsubstituted $C_1$-$C_{60}$ alkyl group, or a substituted or unsubstituted $C_1$-$C_{60}$ alkoxy group.

In one or more embodiments, all of $B_1$ to $B_4$ in Formula (6) may not be hydrogen, deuterium, a substituted or unsubstituted $C_1$-$C_{60}$ alkyl group, or a substituted or unsubstituted $C_1$-$C_{60}$ alkoxy group.

For example, $L_{61}$ to $L_{65}$ in Formulae (6) and (6)-1 may each independently be selected from:

a single bond, *—C(=O)—*', *—C(=S)—*', and *—N($R_{65}$)—*'; and a phenylene group, an indenylene group, a naphthylene group, an acenaphthylene group, a fluorenylene group, a spiro-bifluorenylene group, a phenanthrenylene group, an anthracenylene group, a fluoranthrenylene group, a triphenylenylene group, a pyrenylene group, a chrysenylene group, a pyrrolylene group, a furanylene group, a thienylene group, an isoindolylene group, an indolylene group, a benzofuranylene group, a benzothiophenylene group, a carbazolylene group, a dibenzofuranylene group, a dibenzothiophenylene group, a benzocarbazolylene group, a naphthobenzofuranylene group, and a naphthobenzothiophenylene group, each unsubstituted or substituted with at least one selected from deuterium, -$CD_3$, -$CD_2H$, -$CDH_2$, a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group, and $Ar_{62}$ are each independently the same as described in connection with $L_{65}$ in Formula (6), provided that $Ar_{61}$ and $Ar_{62}$ are not a single bond, *—C(=O)—*', *—C(=S)—*', *—O—*', *—S—*', or *—N($R_{65}$)—*', but embodiments of the present disclosure are not limited thereto.

In one or more embodiments, i) $B_1$ to $B_3$ and $R_{65}$ in Formulae (6) and (6)-1 may each independently be linked to $(L_{65})_{a65}$, ii) $B_1$ to $B_3$ and $R_{65}$ in Formulae (6) and (6)-1 may each independently be a single bond, or iii) $B_1$ to $B_3$ and $R_{65}$ in Formulae (6) and (6)-1 may each independently be selected from a phenyl group, an indenyl group, a naphthyl group, an acenaphthyl group, a fluorenyl group, a spiro-bifluorenyl group, a phenanthrenyl group, an anthracenyl group, a fluoranthenyl group, a triphenylenyl group, a pyrenyl group, a chrysenyl group, a pyrrolyl group, a furanyl group, a thienyl group, an isoindolyl group, an indolyl group, a benzofuranyl group, a benzothiophenyl group, a carbazolyl group, a dibenzofuranyl group, a dibenzothiophenyl group, a benzocarbazolyl group, a naphthobenzofuranyl group, and a naphthobenzothiophenyl group, each unsubstituted or substituted with at least one selected from deuterium, -$CD_3$, -$CD_2H$, -$CDH_2$, a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group,

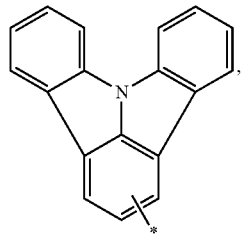 , 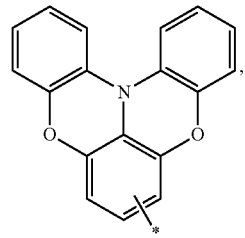 , 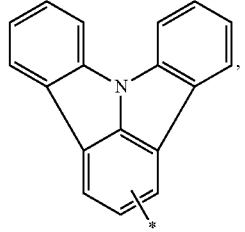 , 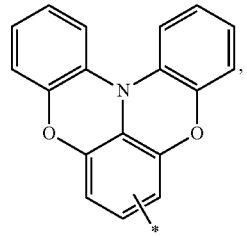 ,

—Si($Q_{31}$)($Q_{32}$)($Q_{33}$), —N($Q_{31}$)($Q_{32}$), and —C(=O)($Q_{31}$).

In one or more embodiments, in Formulae (6) and (6)-1, $L_{61}$ to $L_{64}$ may each independently be selected from a single bond, groups represented by Formulae 6-1 to 6-3, and groups represented by Formulae 6-20 to 6-27, and $L_{65}$ may be selected from a single bond, *—C(=O)—*', *—C(=S)—*', *—N($R_5$)—*', groups represented by Formulae 6-1 to 6-3, and groups represented by Formulae 6-20 to 6-27.

a61, a62, a63, a64, and a65 in Formulae (6) and (6)-1 respectively indicate the number of groups $L_{61}$, the number of groups $L_{62}$, the number of groups $L_{63}$, the number of groups $L_{64}$, and the number of groups $L_{65}$ and may each independently be an integer from 1 to 5 or an integer from 1 to 3, but embodiments of the present disclosure are not limited thereto. When a61 is two or more, two or more groups $L_{61}$ may be identical to or different from each other. This may be equally applied to a62 to a65 and $L_{62}$ to $L_{65}$.

m in Formulae (6) and (6)-1 may be a natural number from 1 to 10. For example, m may be 1, 2, 3, or 4, or m may be 1 or 2, but embodiments of the present disclosure are not limited thereto.

In one or more embodiments, in Formulae (6) and (6)-1, 1) m may be one, or 2) m may be two, $(L_{65})_{a65}$ may be a group represented by *—$Ar_{61}$-$T_{61}$-$Ar_{62}$—*', and $Ar_{61}$, $T_{61}$, —Si($Q_{31}$)($Q_{32}$)($Q_{33}$), —N($Q_{31}$)($Q_{32}$), and —C(=O)($Q_{31}$).

$B_4$ in Formula (6) may be hydrogen, deuterium, or a $C_1$-$C_{20}$ alkyl group, or $B_4$ in Formulae (6) and (6)-1 are the same as described in connection with $B_1$ in Formulae (6) and (6)-1.

In one or more embodiments, i) *-$(L_{61})_{a61}$-$(B_1)$, *-$(L_{62})_{a62}$-$(B_2)$, and *-$(L_{63})_{a63}$-$(B_3)$ in Formulae (6) and (6)-1 may each independently be linked to $(L_{65})_{a65}$, ii) *-$(L_{61})_{a61}$-$(B_1)$, *-$(L_{62})_{a62}$-$(B_2)$, and *-$(L_{63})_{a63}$-$(B_3)$ in Formulae (6) and (6)-1 may each independently be a single bond linked to $(L_{65})_{a65}$, or iii) *-$(L_{61})_{a61}$-$(B_1)$, *-$(L_{62})_{a62}$-$(B_2)$, and *-$(L_{63})_{a63}$-$(B_3)$ in Formulae (6) and (6)-1 may each independently be selected from the group represented by Formulae 7-1 to 7-29 and groups represented by Formulae 8-1 to 8-7:

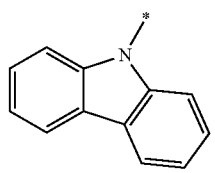

8-1

8-2
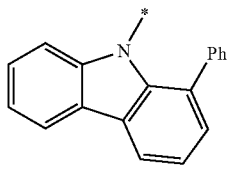

8-3
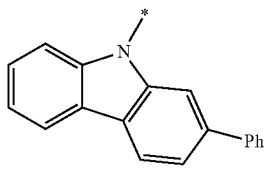

8-4
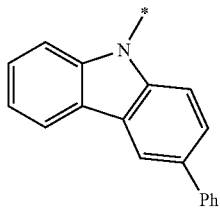

8-5
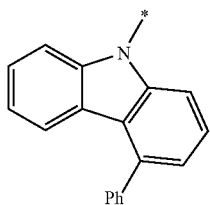

8-6
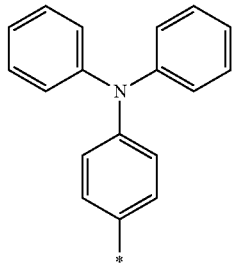

8-7
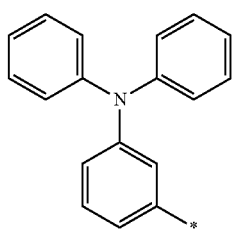

wherein, in Formulae 8-1 to 8-7, Ph indicates a phenyl group and * indicates a binding site to a neighboring atom.

The group represented by *-$(L_{64})_{a64}$-$(B_4)$ in Formula (6) may be hydrogen, deuterium, or a $C_1$-$C_{20}$ alkyl group. In one or more embodiments, the group represented by *-$(L_{64})_{a64}$-$(B_4)$ is the same as described in connection with *-$(L_{61})_{a61}$-$(B_1)$.

A hole transport compound represented by Formula (6) (for example, Formula (6)-1) may not include a π electron-depleted nitrogen-containing cyclic group (for example, a pyridine group, a pyrimidine group, a triazine group, a quinoline group, or the like).

Examples of the hole transport compound represented by Formula (6) (for example, Formula (6)-1) may include Compounds 6-1 to 6-52, but embodiments of the present disclosure are not limited thereto:

6-1
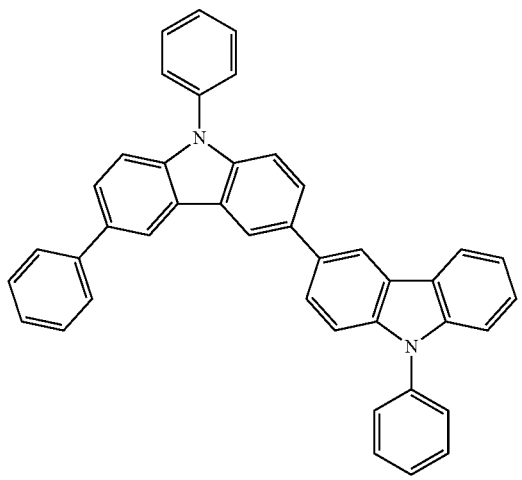

6-2
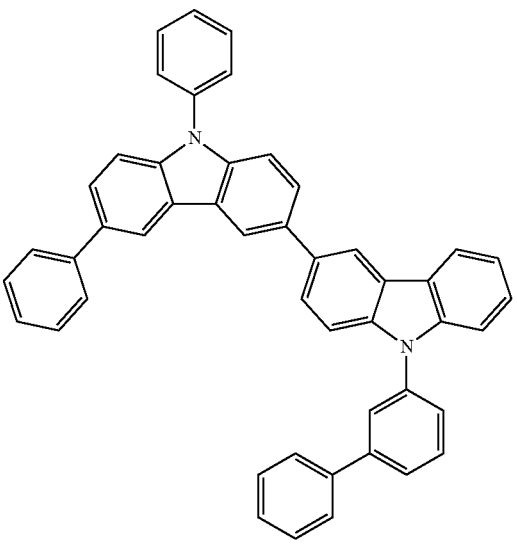

-continued
117
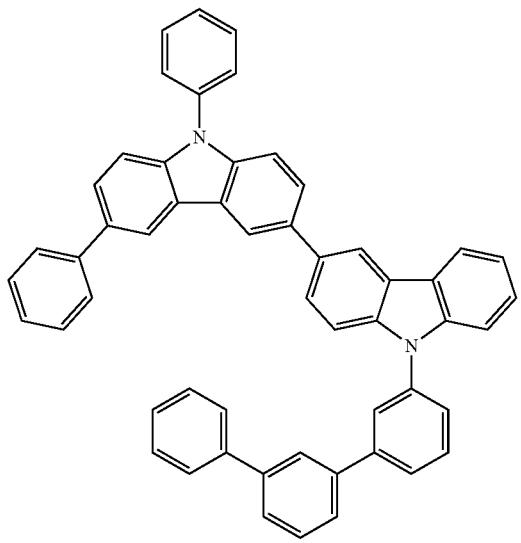
6-3
118
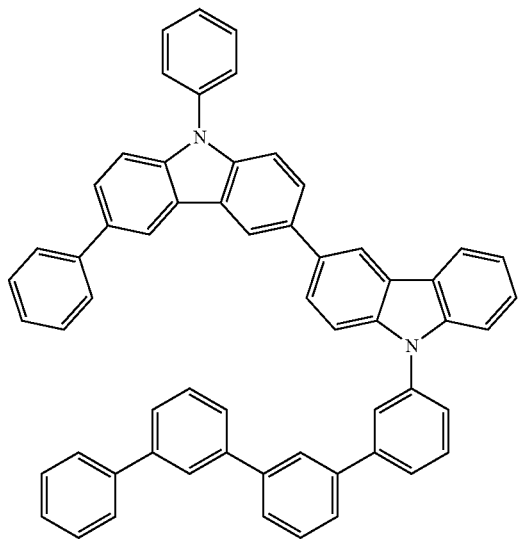
6-4
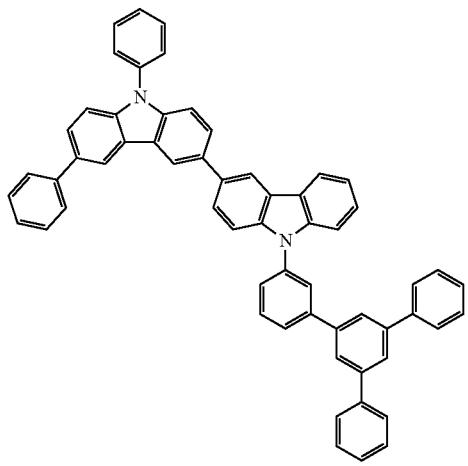
6-5
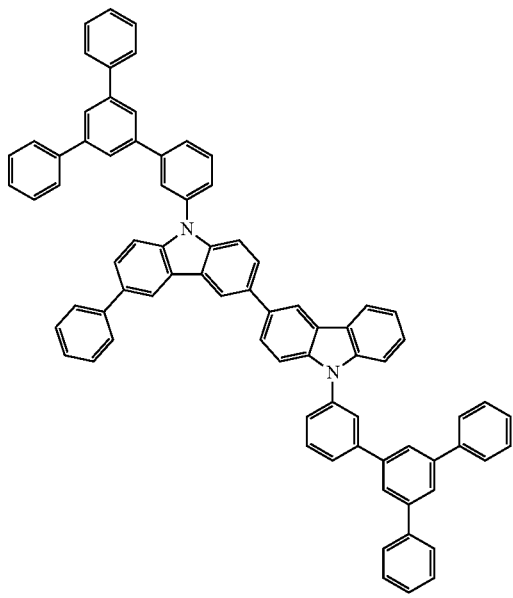
6-6

-continued
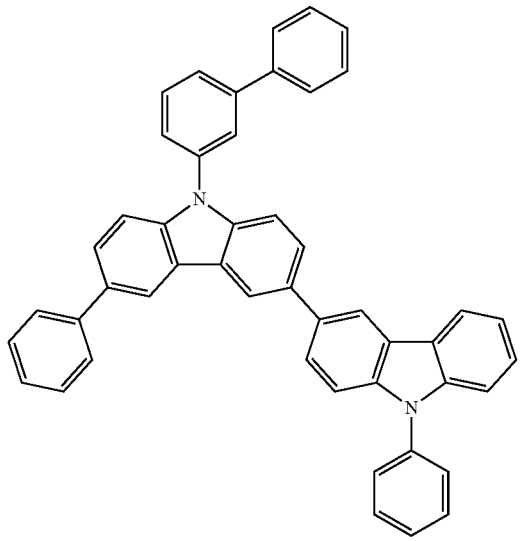
6-7
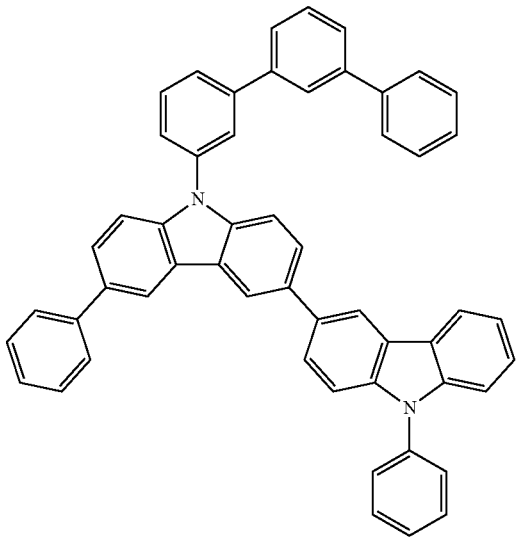
6-8
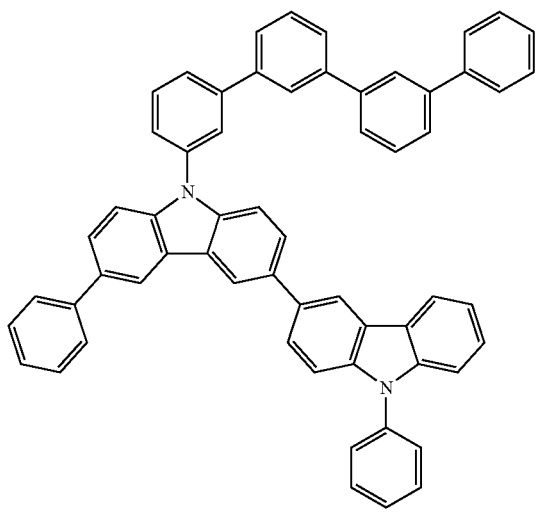
6-9
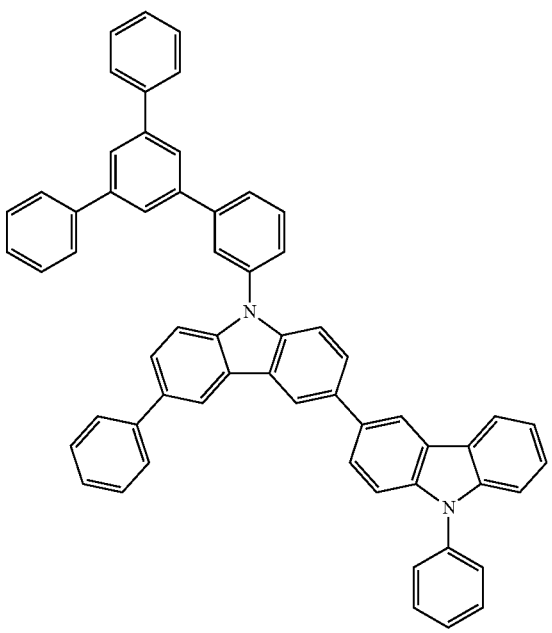
6-10

-continued
6-11
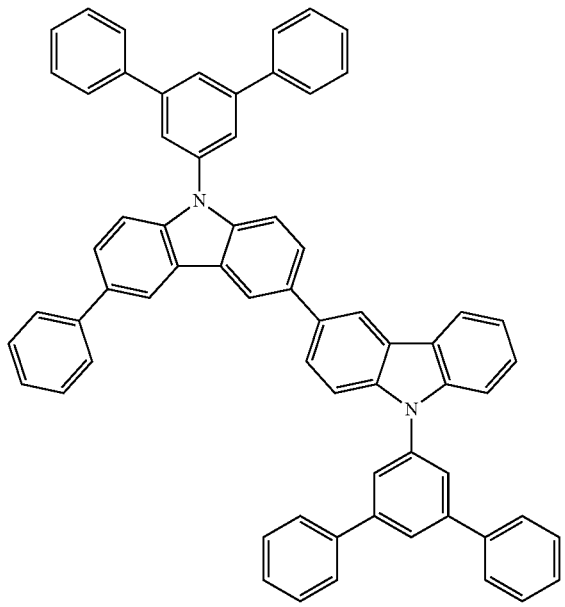
6-12
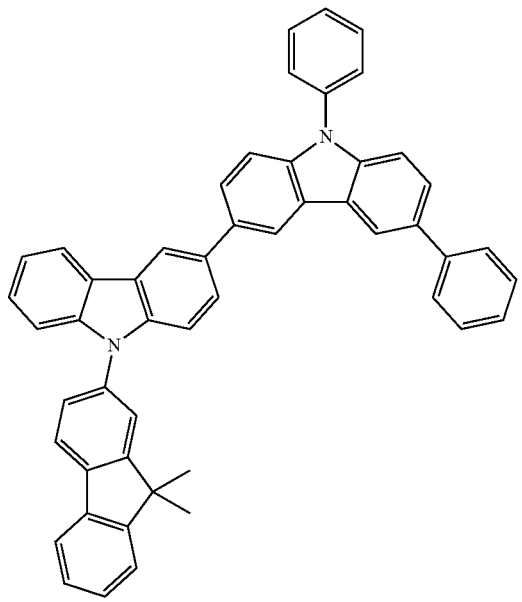
6-13
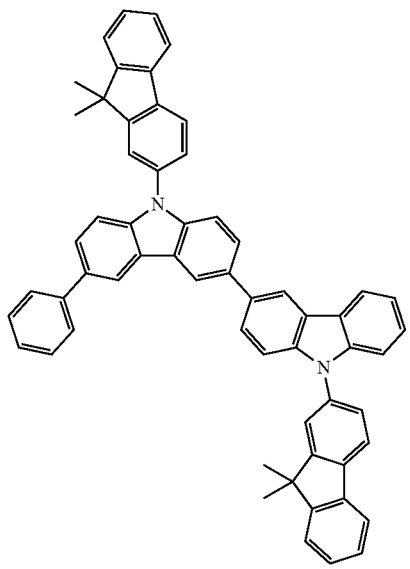
6-14
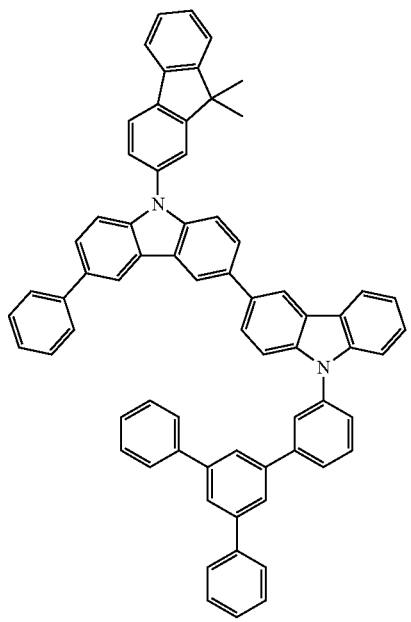

123
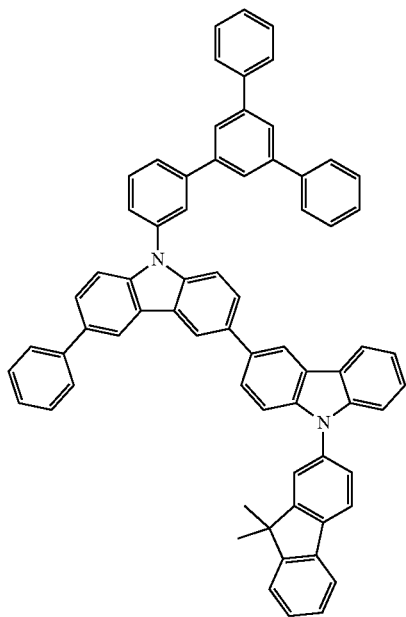
6-15
124
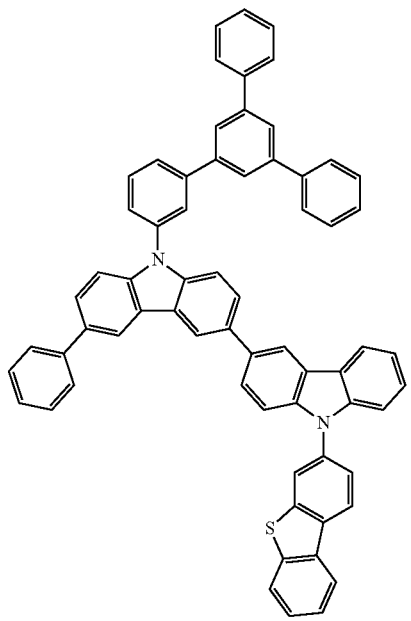
6-16
6-17
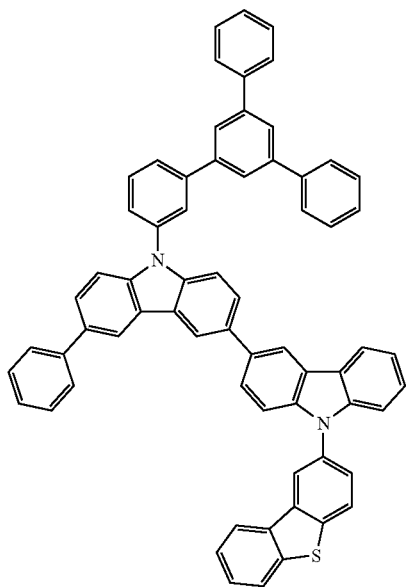
6-18
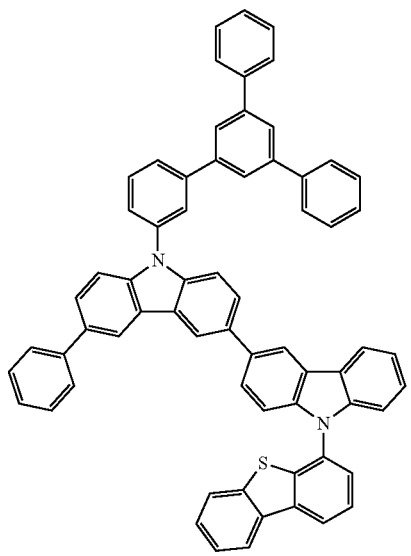

-continued
6-19
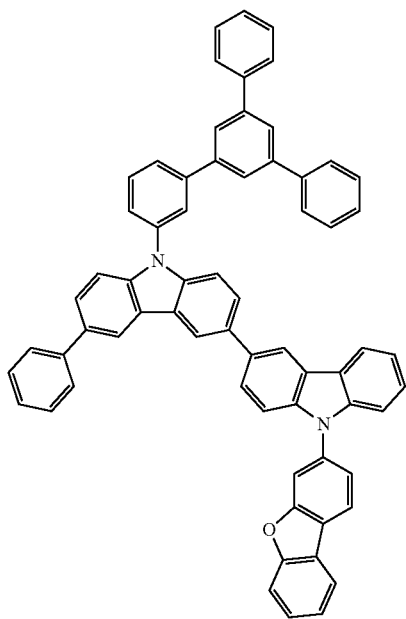
6-20
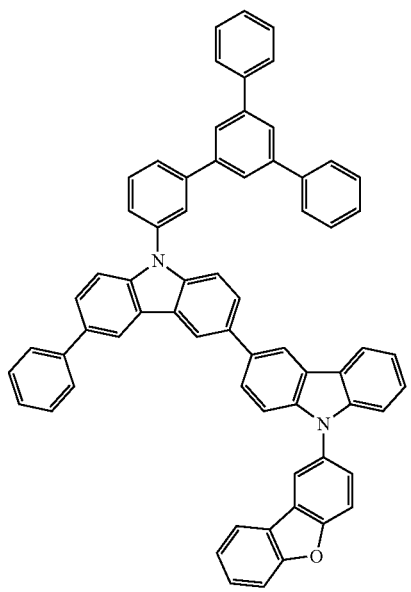
6-21
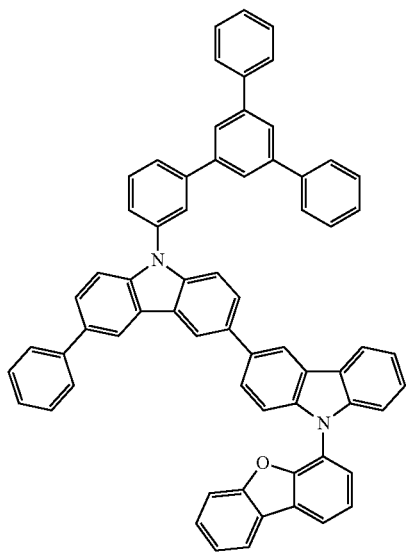
6-22
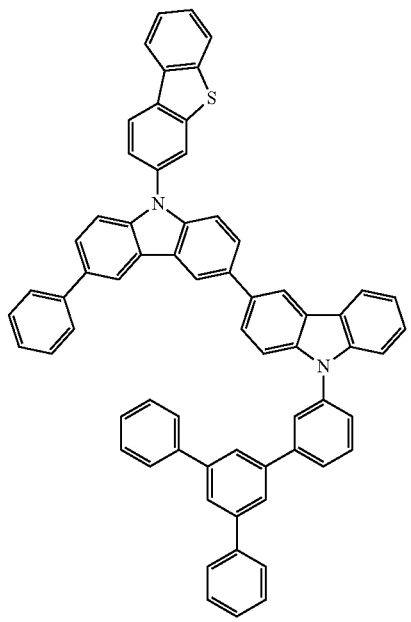

-continued
127
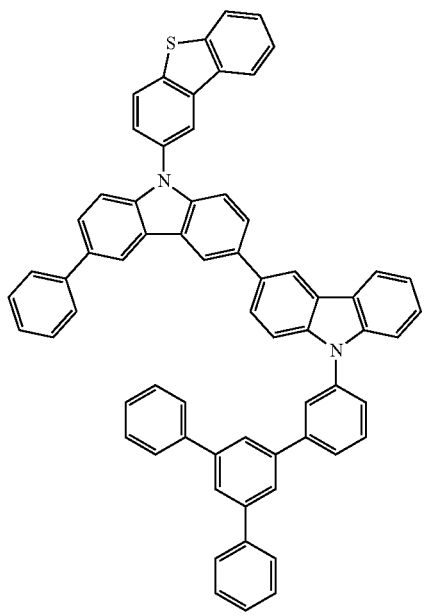
6-23
128
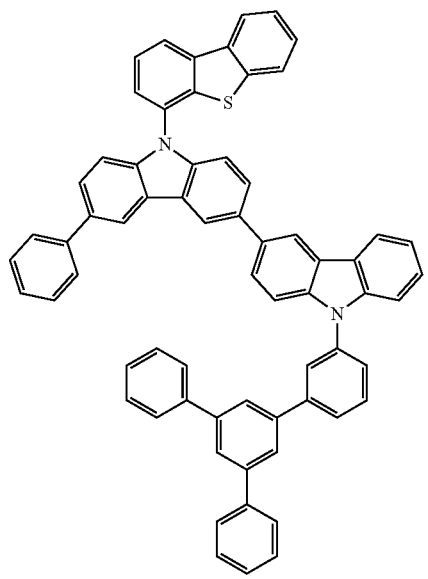
6-24
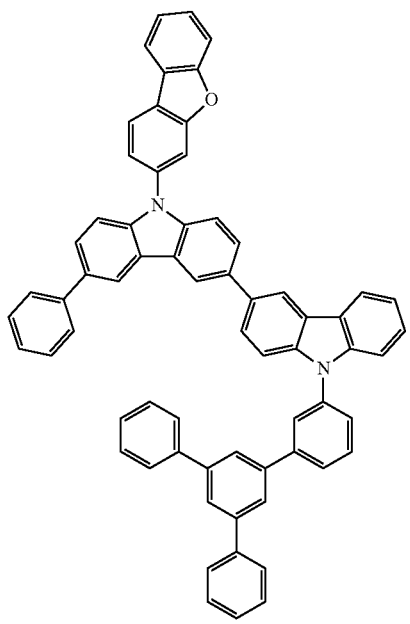
6-25
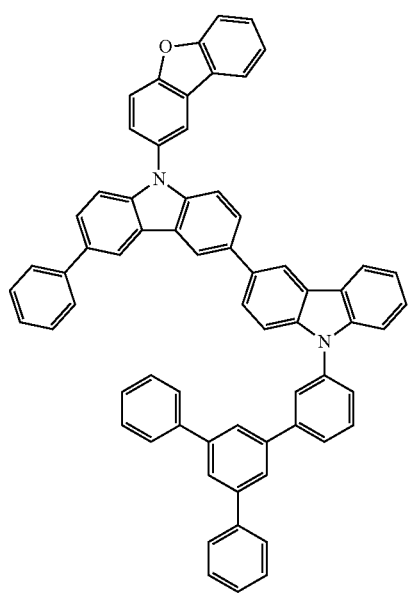
6-26

-continued
6-27
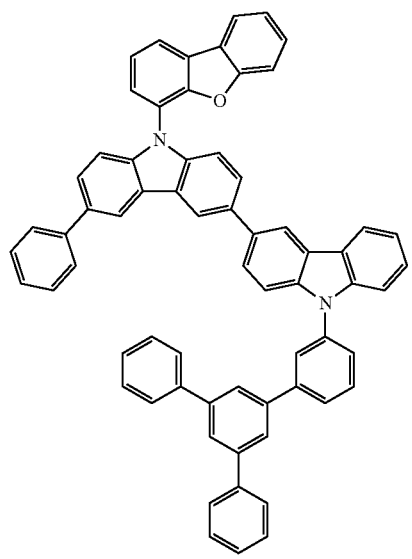
6-28
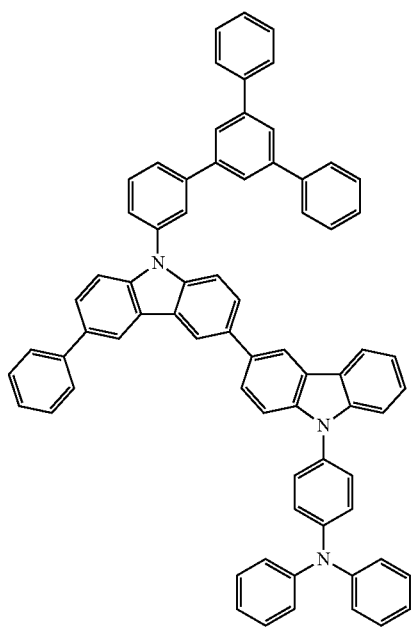
6-29
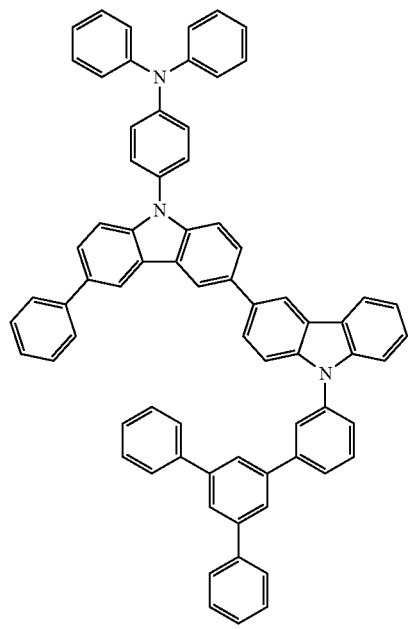
6-30
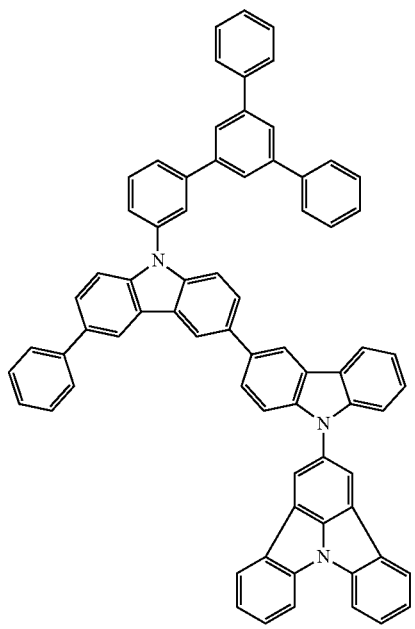

-continued
6-31
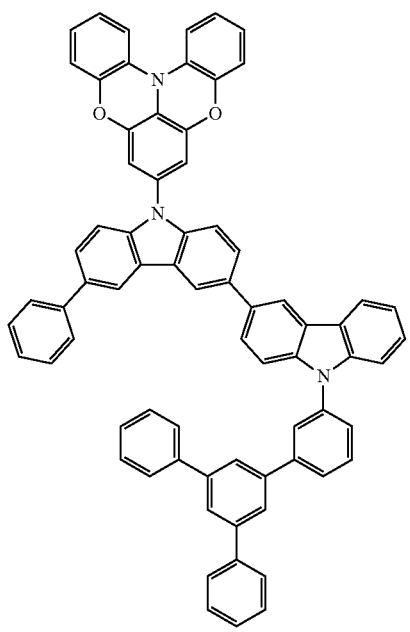
6-32
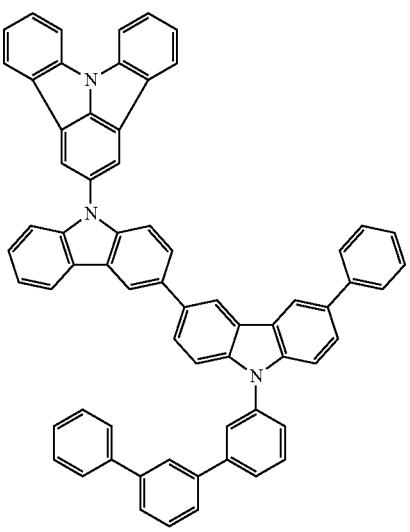
6-33
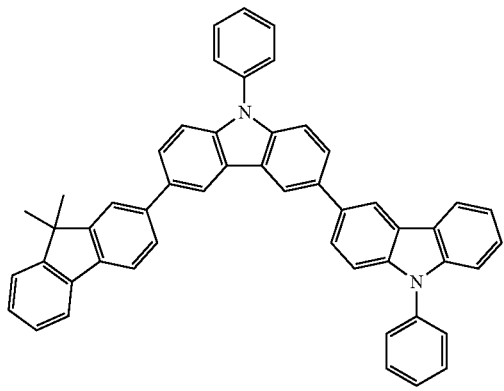
6-34
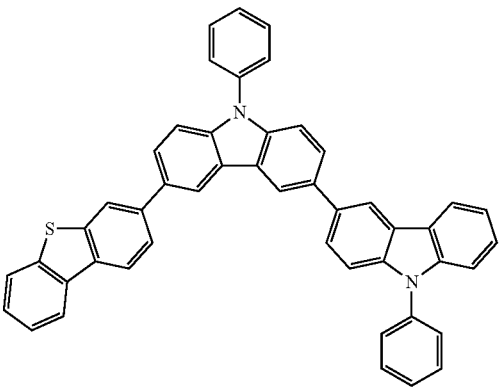
6-35
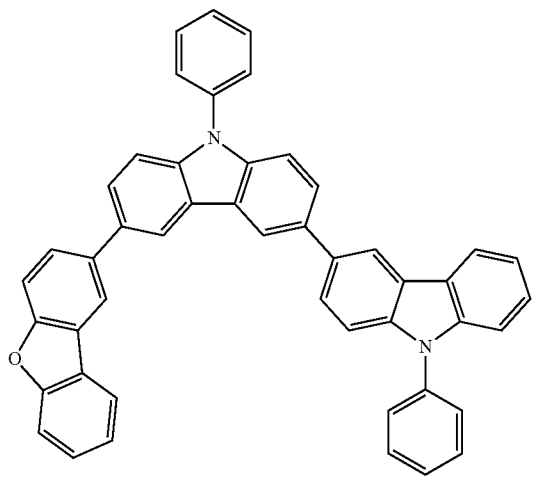
6-36
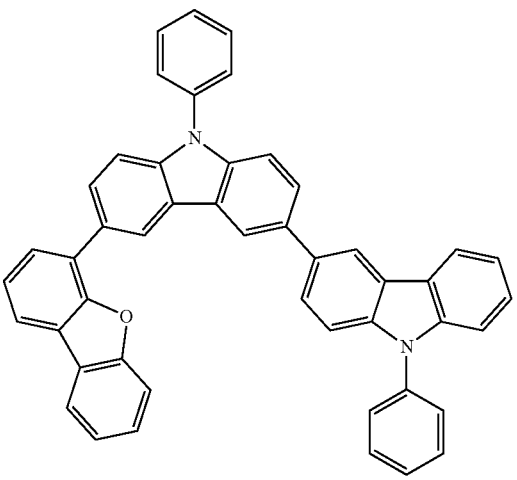

6-37
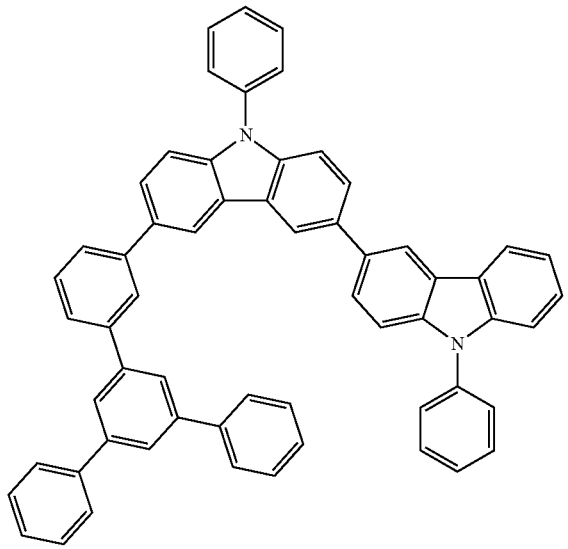
6-38
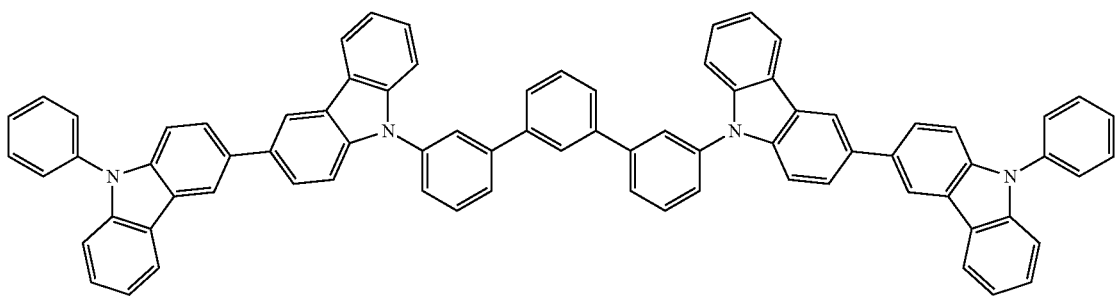
6-39
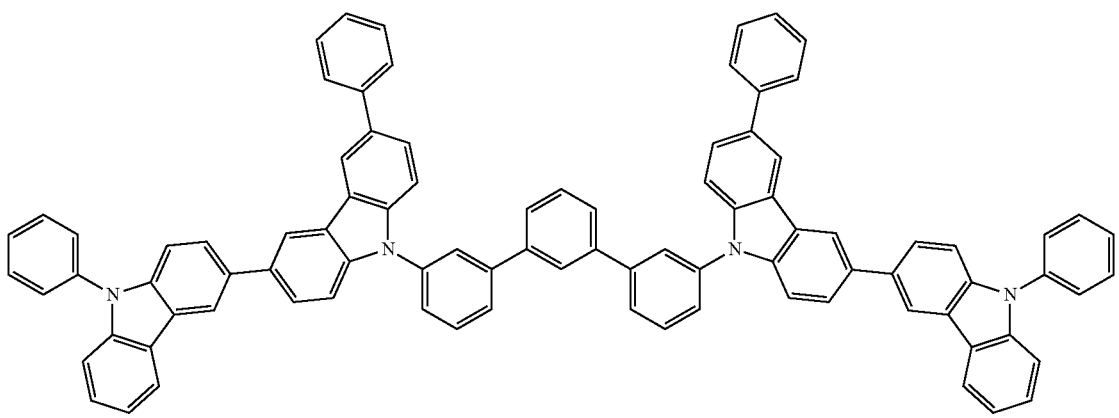

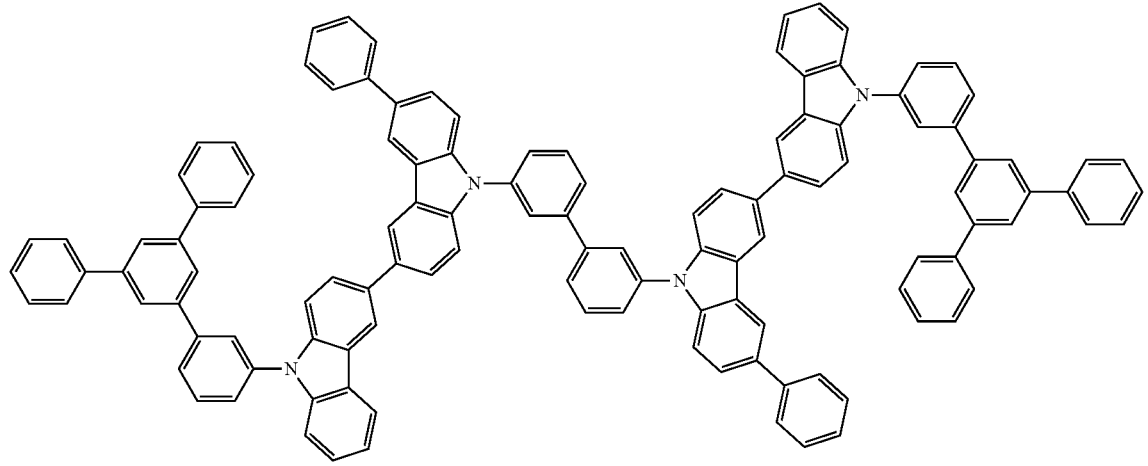
6-40
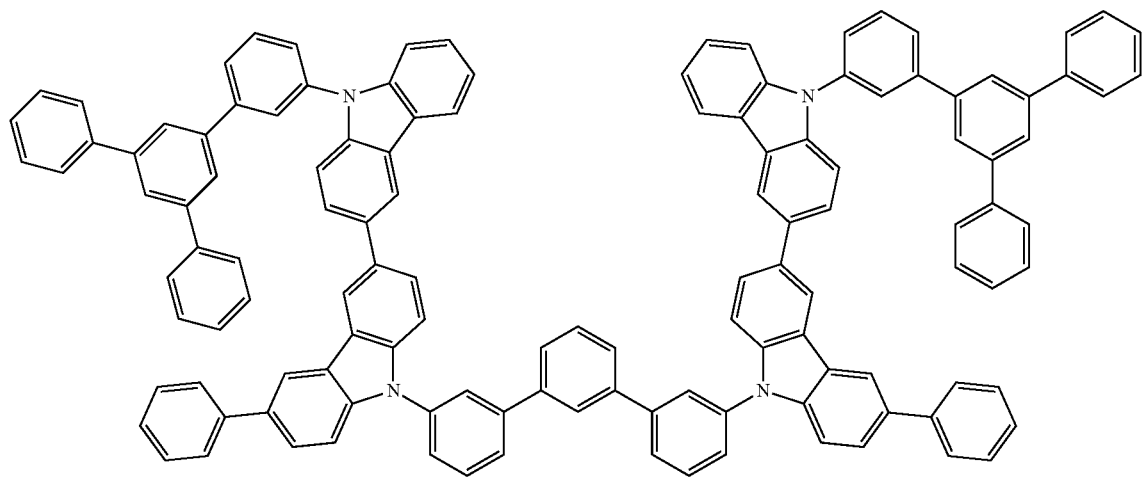
6-41
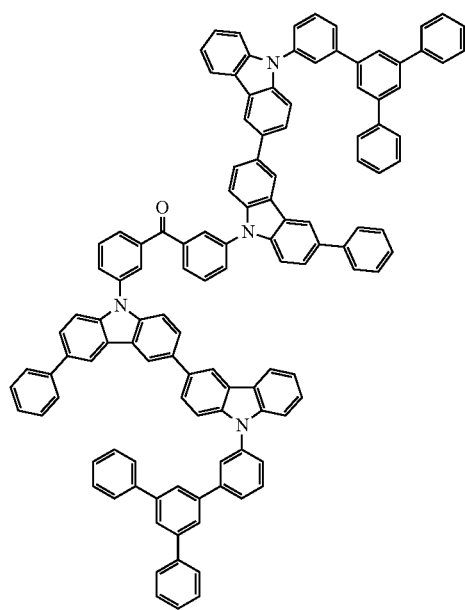
6-42
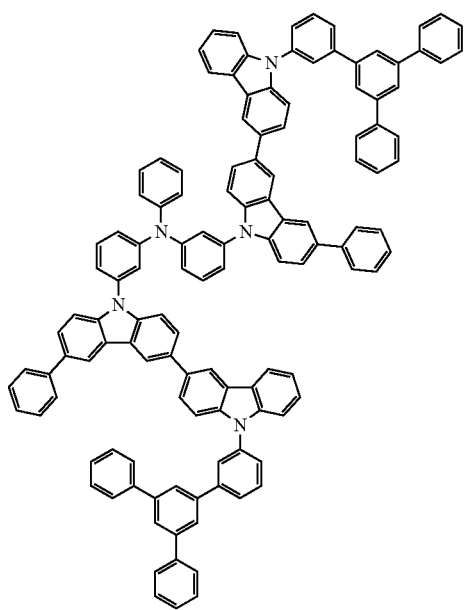
6-43

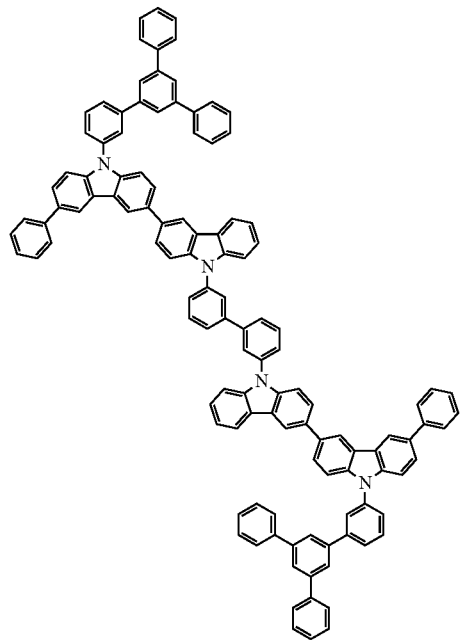
6-44
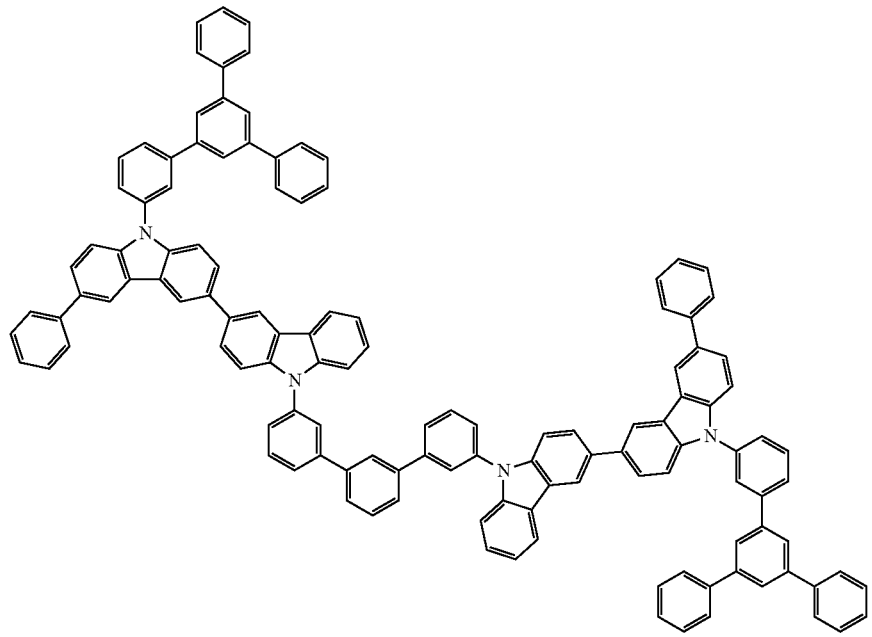
6-45

-continued
6-46
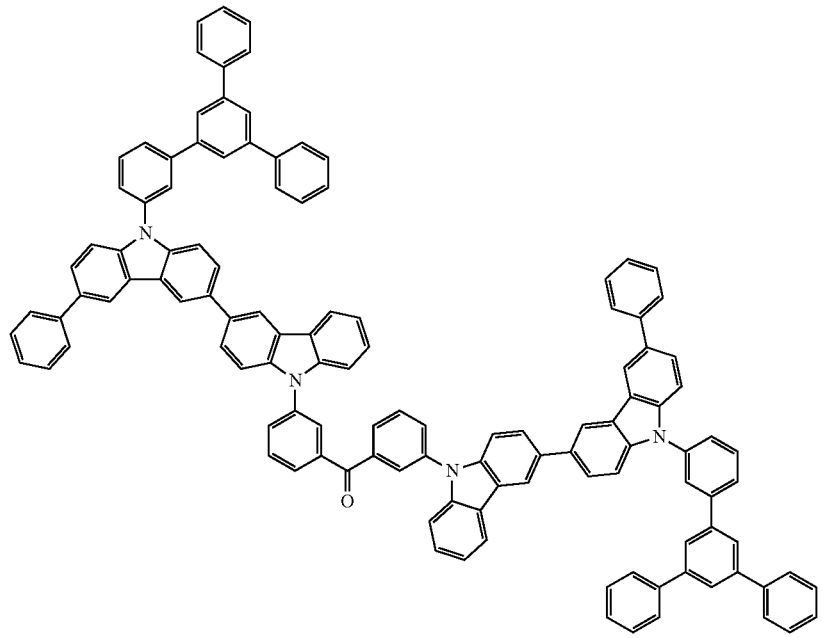
6-47
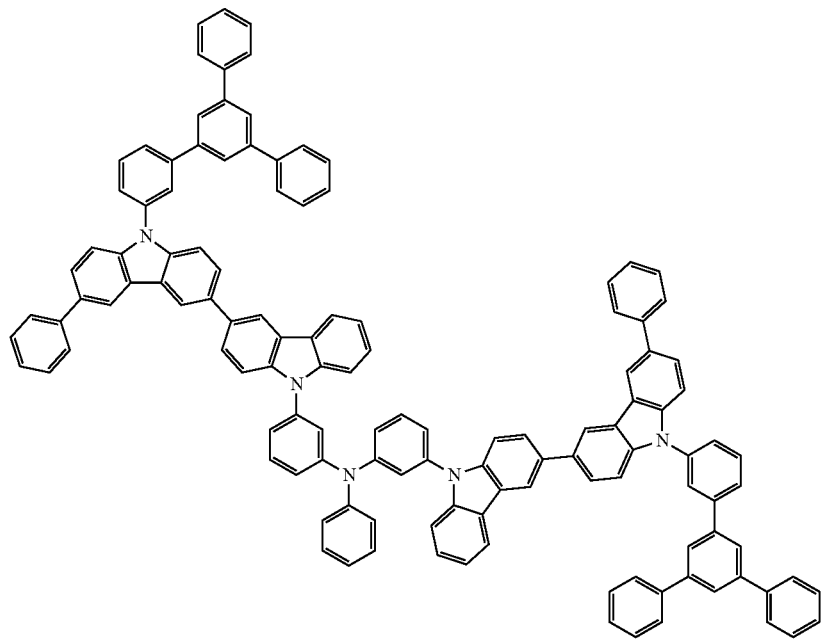

-continued
6-48
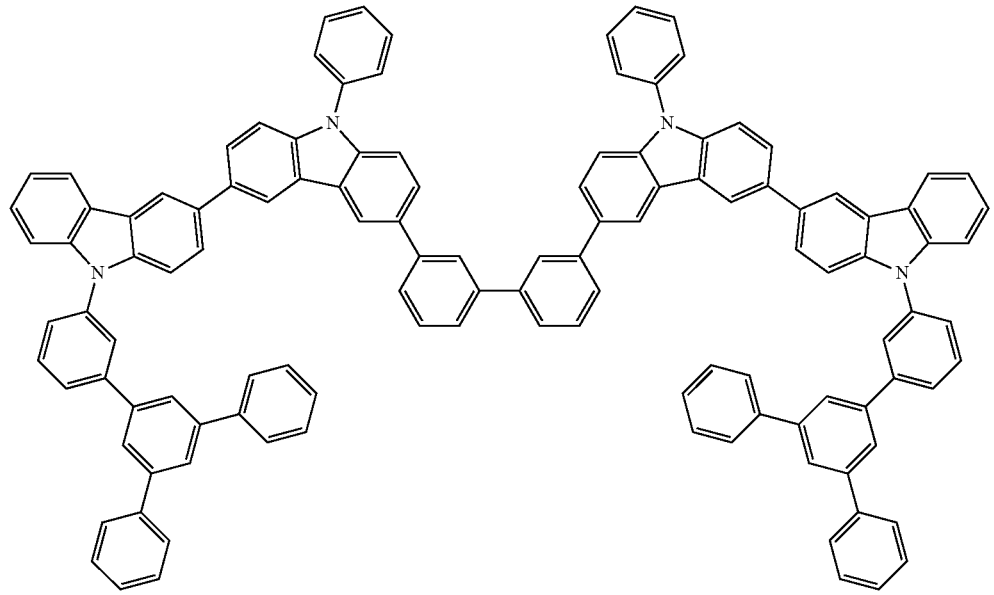
6-49
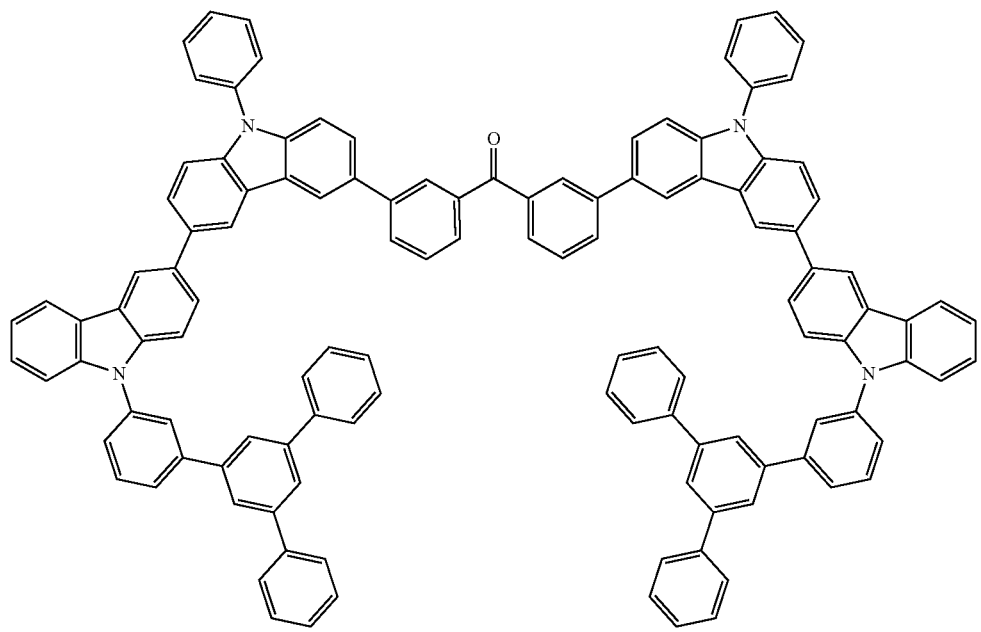

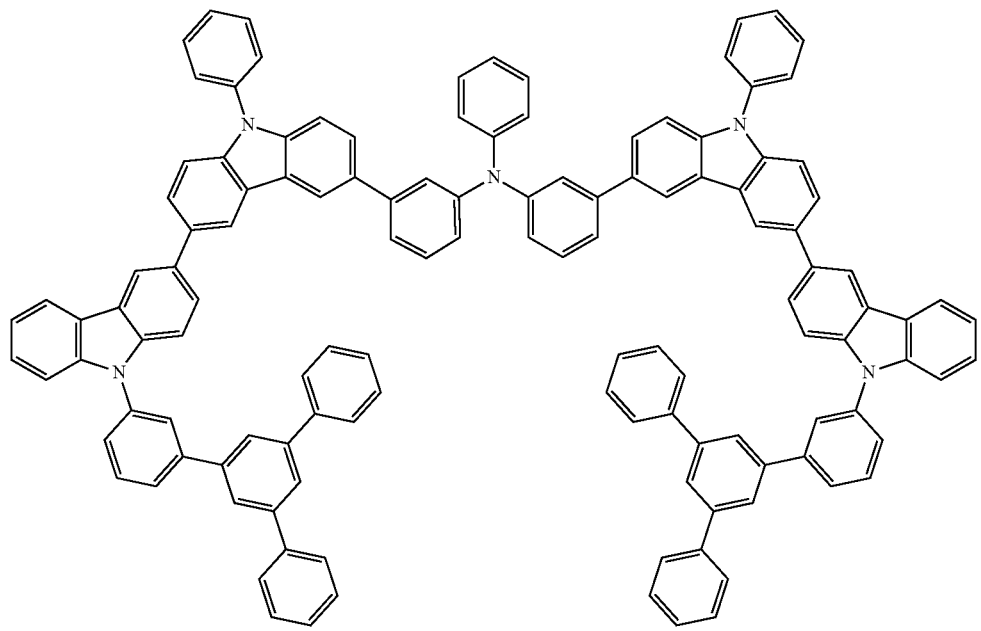
6-50
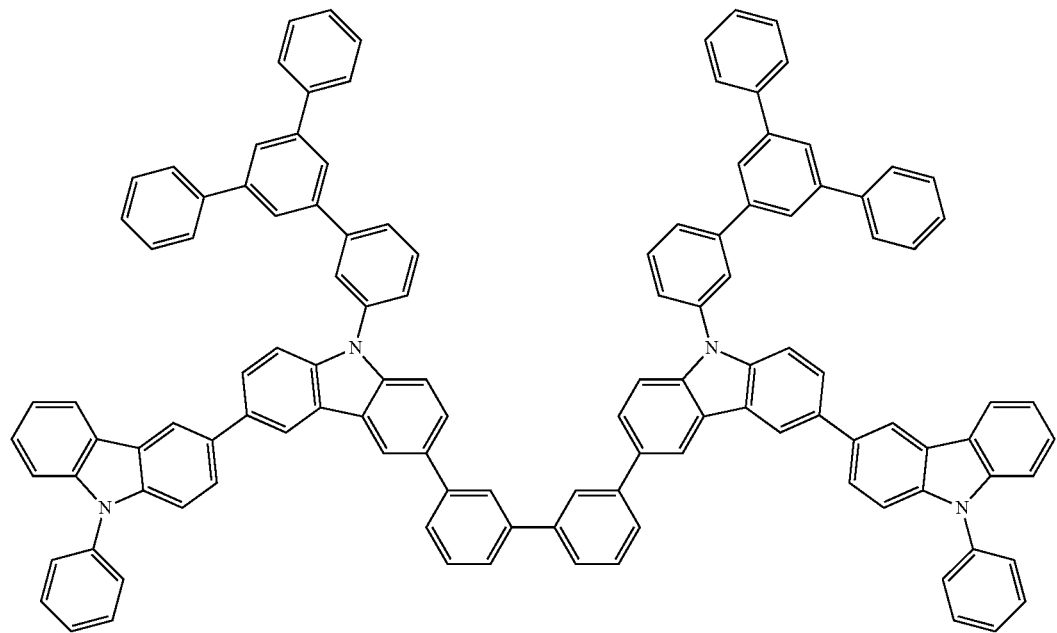
6-51

6-52

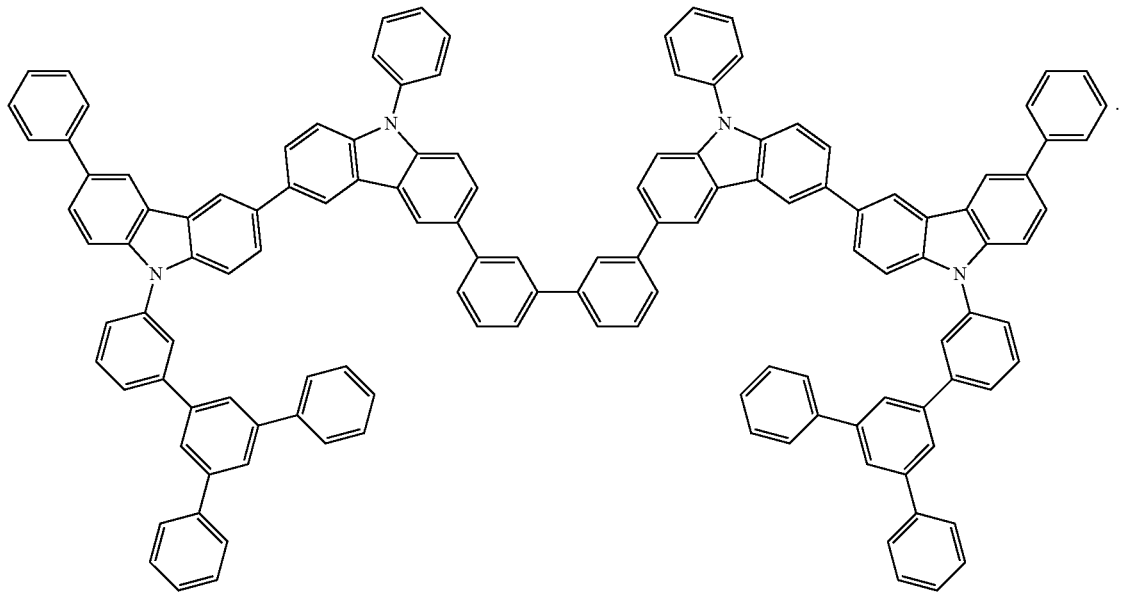

The bicarbazole-containing compound represented by Formula (6) (for example, (6)-1) may have excellent thermal stability due to a relatively high glass transition temperature. Also, the bicarbazole-containing compound may also have a relatively high solubility to the solvent.

An amount ratio of the condensed cyclic compound represented by Formula (1) to the hole transport compound represented by Formula (6) among the materials for forming the organic light-emitting device may be in a range of 100:0 to 1:99, for example, 95:5 to 5:95. In one or more embodiments, an amount ratio of the condensed cyclic compound represented by Formula (1) to the hole transport compound represented by Formula (6) among the materials for forming the organic light-emitting device may be in a range of 80:20 to 20:80, for example, 70:30 to 30:70. While not wishing to be bound by theory, it is understood that when the amount ratio is within this range, effective balance between holes and electrons in the organic light-emitting device may be achieved.

When the material for forming the organic light-emitting device is a material for forming the emission layer, the material for forming the organic light-emitting device may further include a light-emitting material (for example, a phosphorescent dopant or a fluorescent dopant) to be described below.

3. Composition for Manufacturing Organic Light-Emitting Device

The composition for manufacturing the organic light-emitting device may be used for forming each layer of the organic light-emitting device through solution coating.

The composition for manufacturing the organic light-emitting device may include the condensed cyclic compound represented by Formula (1) and a liquid medium.

The liquid medium may be a liquid medium (for example, a solvent or the like) that dissolves the material for forming the organic light-emitting device as described above. That is, the composition for manufacturing the organic light-emitting device may be a solution composition.

Examples of the liquid medium may include toluene, xylene, ethylbenzene, diethylbenzene, mesitylene, propylbenzene, cyclohexylbenzene, dimethoxybenzene, anisole, ethoxy toluene, phenoxytoluene, iso-propylbiphenyl, dimethylanisole, phenyl acetate, a phenyl propionic acid, methyl benzoate, and ethyl benzoate, but embodiments of the present disclosure are not limited thereto.

In the composition for manufacturing the organic light-emitting device, a concentration of the material for forming the organic light-emitting device may be adjusted according to a purpose thereof.

4. Organic Light-Emitting Device

An organic light-emitting device 100 according to an embodiment will be described in connection with the FIGURE. The FIGURE is a schematic view of the organic light-emitting device 100 according to an embodiment.

The organic light-emitting device 100 illustrated in the FIGURE includes a substrate 110, a first electrode 120 disposed on the substrate 110, a hole injection layer 130 disposed on the first electrode 120, a hole transport layer 140 disposed on the hole injection layer 130, an emission layer 150 disposed on the hole transport layer 140, an electron transport layer 160 disposed on the emission layer 150, an electron injection layer 170 disposed on the electron transport layer 160, and a second electrode 180 disposed on the electron injection layer 170.

The condensed cyclic compound represented by Formula (1) may be included in any organic layer disposed between the first electrode 120 and the second electrode 180. For example, the condensed cyclic compound may be included in the emission layer 150 as a host material.

The organic layer including the condensed cyclic compound represented by Formula (1) may be formed by vacuum deposition or solution coating. In one or more embodiments, the organic layer including the condensed cyclic compound may be formed by solution coating. The organic layer including the condensed cyclic compound may be formed by using solution coating, such as spin coating, casting, micro gravure coating, gravure coating, bar coating, roll coating, wire bar coating, dip coating, spray coating, screen-printing, flexographic-printing, offset-printing, and ink-jet printing. The solvent used in solution coating may be selected from any solvents capable of dissolving the condensed cyclic compound represented by Formula (1).

Film-forming methods of forming layers other than the organic layer including the condensed cyclic compound represented by Formula (1) are not particularly limited. For example, a film may be formed by vacuum deposition or solution coating.

For use as the substrate 110, any substrate that is used in general organic light-emitting devices may be used. For example, the substrate 110 may be a glass substrate, a semiconductor substrate such as a silicon substrate, or a transparent plastic substrate.

The first electrode 120 is disposed on the substrate 110. The first electrode 120 may be an anode. A material for forming the first electrode 120 may be a material having a high work function, and such a material may be a metal, an alloy, or an electrically conductive compound. For example, the first electrode 120 may be a transmissive electrode using indium tin oxide (ITO) ($In_2O_3$—$SnO_2$), indium zinc oxide ($In_2O_3$—$ZnO$), tin oxide ($SnO_2$), or zinc oxide ($ZnO$), each having excellent transparent and electrically conductive properties. In one or more embodiments, the first electrode 120 may be a reflective electrode in which magnesium (Mg), aluminum (Al), or the like is additionally laminated on the transmissive electrode.

The hole injection layer 130 is disposed on the first electrode 120. The hole injection layer 130 is a layer that facilitates hole injection from the first electrode 120 to the hole transport layer 140. A thickness of the hole injection layer 130 may be in a range of about 10 nanometers (nm) to about 1,000 nm, for example, about 10 nm to about 500 nm, or for example, about 10 nm to about 100 nm.

The hole injection layer 130 may include a known hole injection material. Examples of the hole injection material may include poly(ether ketone)-containing triphenylamine (TPAPEK), 4-iso-propyl-4"-methyldiphenyliodonium tetrakis(pentafluorophenyl)borate (PPBI), N,N"-diphenyl-N,N"-bis-[4-(phenyl-m-tolyl-amino)-phenyl]-biphenyl-4,4"-diamine (DNTPD), copper phthalocyanine, 4,4",4"-tris(3-methylphenylphenylamino)triphenylamine (m-MTDATA), N,N"-di(1-naphthyl)-N,N"-diphenylbenzidine (NPB), 4,4",4"-tris(diphenylamino)triphenylamine (TDATA), 4,4",4"-tris(N,N-2-naphthylphenylamino)triphenylamine (2-TNATA), polyaniline/dodecylbenzene sulfonic acid, poly (3,4-ethylenedioxythiophene)/poly(4-styrene sulfonate) (PEDOT/PSS), and polyaniline/10-camphor sulfonic acid.

The hole transport layer 140 is disposed on the hole injection layer 130. The hole transport layer 140 is a layer that transports holes to the emission layer 150. A thickness of the hole transport layer 140 may be in a range of about 10 nm to about 150 nm, for example, about 10 nm to about 100 nm.

The hole transport layer 140 may include a known hole transport material. The hole transport material may be 1,1-bis[(di-4-tolylamino)phenyl]cyclohexene (TAPC), N-phenylcarbazole, polyvinylcarbazole, N,N"-bis(3-methylphenyl)-N,N"-diphenyl-[1,1-biphenyl]-4,4"-diamine (TPD), 4,4",4"-tris(N-carbazolyl)triphenylamine (TCTA), N,N"-di(1-naphthyl)-N,N"-diphenylbenzidine (NPB), or (poly[(9,9-dioctylfluorenyl-2,7-diyl)-co-(4,4'-(N-(4-sec-butylphenyl)diphenylamine)]) (TFB).

The emission layer 150 is disposed on the hole transport layer 140. The emission layer 150 is a layer that emits fluorescence and/or phosphorescence. The emission layer 150 may be formed using vacuum deposition, spin coating, and/or ink-jet printing. A thickness of the emission layer 150 may be in a range of about 10 nm to about 60 nm, for example, about 10 nm to about 50 nm, or for example, about 10 nm to about 40 nm. For use as the light-emitting material of the emission layer 150, a known light-emitting material may be used. In one or more embodiments, the light-emitting material included in the emission layer 150 may be a light-emitting material (for example, a phosphorescent dopant) that may emit light (that is, phosphorescence) from triplet excitons. When the light-emitting material is a phosphorescent material, the light emission lifespan of the organic light-emitting device 100 may be further improved.

The emission layer 150 may be formed by solution coating using the condensed cyclic compound represented by Formula (1) as the material for forming the organic light-emitting device (for example, using a composition including the condensed cyclic compound represented by Formula (1) and a liquid medium). The use of solution coating may improve the light emission lifespan of the organic light-emitting device 100 and may achieve efficient film formation of the large-area emission layer 150 including the condensed cyclic compound.

In one or more embodiments, the emission layer 150 may include a host, and the host may include the condensed cyclic compound represented by Formula (1). The emission layer 150 may be formed by solution coating using a composition including the condensed cyclic compound represented by Formula (1) and the liquid medium.

In one or more embodiments, the emission layer 150 may include a host, and the host may include the condensed cyclic compound represented by Formula (1) and the hole transport compound represented by Formula (6) (for example, Formula (6)-1). The emission layer 150 may be formed by solution coating using a composition including the condensed cyclic compound represented by Formula (1), the hole transport compound represented by Formula (6) (for example, Formula (6)-1), and the liquid medium.

In one or more embodiments, the emission layer 150 may include a host and a dopant. The host may include the condensed cyclic compound represented by Formula (1), and the dopant may include a fluorescent dopant or a phosphorescent dopant (for example, a phosphorescent dopant). The emission layer 150 may be formed by solution coating using a composition including the condensed cyclic compound represented by Formula (1), the dopant, and the liquid medium.

In one or more embodiments, the emission layer 150 may include a host and a dopant. The host may include the condensed cyclic compound represented by Formula (1) and the hole transport compound represented by Formula (6) (for example, Formula (6)-1), and the dopant may include a fluorescent dopant or a phosphorescent dopant (for example, a phosphorescent dopant). The emission layer 150 may be formed by solution coating using a composition including the condensed cyclic compound represented by Formula (1), the hole transport compound represented by Formula (6) (for example, Formula (6)-1), the dopant, and the liquid medium.

In the embodiments, the host may include only one condensed cyclic compound represented by Formula (1), or may include two or more different condensed cyclic compounds represented by Formula (1). Various modifications may be made to the host. For example, the host may include i) only Compound 1-7 as the condensed cyclic compound represented by Formula (1) or ii) a mixture of Compounds 1-5 and 1-7 as the condensed cyclic compound represented by Formula (1).

When the composition for manufacturing the organic light-emitting device is formed in a certain region (for example, the emission layer 150), a film may be formed by providing the composition on the hole transport layer 140 and removing at least a part of the liquid medium in the composition. The process of removing a part of the liquid medium may include a thermal treatment. The temperature and time of the thermal treatment may vary depending on a material included in the composition for manufacturing the organic light-emitting device.

When another organic layer of the organic light-emitting device 100 includes the condensed cyclic compound represented by Formula (1), the emission layer 150 may include a known material.

For example, the emission layer 150 may include, as the known host material, tris(8-quinolinato)aluminium ($Alq_3$), 4,4"-bis(carbazol-9-yl)biphenyl (CBP), poly(n-vinyl carbazole) (PVK), 9,10-di(naphthalene)anthracene (ADN), 4,4", 4"-tris(N-carbazolyl)triphenylamine (TCTA), 1,3,5-tris(N-phenyl-benzimidazol-2-yl)benzene (TPBI), 3-tert-butyl-9,10-di(naphth-2-yl)anthracene (TBADN), distyrylarylene (DSA), or 4,4"-bis(9-carbazole) 2,2-dimethyl-bipheny (dm-CBP).

The emission layer 150 may include, as the dopant material, a perylene and a derivative thereof, rubrene and a derivative thereof, coumarin and a derivative thereof, 4-dicyanomethylene-2-(p-dimethylaminostyryl)-6-methyl-4H-pyran (DCM) and a derivative thereof, an iridium (Ir) complex such as bis[2-(4,6-difluorophenyl)pyridinate]picolinate iridium (III) (Flrpic), bis(1-phenylisoquinoline)(acetylacetonate)iridium (III) ($Ir(piq)_2(acac)$), tris(2-phenylpyridine)iridium (III) ($Ir(ppy)_3$), and tris (2-(3-p-xylyl)phenyl)pyridine iridium(III), an osmium (Os) complex, or a platinum complex.

Also, the emission layer 150 may include a quantum dot as the light-emitting material. The quantum dot may have a single core structure including Group II-VI semiconductors, Group III-V semiconductors, or Group IV-IV semiconductors, or a core/shell structure in which Group II-VI semiconductors are capped in the single core structure. A nanoparticle of the quantum dot may have a diameter of about 1 nm to about 20 nm, for example, about 1 nm to about 10 nm, but embodiments of the present disclosure are not limited thereto.

In the core or core/cap structure, the quantum dot corresponding to the core may use any type of semiconductor, For example, the Group II-VI semiconductors are a combination of at least one of Group IIB elements and at least one of group VIB elements in the periodic table. The Group II-VI semiconductors may be CdS, CdSe, CdTe, ZnSe, ZnS, PbS, PbSe, HgS, HgSe, HgTe, CdHgTe, or $CdSe_xTe_{1-x}$ (wherein x is a real number of 0<x<1). Also, the group III-V semiconductors may be GaAs, InAs, or InP.

In the core/shell structure, the shell refers to a semiconductor quantum dot that is linked to a core semiconductor quantum dot to form a coating layer on a surface of a core semiconductor. Compared with the single core structure, the core/shell structure may obtain excellent light emission efficiency. The shell may have a band gap that is higher than that of the core semiconductor and may act as a passivation layer that protects the core semiconductor from the outside. The shell may include Group II-VI semiconductors having a high band gap. For example, the shell may include ZnS, CdS, or ZnSe. In the combination of these core/shell structures, when the core includes CdSe or CdS, the shell may include ZnS, and when the core includes CdSe, the shell may include CdS or ZnSe. In this way, various combinations may be used without limitations.

An amount of the dopant may be in a range of about 0.01 parts to 20 parts by weight, for example, about 0.1 parts to 20 parts by weight, based on 100 parts by weight of the emission layer 150. While not wishing to be bound by theory, it is understood that when the amount of the dopant is within this range, effective light emission may be achieved without concentration quenching.

The electron transport layer 160 is disposed on the emission layer 150. The electron transport layer 160 is a layer that has an electron transport function. The electron transport layer 160 may be formed using vacuum deposition, spin coating, or ink-jet printing. The electron transport layer 160 may have a thickness of about 15 nm to about 80 nm, for example, about 30 nm to about 60 nm.

The electron transport layer 160 may include a known electron transport material. The electron transport material may be tris(8-quinolinato)aluminium ($Alq_3$), or a nitrogenous aromatic ring-containing compound. For example, the nitrogenous aromatic ring-containing compound may be a pyridine ring-containing compound such as 1,3,5-tri[(3-pyridyl)-phen-3-yl]benzene, a triazine ring-containing compound such as 2,4,6-tris(3"-(pyridin-3-yl)biphenyl-3-yl)-1,3,5-triazine), or an imidazole ring-containing compound such as 2-(4-(N-phenylbenzoimidazol-1-yl-phenyl)-9,10-dinaphthylanthracene.

The electron transport layer 160 may further include, in addition to the organic compounds described above, a metal-containing compound such as (8-quinolinato)lithium (Liq).

The electron injection layer 170 is disposed on the electron transport layer 160. The electron injection layer 170 is a layer that has a function of facilitating injection of electrons from the second electrode 180. The electron injection layer 170 may be formed using vacuum deposition or the like. The electron injection layer 170 may have a thickness of about 0.3 nm to about 9 nm, for example, about 1 nm to about 5 nm.

For use as the material for forming the electron injection layer 170, a known electron injection material may be used. The electron injection material may be a lithium compound such as (8-quinolinato)lithium (Liq) and lithium fluoride (LiF), sodium chloride (NaCl), cesium fluoride (CsF), lithium oxide ($Li_2O$), or barium oxide (BaO), but embodiments of the present disclosure are not limited thereto.

The second electrode 180 is disposed on the electron injection layer 170. The second electrode 180 may be a cathode. A material for forming the second electrode 180 may be a material having a low work function, and such a material may be a metal, an alloy, or an electrically conductive compound. For example, the second electrode 180 may be a reflective electrode using a metal such as lithium (Li), magnesium (Mg), aluminum (Al), and calcium (Ca), or an alloy using aluminum-lithium (Al—Li), magnesium-indium (Mg—In), and magnesium-silver (Mg—Ag). Also, the second electrode 180 may be a transmissive electrode using a thin film including the metal material and having a thickness of about 20 nm or less, for example, about 10 nm or less, or a transparent, electrically conductive film such as ITO ($In_2O_3$—$SnO_2$) and IZO ($In_2O_3$—ZnO).

An embodiment of the organic light-emitting device 100 has been described in connection with the FIGURE. The organic light-emitting device 100 may have, due to inclusion of an organic layer including the condensed cyclic compound represented by Formula (1), an improved light emission lifespan.

The stacked structure of the organic light-emitting device 100 is not limited to the above-described embodiments. The organic light-emitting device 100 may have another known stacked structure. For example, at least one of the hole injection layer 130, the hole transport layer 140, the electron transport layer 160, and the electron injection layer 170 in the organic light-emitting device 100 may be omitted, or another layer such as a resonant auxiliary layer, a buffer layer, a hole blocking layer, or an electron blocking layer may be added to the organic light-emitting device 100. In this way, various modifications may be made thereto. Also, each layer of the organic light-emitting device 100 may be variously modified. For example, each layer of the organic light-emitting device 100 has a single layer or multiple layers.

For example, the organic light-emitting device 100 may further include a hole blocking layer between the emission layer 150 and the electron transport layer 160 so as to prevent excitons or holes from diffusing into the electron transport layer 160. For example, the hole blocking layer may include an oxazole (oxadiazole) derivative, a triazole derivative, or a phenanthroline derivative.

The term "$C_1$-$C_{60}$ alkyl group" as used herein refers to a linear or branched saturated aliphatic hydrocarbon monovalent group having 1 to 60 carbon atoms, and non-limiting examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by -O$A_{101}$ (wherein $A_{101}$ is the $C_1$-$C_{60}$ alkyl group), and non-limiting examples thereof include a methoxy group, an ethoxy group, and an iso-propyloxy (iso-propoxy) group.

The term "$C_2$-$C_{60}$ alkenyl group" as used herein refers to a hydrocarbon group formed by including at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by including at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si and S as a ring-forming atom and 1 to 10 carbon atoms, and non-limiting examples thereof include a tetrahydrofuranyl group and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and which is not aromatic, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one carbon-carbon double bond in its ring. Examples of the $C_2$-$C_{10}$ heterocycloalkenyl group are a 2,3-dihydrofuranyl group and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a heterocyclic aromatic system that has at least one heteroatom selected from N, O, P, Si, and S as a ring-forming atom, and 1 to 60 carbon atoms. The term "$C_1$-$C_{60}$ heteroarylene group," as used herein refers to a divalent group having a heterocyclic aromatic system that has at least one heteroatom selected from N, O, P, Si, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein refers to -O$A_{102}$ (wherein $A_{102}$ is the $C_6$-$C_{60}$ aryl group), and a $C_6$-$C_{60}$ arylthio group as used herein indicates -S$A_{103}$ (wherein $A_{103}$ is the $C_6$-$C_{60}$ aryl group).

The term "monovalent non-aromatic condensed polycyclic group" as used herein refers to a monovalent group having two or more rings condensed to each other, only carbon atoms (for example, the number of carbon atoms may be in a range of 8 to 60) as a ring-forming atom, and which is not aromatic in the entire molecular structure. Non-limiting examples of the monovalent non-aromatic condensed polycyclic group include a fluorenyl group. The term "divalent non-aromatic condensed polycyclic group," as used herein, refers to a divalent group having the same structure as the monovalent non-aromatic condensed polycyclic group.

The term "monovalent non-aromatic condensed heteropolycyclic group" as used herein refers to a monovalent group having two or more rings condensed to each other, a heteroatom selected from N, O, P, Si, and S, other than carbon atoms (for example, the number of carbon atoms may be in a range of 2 to 60), as a ring-forming atom, and which is not aromatic in the entire molecular structure. Non-limiting examples of the monovalent non-aromatic condensed heteropolycyclic group include a carbazolyl group. The term "divalent non-aromatic condensed heteropolycyclic group," as used herein, refers to a divalent group having the same structure as the monovalent non-aromatic condensed heteropolycyclic group.

At least one substituent of the substituted $C_2$-$C_{60}$ alkylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, -CD$_3$, -CD$_2$H, -CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, -CD$_3$, -CD$_2$H, -CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si(Q$_{11}$)(Q$_{12}$)(Q$_{13}$), —N(Q$_{11}$)(Q$_{12}$), and —C(=O)(Q$_{11}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, -CD$_3$, -CD$_2$H, -CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si(Q$_{21}$)(Q$_{22}$)(Q$_{23}$), —N(Q$_{21}$)(Q$_{22}$), and —C(=O)(Q$_{21}$); and —Si(Q$_{31}$)(Q$_{32}$)(Q$_{33}$), —N(Q$_{31}$)(Q$_{32}$)$_{32}$, and —C(=O)(Q$_{31}$);

wherein $Q_{11}$ to $Q_{13}$, $Q_{21}$ to $Q_{23}$, and $Q_{31}$ to $Q_{33}$ may each independently be selected from hydrogen, deuterium, a $C_1$-$C_{20}$ alkyl group, a $C_1$-$C_{20}$ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, and a diphenyldibenzothiophenyl group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

The term "biphenyl group" as used herein refers to a monovalent group in which two benzene groups are linked via a single bond.

The term "terphenyl group" as used herein refers to a monovalent group in which three benzene groups are linked via a single bond.

* and *' used herein, unless defined otherwise, each refers to a binding site to a neighboring atom in a corresponding formula.

Hereinafter, a compound and an organic light-emitting device according to embodiments are described in detail with reference to Synthesis Examples and Examples. However, the organic light-emitting device is not limited thereto. The wording "B was used instead of A" used in describing Synthesis Examples means that an amount of A used was identical to an amount of B used, in terms of a molar equivalent.

EXAMPLE

1. Synthesis

Synthesis Example 1: Synthesis of Compound 1-7

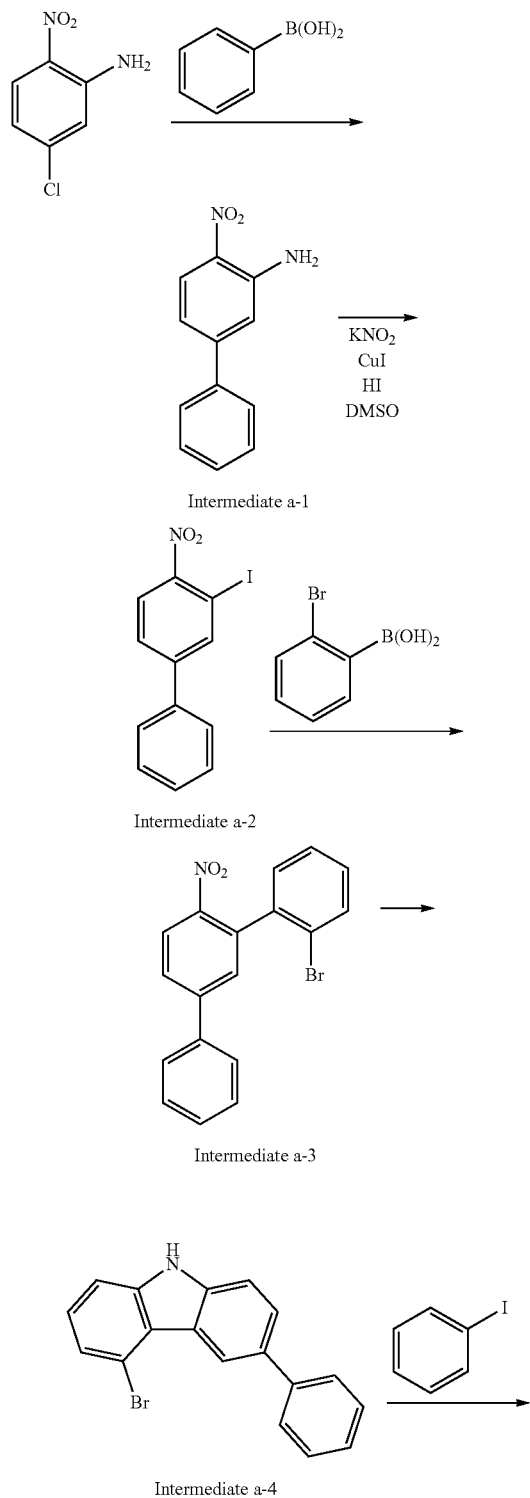

Intermediate a-1

Intermediate a-2

Intermediate a-3

Intermediate a-4

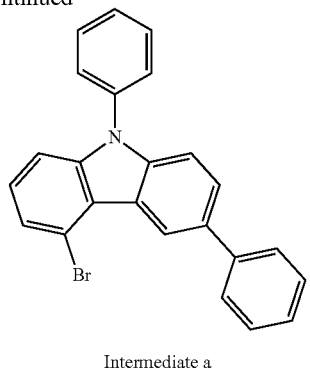

Intermediate a

Synthesis of Intermediate a (5-phenyl-2-nitroaniline)

190.10 grams (g) (1.10 moles, mol) of 5-chloro-2-nitroaniline, 161.05 g (1.32 mol, 1.2 equivalents, eq) of a phenylboronic acid, 2.2 liters (L) of 2 M potassium carbonate (aqueous solution, aq), and 2.2 L of toluene were stirred in a nitrogen atmosphere. The obtained resultant mixture was purged with nitrogen ($N_2$) for 20 minutes, 63.56 g (55 mmol, 0.05 eq) of tetrakis-triphenylphosphine palladium(0) was added thereto, and the mixture was heated under reflux for 6 hours. After the reaction was completed, the resultant obtained therefrom was cooled and 500 milliliters (mL) of water was added thereto. The extraction process was performed thereon three times by using 500 mL of toluene, and washing thereof was performed by using 500 mL of water and 500 mL of brine, each operation twice. Drying thereof was performed by using sodium sulfate. The resultant obtained therefrom was filtered and concentrated to obtain 410.2 g of a crude product. The crude product was dissolved in toluene. The resultant mixture was adsorbed on 800 g of amine modified silica gel in about twice amount (an eluent was ethyl acetate/toluene=1/5 (volume to volume, v/v)), and column purification was performed thereon in 2,870 g of amine modified silica gel 7 times, thereby completing the preparation of Intermediate a-1 (yellow solid) (synthesized amount: 210 g, yield: 89%, purity (GC): 98%).

Synthesis of Intermediate a-2 (3-Iodo-4-nitro-1,1'-biphenyl)

221.31 g (1.03 mol) of Intermediate a-1 (5-phenyl-2-nitroaniline), (185.3 g, 2.18 mol, 2.1 eq) of potassium nitrite ($KNO_2$), 187.0 g (0.982 mol, 1 eq) of copper iodide (I), and 2.5 L of dimethylsulfoxide (DMSO) were stirred in a nitrogen atmosphere. The resultant mixture obtained therefrom was heated to a temperature of 60° C., and 1,976 g (8.5 mol, 8.23 eq) of a 55% hydriodic acid was added by drops for 30 minutes. The resultant was then stirred at a temperature of 60° C. for 30 minutes and cooled by removing the heating source and ice cooling. The reaction was quenched by adding 3 L of an aqueous solution containing 1,078 g of potassium carbonate to the reactant. A separation process was performed thereon by adding 2.5 L of diethyl ether thereto. The extraction process was performed thereon four times by using 2.0 L of diethyl ether, and the washing thereof was performed by using 3.0 L of water, 3.0 L of a sodium thiosulfate aqueous solution, and 2.0 L of brine, each operation twice. Drying thereof was performed by using sodium sulfate. The resultant obtained therefrom was filtered and concentrated to obtain 312.1 g of a crude product. The crude product was dissolved in dichloromethane. The resultant mixture was adsorbed on 624 g of silica gel in about twice amount (an eluent=dichloromethane/hexane=1/10 (v/v)), and column purification was performed thereon by using 1,433 g of silica gel 5 times, thereby completing the preparation of Intermediate a-2 (yellow crystal) (synthesized amount: 292 g, yield: 85%, purity (GC): 98%).

Synthesis of Intermediate a-3 (2-bromo-6'-nitro-1,1':3',1-terphenyl)

20.0 g (61.43 mmol) of Intermediate a-2 (3-iodo-4-nitro-1,1"-biphenyl) and 12.8 g (6,373 mmol) of an o-bromophenyl boronic acid was dissolved in an $N_2$ bubbled toluene/DME mixture solvent (86 mL/86 mL), and 1.42 g (1.23 mmol) of tetrakis-triphenylphosphine palladium (0) and 86 mL of 2 M sodium carbonate (aq) were sequentially added thereto, and the mixture was heated under reflux for 10 hours. The resultant obtained therefrom was cooled to room temperature and an extraction process was performed thereon twice by using 150 mL of pure water and 200 mL of toluene. An organic layer obtained therefrom was washed by using 200 mL of brine, and dried by using sodium sulfate. The resultant was filtered and concentrated to obtain 23.2 g of a crude product. Column purification was performed on the crude product by using 700 g of silica gel (hexane/toluene (=1/1 (v/v)) eluent). The vacuum drying was performed thereon at a temperature of 40° C. for 16 hours, thereby completing the preparation of Intermediate a-3 (light yellow viscous liquid) (synthesized amount: 18.2 g, yield: 83%, purity (HPLC): 99.5%).

Synthesis of Intermediate a-4 (5-bromo-3-phenyl-9H-carbazole)

18.15 g (51.24 mmol) of Intermediate a-3 (2-bromo-6"-nitro-1,1":3",1-terphenyl) was dissolved in 110 mL of o-dichlorobenzene in an inert atmosphere, and 32.0 g (122.0 mmol) of triphenylphosphine was added thereto. The resultant mixture was stirred at a temperature of 180° C. for 20 hours. The outside temperature and pressure were adjusted to 80° C. and 1 Torr or less, and the solvent was removed to obtain 54.9 g of a viscous crude product. A mixed solution of hexane/toluene (=1/1 (v/v) was added thereto to precipitate a target object. The target object was separated by filtration under reduced pressure and washed by using a mixed solution of hexane/toluene (=1/1 (v/v)). The filtrate obtained therefrom was concentrated to obtain 45.0 g of a crude product. The column purification was performed on the crude product by using 900 g of silica gel (hexane/toluene (=1/1 (v/v)) eluent), and a solvent was removed to obtain 14.1 g of a light yellow viscous liquid. 50 mL of hexane was added to the light yellow viscous liquid, and the resultant mixture was heated and stirred at a temperature of 60° C. A precipitate collected therefrom was dried under reduced pressure for 15 hours, thereby completing the preparation of Intermediate a-4 (light yellow solid) (synthesized amount: 13.5 g, yield: 81%, purity (HPLC): 99.1%).

Synthesis of Intermediate a (5-bromo-3,9-diphenyl-9H-carbazole)

13.46 g (41.78 mmol) of Intermediate a-4 (5-bromo-3-phenyl-9H-carbazole) and 9.50 g (46.57 mmol) iodobenzene were mixed with 41 mL of 1,4-dioxane, and 0.40 g (2.09 mmol) of CuI, 0.96 g (8.41 mmol) of trans-1,2-diaminocyclohexane, and 2.02 g (21.02 mmol) of tert-BuONa were sequentially added thereto. The resultant mixture was stirred at a temperature of 105° C. for 20 hours. The resultant mixture was cooled to room temperature, filtered under reduced pressure by using 10 g of celite, and washed by using dioxane. A solvent was removed from a filtrate obtained therefrom to thereby obtain 25.30 g of a crude product. The crude product was dissolved in dichloromethane and absorbed on 100 g of silica gel, and the solvent was evaporated. Column purification was performed thereon by using 400 g of the adsorbed silica gel and a hexane/toluene (=1/1 (v/v)) eluent, the solvent was removed therefrom, and the residue was vacuum-dried, thereby completing the preparation of Intermediate a (colorless solid) (synthesized amount: 14.6 g, yield: 88%, purification (HPLC): 99.0%).

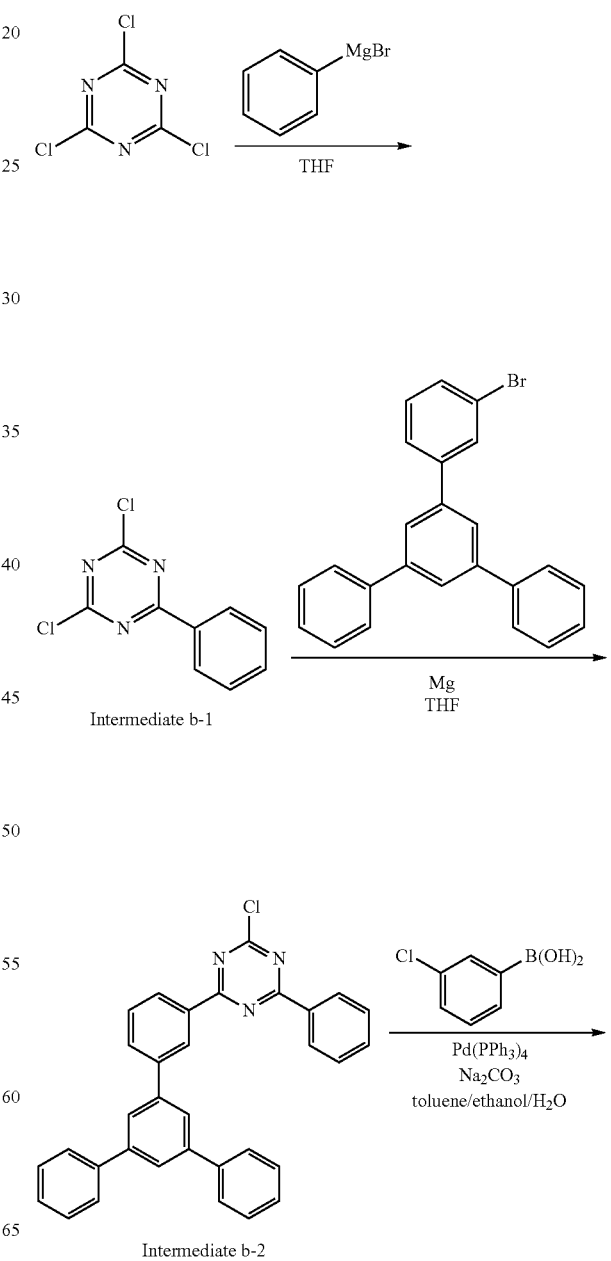

Intermediate b-1

Intermediate b-2

-continued

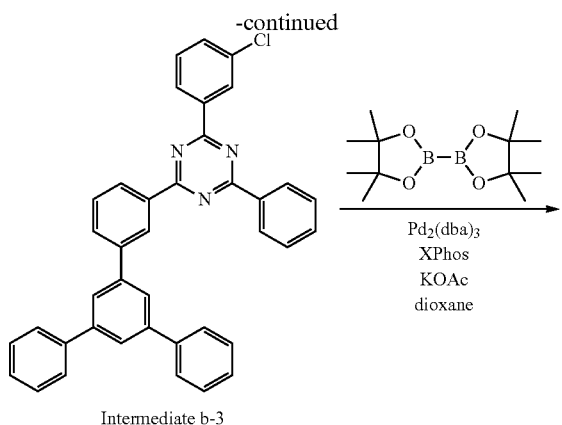

Intermediate b-3

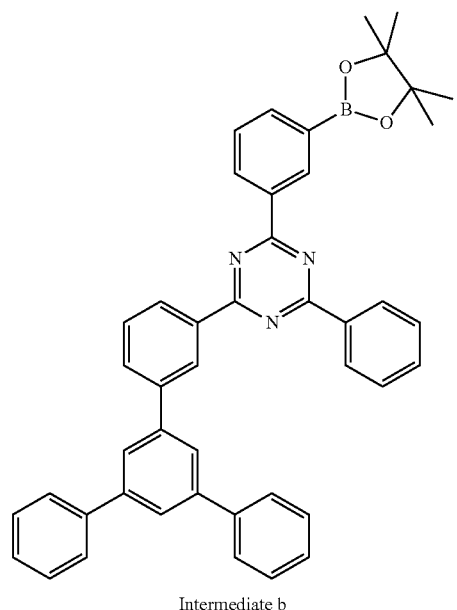 [SMILES: CC1(C)OB(c2cccc(-c3nc(-c4ccccc4)nc(-c4cccc(-c5cc(-c6ccccc6)cc(-c6ccccc6)c5)c4)n3)c2)OC1(C)C]

Intermediate b

Synthesis of Intermediate b-1 (2,4-dichloro-6-phenyl-1,3,5-triazine)

30.0 g (162.7 mmol) of a cyanuric acid was added to a 2-L round bottom flask and an atmosphere inside the flask was evacuated and purged with argon three times by using a vacuum pump. Then, 975 mL of dry toluene was added to the flask, and the resultant mixture was cooled to a temperature of 0° C. by using an ice bath. 29.5 g (162.3 mmol) of phenyl magnesium bromide and 54.2 mL of a dry diethyl ether solution were added by drops thereto in an argon atmosphere. A resultant obtained therefrom was gradually heated to room temperature and stirred for 2 hours. The reaction was quenched by using 200 mL of 6 normal (N) HCl (aq) at a temperature of 0° C., and an extraction process was performed thereon by using toluene. An organic layer collected therefrom was dried by using MgSO$_4$ and concentrated in vacuum to obtain a crude product. The crude product was dissolved in tetrahydrofuran (THF) and poured into 200 mL of excess methanol, and a reprecipitation process was repeated twice. A crude product obtained therefrom was dissolved in THF and poured into 100 mL of hexane. The resultant obtained by reprecipitation was vacuum-dried at a temperature of 40° C. for 5 hours, thereby completing the preparation of Intermediate b-1 (off-white solid) (synthesized amount: 33.4 g, yield: 60%, purity (HPLC): 98.7%).

Synthesis of Intermediate b-2 (2-chloro-4-phenyl-6-(5'-phenyl-[1,1':3',1''-terphenyl]-3-yl)-1,3,5-triazine)

1.83 g (75.3 mmol) of Mg was added to a 300-mL round bottom flask and the atmosphere inside the flask was ventilated with argon three times by using a vacuum pump. 30 mL of dry THF was added to the flask, and the resultant mixture was cooled to a temperature of −78° C. by using a dry ice ethanol bath. 29.0 g (75.3 mmol) of 3-bromo-5'-phenyl-1,1':3',1''-terphenyl and 166 mL of a dry THF solution were added by drops thereinto in an argon atmosphere. The resultant obtained therefrom was gradually heated to room temperature and stirred for 30 minutes. The resultant mixture was slowly added by drops into 196 mL of a dry THF solution containing 20.4 g (90.3 mmol) of 2,4-dichloro-6-phenyl-1,3,5-triazine at a temperature of 0° C. The resultant obtained therefrom was gradually heated to room temperature and stirred for 2 hours. After the reaction was finished at a temperature of 0° C., the reactant was extracted by using toluene. An organic layer obtained therefrom was dried by using Na$_2$SO$_4$ and the solvent was evaporated in vacuum. A crude product obtained therefrom was dissolved in THF and poured into excess methanol, and reprecipitation thereof was repeated twice. The resultant obtained therefrom was dried at a temperature of 40° C. in vacuum for 5 hours, thereby completing the preparation of Intermediate b-2 (off-white solid) (synthesized amount: 25.9 g, yield: 69%, purity (HPLC): 96.8%).

Synthesis of Intermediate b-3 (2-(3-chlorophenyl)-4-phenyl-6-(5'-phenyl-[1,1':3',1''-terphenyl]-3-yl)-1,3,5-triazine)

19.5 g (39.3 mmol) of Intermediate b-3, 6.15 g (39.3 mmol) of a (3-chlorophenyl)boronic acid, 0.91 g (0.79 mmol) of Pd(PPh$_3$)$_4$, and 12.5 g (118 mmol) of sodium carbonate were dissolved in 160 mL of toluene and mixed with 80 mL of ethanol and 160 mL of deionized water in a 500-mL round bottom flask. The obtained mixture was refluxed for 2 hours in an argon atmosphere. After the reaction, the resultant mixture was poured into 300 mL of pure water, a precipitate was filtered, and washing thereof was performed by using methanol. A crude solid obtained therefrom was dissolved in toluene and poured into excess methanol. The resultant obtained by reprecipitation was dried at a temperature of 40° C. in vacuum for 5 hours, thereby completing the preparation of Intermediate b-3 (synthesized amount: 21.0 g, yield: 93%, purity (HPLC): 97.1%).

Synthesis of Intermediate b (2-phenyl-4-(5'-phenyl-[1,1':3',1''-terphenyl]-3-yl)-6-(3-(4,4,5,5-tetramethyl-1,3,2-dioxaborolan-2-yl)phenyl)-1,3,5-triazine)

20.0 g (35.0 mmol) of Intermediate b-3, 17.8 g (69.9 mmol) of bis-(pinacolate)-diboron, 1.60 g (1.75 mmol) of $Pd_2(dba)_3$, 1.67 g (3.50 mmol) of XPhos, and 10.3 g (105 mmol) of potassium acetate were mixed with 350 mL of 1,4-dioxane in a round bottom flask, and the obtained mixture was refluxed in an argon atmosphere for 2 hours. After the reaction, the resultant mixture was filtered by using celite and concentrated by using a rotary evaporator. A crude product obtained therefrom was purified by Si-gel column chromatography (a toluene/hexane mixture was used as an eluent and a mixture ratio was gradually mixed from 1/4 to 1/0 (only toluene), thereby completing the preparation of Intermediate b (white solid) (synthesized amount: 18.0 g, yield: 78%, purity (HPLC): 99.9%).

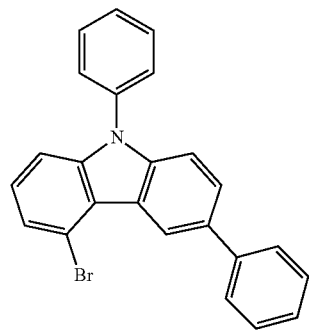

Intermediate a

+

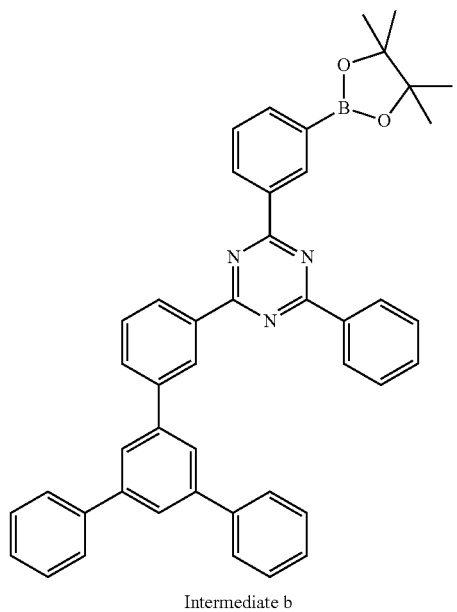

Intermediate b

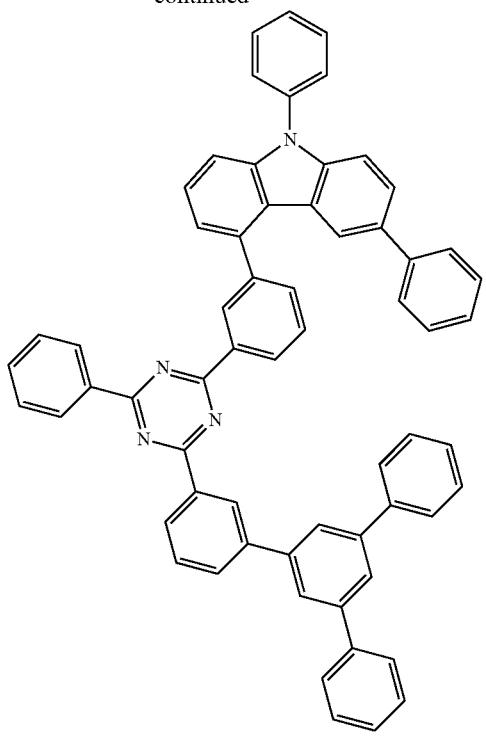

Compound 1-7

Synthesis of Compound 1-7

In an argon atmosphere, 2.20 g (5.52 mmol) of Intermediate a, 3.30 g (4.97 mmol) of Intermediate b, 0.078 g (0.11 mmol) of dichlorobis(triphenylphosphine)dipalladium, 55 mL of dioxane, and 28 mL of a 0.5 N sodium carbonate aqueous solution were added to a reaction vessel, and the mixture was stirred at a temperature of 90° C. for 8 hours. After the reaction was completed, the resultant mixture was cooled to room temperature and filtered by using celite. An organic layer obtained therefrom was concentrated and purified by column chromatography, thereby completing the preparation of Compound 1-7 (synthesized amount: 2.97 g, yield: 69.9%) (the structure thereof was identified by LC-MS). A measurement of a glass transition temperature (Tg) was performed based on JIS K 7121 by using SII DSC6220 (manufactured by Seiko Instruments Inc.).

LC-MS, calcd for $C_{63}H_{42}N_4$=855, found m/z=855 (M+H$^+$).

Tg: 145.5° C.

Solubility (xylene)>10 wt %

Synthesis Example 2: Synthesis of Compound 6-5
Compound 6-5 was synthesized according to the Reaction Scheme below.
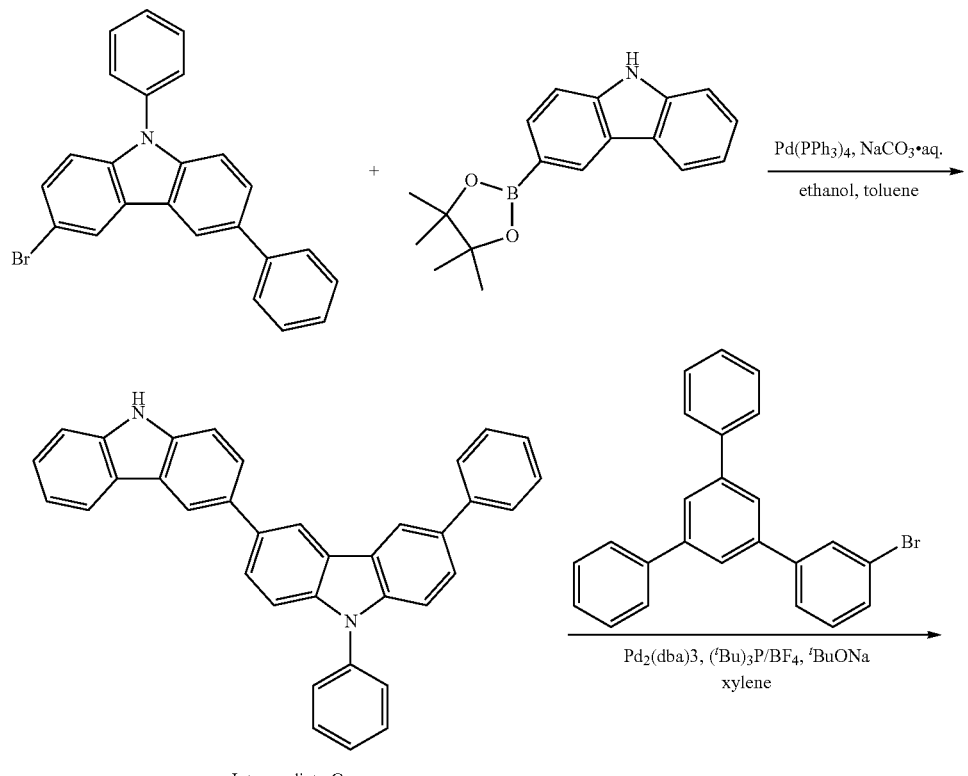
Intermediate C
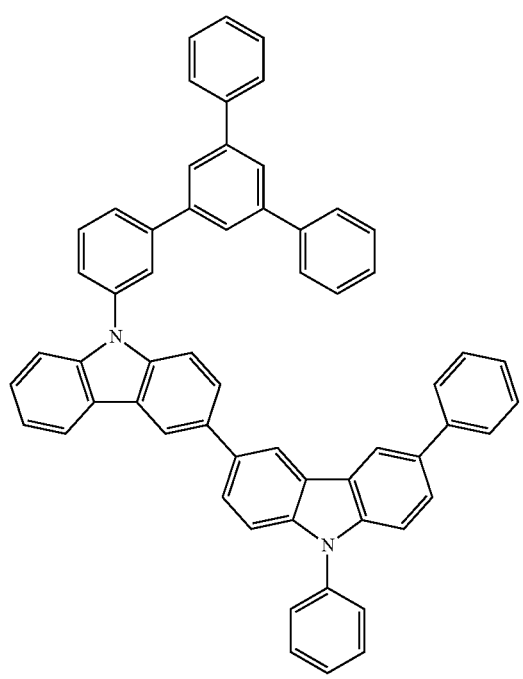
Compound 6-5

Synthesis of Intermediate c

In an argon atmosphere, 6.8 g (17.1 mmol) of 3-bromo-6,9-diphenylcarbazole, 5.0 g (17.1 mmol) of 3-(4,4,5,5-tetramethyl-1,3,2-dioxaborolan-2-yl)-9H-carbazole, 52 mL of toluene, 17 mL of ethanol, and 25 mL of a 2 N sodium carbonate aqueous solution ($Na_2CO_3$ aq.) were mixed and stirred. Then, 0.60 g (0.51 mmol) of tetrakistriphenylphosphine palladium ($Pd(PPh_3)_4$) was added thereto, and the reaction mixture was refluxed for 8 hours. After the reaction was completed, the resultant mixture was cooled to room temperature, extracted by using toluene/water, and purified by column chromatography, thereby completing the preparation of Intermediate c (synthesized amount: 3.0 g, yield: 36%).

Synthesis of Compound 6-5

In an argon atmosphere, 3.0 g (6.19 mmol) of Intermediate c and 2.64 g (6.85 mmol) of 3-bromo-5''-phenyl-1,1'':3'',1''-terphenyl were mixed with 26 mL of dehydrated xylene. Then, 0.120 g (0.130 mmol) of tris(dibenzylideneacetone)dipalladium ($Pd_2(dba)_3$), 0.150 g (0.520 mmol) of tri-tert-butylphosphine tetrafluoroborate:($(tBu)_3P/BF_4$)), and 0.90 g (9.37 mmol) of sodium-t-butoxide (tBuONa) were added thereto, and the reaction mixture was refluxed for 8 hours. The resultant mixture was cooled to room temperature, filtered by using celite, and extracted by using toluene and a saturated saline solution, and purified by column chromatography, thereby completing the preparation of Compound 6-5 (light yellow solid) (synthesized amount: 2.0 g, yield: 41%) (the structure thereof was identified by LC-MS).

LCMS, calcd for $C_{60}H_{40}N_2$=789, found m/z=789 (M+H$^+$).

Tg: 156.6° C.

Solubility (xylene)>10 wt %

Synthesis Example 3: Synthesis of Compound 1-5

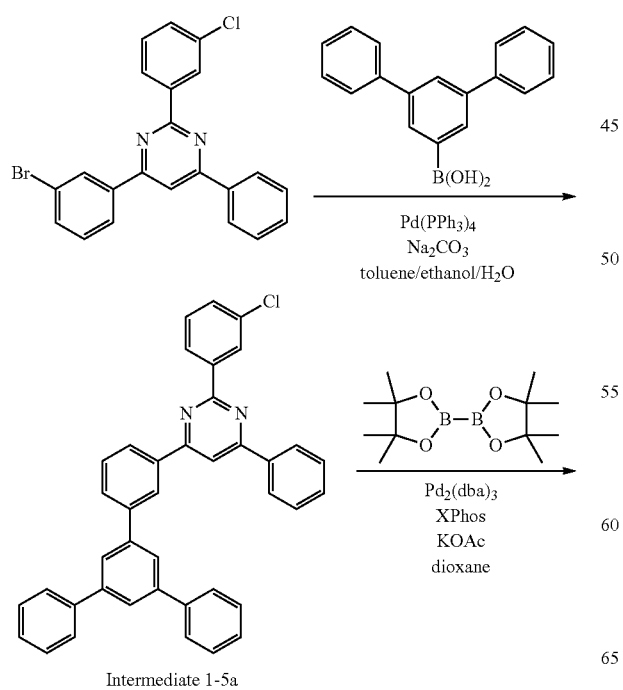

Intermediate 1-5a

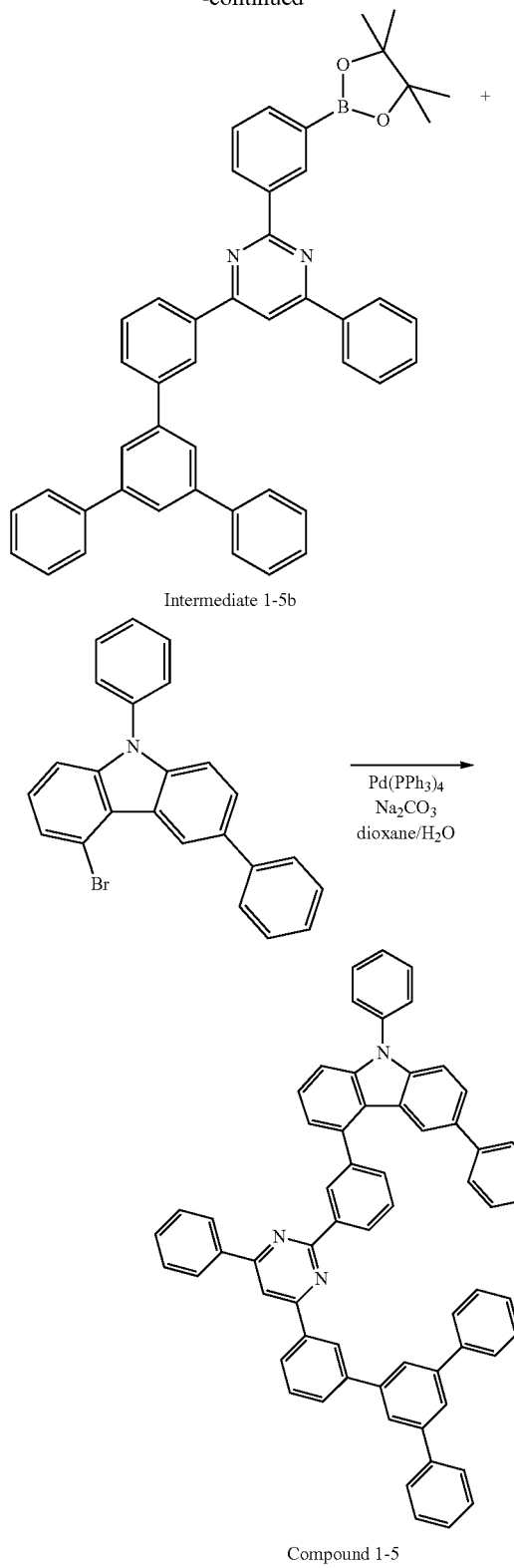

Intermediate 1-5b

Compound 1-5

Synthesis of Intermediate 1-5a 20.0 g (47.4 mmol) of 4-(3-bromophenyl)-2-(3-chlorophenyl)-6-phenylpyrimidine), 20.3 g (56.9 mmol) of a 5'-m- terphenyl boronic acid, 0.91 g (0.79 mmol) of Pd(PPh$_3$)$_4$, and 12.5 g (118 mmol) of sodium carbonate were dissolved in 160 mL of toluene, 250 mL of ethanol, and 200 mL of deionized water in a 200-mL round bottom flask, and the reaction mixture was refluxed for 3 hours in an argon atmosphere. After the reaction, the mixture was poured into 300 mL of pure water, a precipitate was filtered therefrom, and washing thereof was performed by using methanol. A crude solid obtained therefrom was dissolved in toluene, and excess methanol was poured thereinto. A resultant obtained by reprecipitation was dried at a temperature of 40° C. in vacuum for 5 hours, thereby completing the preparation of Intermediate 1-5a (white solid) (synthesized amount: 20.3 g, yield: 75%, purity (HPLC): 99.6%).

Synthesis of Intermediate 1-5b

Intermediate 1-5b (synthesized amount: 20.0 g, yield: 85%, purity (HPLC): 99.9%) was synthesized in the same manner as in Synthesis of Intermediate b of Synthesis Example 2, except that Intermediate 1-5a was used instead of Intermediate b-3.

Synthesis of Compound 1-5

Compound 1-5 (synthesized amount: 3.3 g, yield: 40%, purity (HPLC): 99.95%) was synthesized in the same manner as in Synthesis of Compound 1-7 of Synthesis Example 1, except that Intermediate 1-5b was used instead of Intermediate b.

LCMS, calcd for C$_{64}$H$_{43}$N$_3$=854.07, found m/z=854.3 (M+H$^+$).

Synthesis Example 4: Synthesis of Compound 1-23

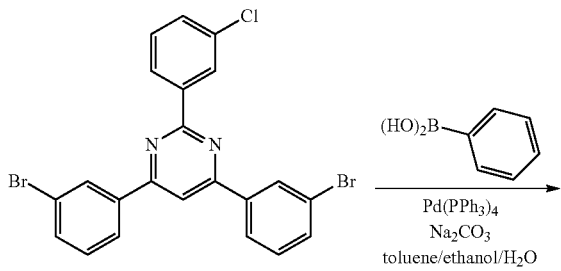

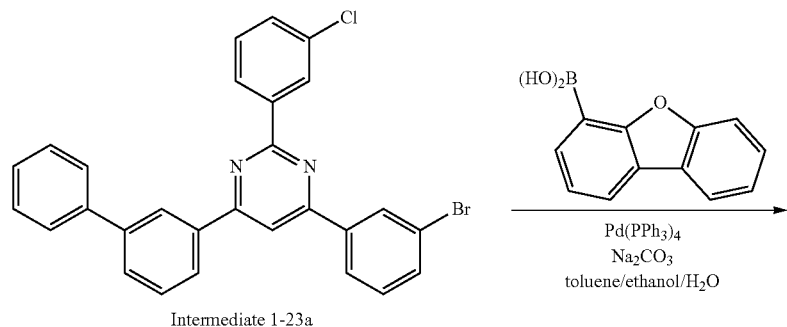

Intermediate 1-23a

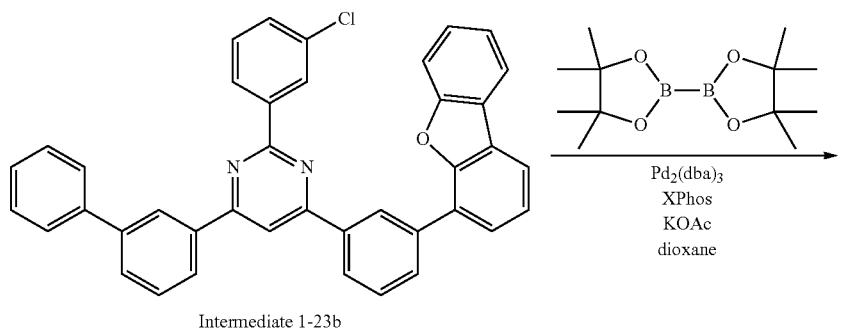

Intermediate 1-23b

-continued

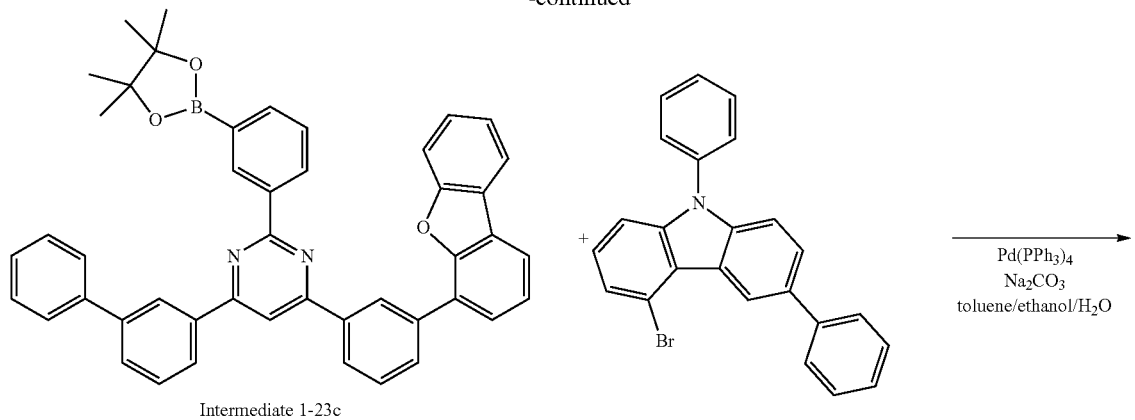

Intermediate 1-23c

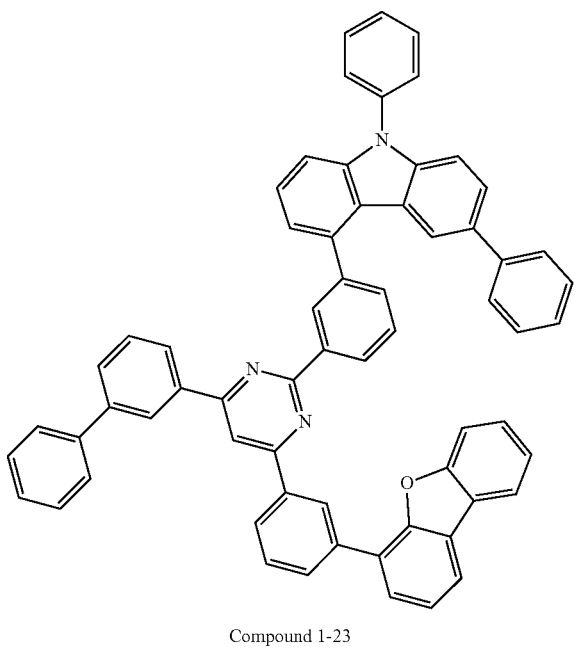 [SMILES: c1ccc(-c2cccc(-c3cc(-c4cccc(-c5cccc6c5oc5ccccc56)c4)nc(-c4cccc(-c5cccc6c5c5cc(-c7ccccc7)ccc5n6-c5ccccc5)c4)n3)c2)cc1]

Compound 1-23

Synthesis of Intermediate 1-23a

Intermediate 1-23a (synthesized amount: 25.1 g, yield: 70%, purity (HPLC): 99.0%) was synthesized in the same manner as in Synthesis of Intermediate 1-5a of Synthesis Example 3, except that 4,6-bis(3-bromophenyl)-2-(3-chlorophenyl)pyrimidine and a phenyl boronic acid were each used instead of 4-(3-bromophenyl)-2-(3-chlorophenyl)-6-phenylpyrimidine and a 5'-m-terphenylboronic acid.

Synthesis of Intermediate 1-23b

Intermediate 1-23b (synthesized amount: 20.3 g, yield: 84%, purity (HPLC): 99.6%) was synthesized in the same manner as in Synthesis of Intermediate 1-5a of Synthesis Example 3, except that Intermediate 1-23a and a dibenzofurane-4-boronic acid were each used instead of 4-(3-bromophenyl)-2-(3-chlorophenyl)-6-phenylpyrimidine and a 5'-m-terphenylboronic acid.

Synthesis of Intermediate 1-23c

Intermediate 1-23c (synthesized amount: 15.0 g, yield: 85%, purity (HPLC): 99.9%) was synthesized in the same manner as in Synthesis of Intermediate b of Synthesis Example 2, except that Intermediate 1-23b was used instead of Intermediate b-3.

Synthesis of Compound 1-23

Compound 1-23 (synthesized amount: 8.0 g, yield: 64%, purity (HPLC): 99.94%) was synthesized in the same manner as in Synthesis of Compound 1-7 of Synthesis Example 1, except that Intermediate 1-23c was used instead of Intermediate b.

Synthesis Example 5: Synthesis of Synthesis of Compound 1-24

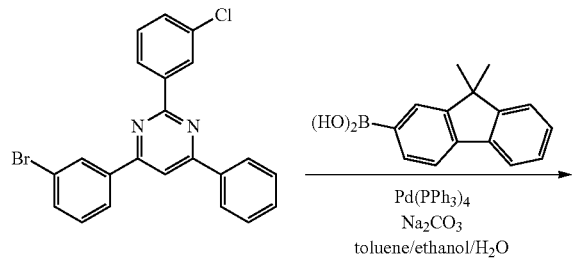

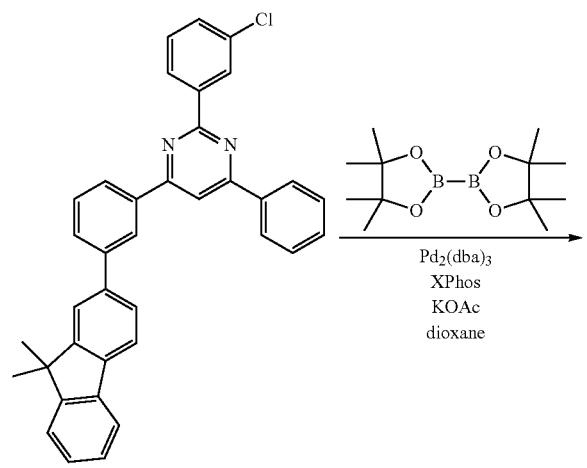

Intermediate 1-24a

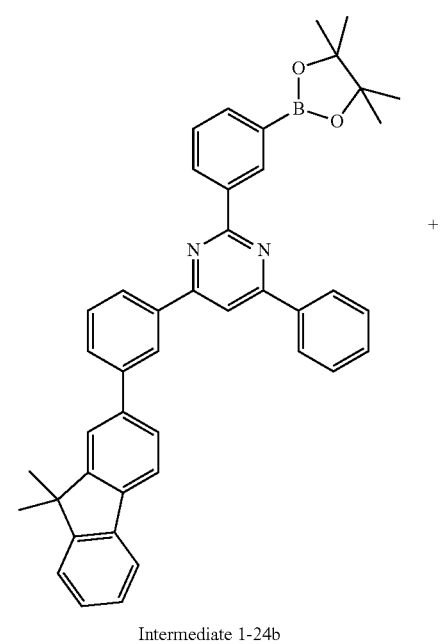

Intermediate 1-24b

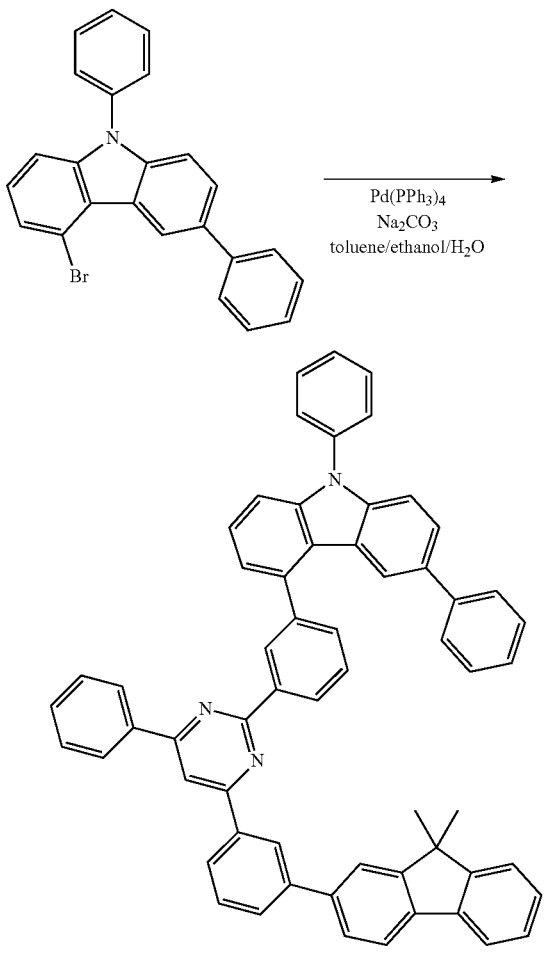

Compound 1-24

Synthesis of Intermediate 1-24a

Intermediate 1-23b (synthesized amount: 20.30 g, yield: 75%, purity (HPLC): 99.6%) was synthesized in the same manner as in Synthesis of Intermediate 1-5a of Synthesis Example 3, except that a 9,9"-dimethylfluorene-3-boronic acid was used instead of the 5'-m-terphenylboronic acid.

Synthesis of Intermediate 1-24b

Intermediate 1-24b (synthesized amount: 23.89 g, yield: 85%, purity (HPLC): 99.9%) was synthesized in the same manner as in Synthesis of Intermediate b of Synthesis Example 2, except that Intermediate 1-24a was used instead of Intermediate b-3.

Synthesis of Compound 1-24

Compound 1-24 (synthesized amount: 8.02 g, yield: 72%, purity (HPLC): 99.92%) was synthesized in the same manner as in Synthesis of Compound 1-7 of Synthesis Example 1, except that Intermediate 1-24b was used instead of Intermediate b.

Synthesis Example 6: Synthesis of Compound 1-79

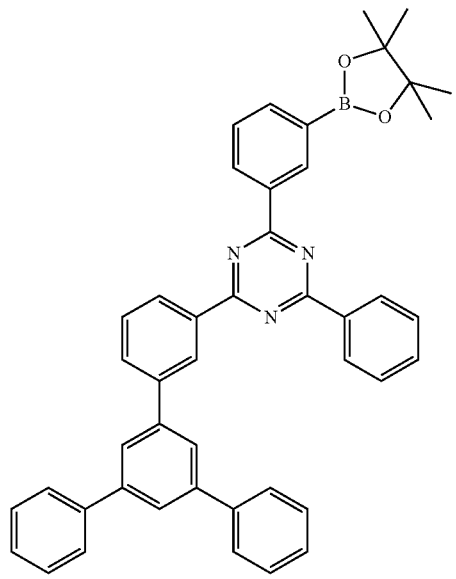

Intermediate b

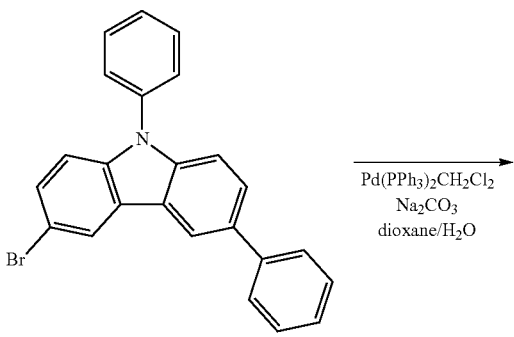

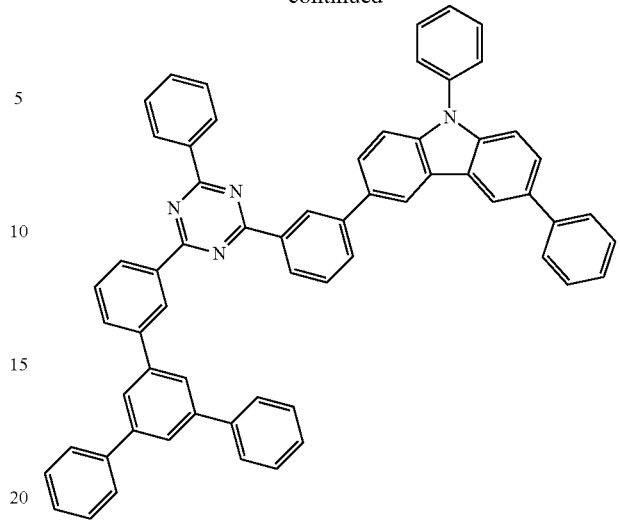

Compound 1-79

Compound 1-79 (synthesized amount: 3.0 g, yield: 68%, purity (HPLC): 99.97%) was synthesized in the same manner as in Synthesis of Compound 1-7 of Synthesis Example 1, except that 3-bromo-6,9-diphenyl-9H-carbazole was used instead of Intermediate a.

LCMS, calcd for $C_{63}H_{42}N_4$=855.06, found m/z=855.3 (M+H$^+$).

Synthesis Example 7: Synthesis of Compound 6-12

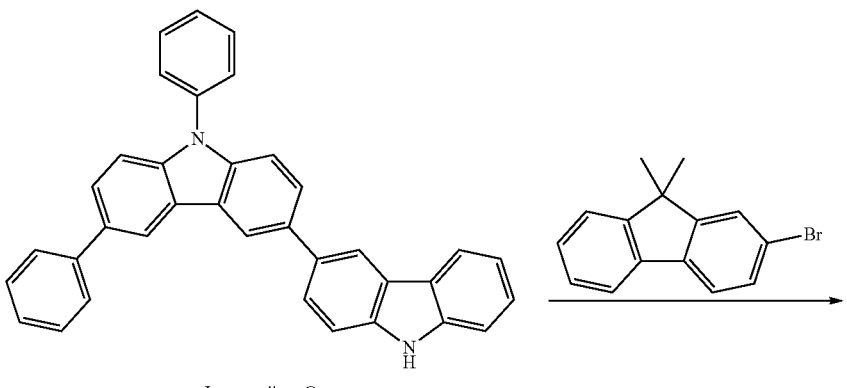

Intermediate C

-continued
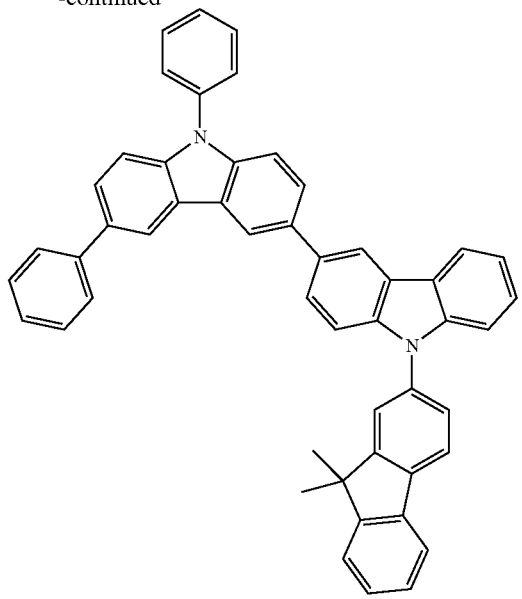
Compound 6-12
Compound 6-12 (synthesized amount: 1.19 g, yield: 43%, purity (HPLC): 99.89%) was synthesized in the same manner as in Synthesis of Compound 6-5 of Synthesis Example 2, except that 2-bromo-9,9''-dimethylfluorene was used instead of 3-bromo-5''-phenyl-1,1'':3'',1'''-terphenyl.
LCMS, calcd for $C_{51}H_{53}N_2$=676.86, found m/z=677.3 (M+H$^+$).
Synthesis Example 8: Synthesis of Compound 6-31
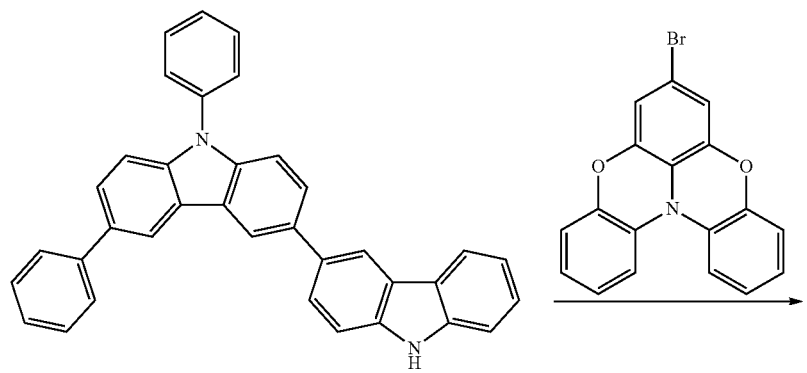
Intermediate C

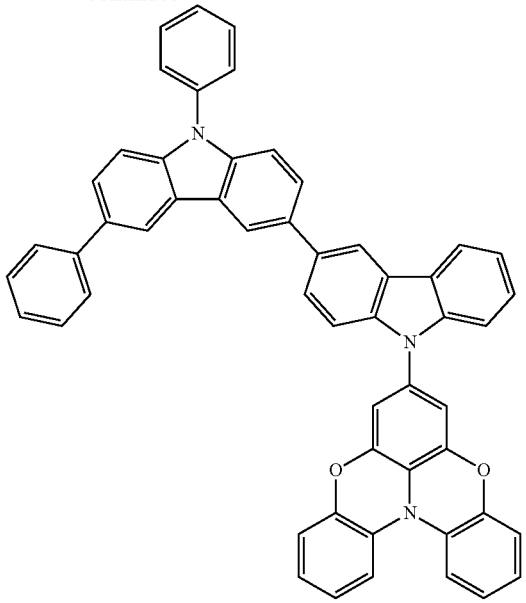

Compound 6-31

Compound 6-31 (synthesized amount: 1.0 g, yield: 55%, purity (HPLC): 99.93%) was synthesized in the same manner as in Synthesis of Compound 6-5 of Synthesis Example 2, except that 7-bromobenzo[5,6][1,4]oxazino[2,3,4-kl]phenoxazine was used instead of 3-bromo-5"-phenyl-1,1":3",1"-terphenyl.

2. Manufacture of Organic Light-Emitting Device

An organic light-emitting device was manufactured by the following processes.

Example 1

Poly(3,4-ethylene dioxythiophene)/poly(4-styrene sulfonate) (PEDOT/PSS) (manufactured by Sigma-Aldrich) were spin-coated on an ITO glass substrate, on which a stripe type ITO layer as a first electrode (anode) was deposited to a thickness of 150 nanometers (nm), and then dried to form a hole injection layer having a thickness of 30 nm.

A mixture containing 1 wt % of poly[(9,9-dioctylfluorenyl-2,7-diyl)-co-(4,4'-(N-(4-sec-butylphenyl)diphenylamine)] (TFB) (manufactured by Sigma-Aldrich) in xylene was spin-coated on the hole injection layer and dried, and then, a thermal treatment was performed at a temperature of 230° C. for 1 hour to form a hole transport layer having a thickness of 30 nm.

A mixture containing Compounds 1-7 and 6-5 (host) and tris(2-(3-p-xylyl)phenyl)pyridine iridium) (III) (dopant) in toluene was spin-coated on the hole transport layer, and then, dried to form an emission layer having a thickness of 30 nm. A weight ratio of Compound 1-7 to Compound 6-5 was 3:7, and an amount of tris(2-(3-p-xylyl)phenyl)pyridine iridium) (III) was 10 wt % based on 100 wt % of the emission layer.

(8-quinolinate)lithium (Liq) and KLET-03 (available from Chemi-pro) were co-deposited on the emission layer in a vacuum deposition apparatus to form an electron transport layer having a thickness of 50 nm, lithium fluoride (LiF) was deposited on the electron transport layer in a vacuum deposition apparatus to form an electron injection layer having a thickness of 1 nm, and aluminum (Al) was deposited on the electron injection layer in a vacuum deposition apparatus to form a second electrode (cathode) having a thickness of 100 nm, thereby completing the manufacture of an organic light-emitting device.

Example 2

An organic light-emitting device of Example 2 was manufactured in the same manner as in Example 1, except that only Compound 1-7 was used as a host material, without using Compound 6-5.

Examples 3 and 4

Organic light-emitting devices of Examples 3 and 4 were manufactured in the same manner as in Example 1, except that Compounds 6-12 and 6-31 were each used instead of Compound 6-5 as a host material.

Comparative Example 1

An organic light-emitting device of Comparative Example 1 was manufactured in the same manner as in Example 1, except that Compounds h-1 and CBP were each used instead of Compounds 1-7 and 6-5 as a host material. Compound h-1 in Table 1 is as follows. Letters described in the materials for the host in Table 1 refer to the numbered Compounds described above.

Compound h-1

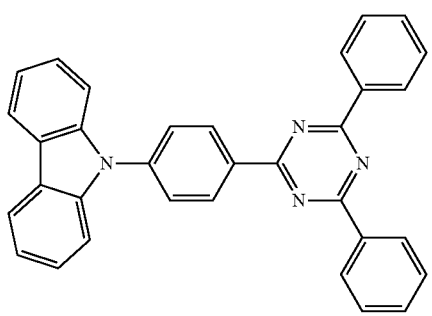

3. Evaluation Results

A. Evaluation of Film-Forming Property

A TBF layer was formed on an ITO glass substrate, on which an ITO layer was deposited to a thickness of 150 nm, in the same manner as in Example 1. Then, a mixture containing 1 wt % of Compounds 1-7 and 6-5 in xylene (weight ratio of Compound 1-7 to Compound 6-5=3:7) was spin-coated on the TBF layer and dried to form a laminated film having a thickness of 30 nm.

The laminated film was thermally treated at a temperature of 125° C. Then, the surface of the laminated film was observed through an optical microscope and the surface state of the laminated film was evaluated based on the following criteria.

○: a uniform state having no defect

Δ: a state in which several dark spots are observed, but a device can be manufactured X: a state in which continuity of a film cannot be secured and a device cannot be manufactured B. Evaluation of Organic Light-Emitting Device The current efficiency and light emission lifespan of the organic light-emitting devices manufactured according to Examples 1 to 4 and Comparative Example 1 were evaluated by the following methods.

Each of the organic light-emitting devices was turned on to emit light by applying a certain voltage thereto by using a DC constant voltage power supply (source meter manufactured by KEYENCE). While the light emission of the organic light-emitting device was measured by a luminance meter (SR-3 manufactured by Topcom), a current gradually increased and a current density was measured when luminance was 6,000 candelas per square meter ($cd/m^2$) and current efficiency was calculated from the current density measured when the current was left constant.

Also, the light emission lifespan ($T_{80}$) indicates an amount of time that lapsed when luminance measured by a luminance meter gradually decreased and was 80% of initial luminance (100%).

Evaluation results are shown in Table 1. The current efficiency and light emission lifespan in Table 1 are relative values when a current efficiency value and a light emission lifespan value of Comparative Example 1 are assumed to be 100.

TABLE 1

| | Host material | Film-forming property | Current efficiency | Light emission lifespan ($T_{80}$) (at 6,000 $cd/m^2$) |
|---|---|---|---|---|
| Example 1 | 1-7:6-5 | ○ | 150 | 260 |
| Example 2 | 1-7 | ○ | 130 | 180 |
| Example 3 | 1-7:6-12 | ○ | 148 | 280 |
| Example 4 | 1-7:6-31 | ○ | 153 | 195 |
| Comparative Example 1 | h-1:CBP | Δ | 100 | 100 |

From the results shown in Table 1, it may be confirmed that the organic light-emitting devices of Examples 1 to 4, which each include the compound represented by Formula (1) as the host material, have equal or higher current efficiency and have a considerably improved light emission lifespan, compared to those of Comparative Example 1. Also, it may be confirmed that, since Compound 1-7 has a glass transition temperature (Tg) of 125° C. or higher and is soluble in a hydrocarbon-based solvent such as toluene or xylene, the compound represented by Formula (1) is suitable as a material for forming an organic light-emitting device for solution coating.

4. Measurement of Glass Transition Temperature and Measurement of Solubility

Examples 5 to 8

The glass transition temperature (Tg) and solubility of Compounds 1-5, 1-23, 1-24, and 1-79 were measured. In measuring the solubility, xylene was used as a solvent. The glass transition temperature (Tg) and solubility of each compound is written under each compound number.

1-5

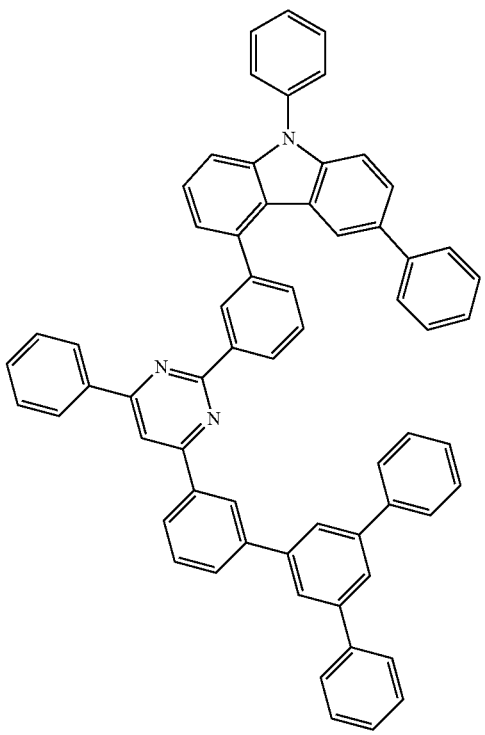

Tg = 143° C.
> 10wt%

1-23

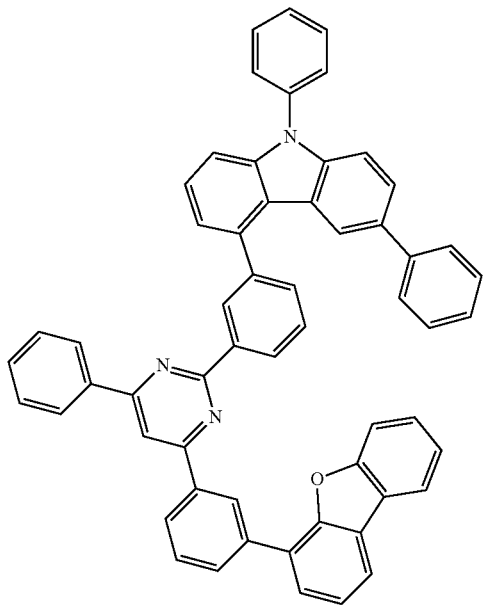

Tg = 137° C.
> 10wt%

1-24

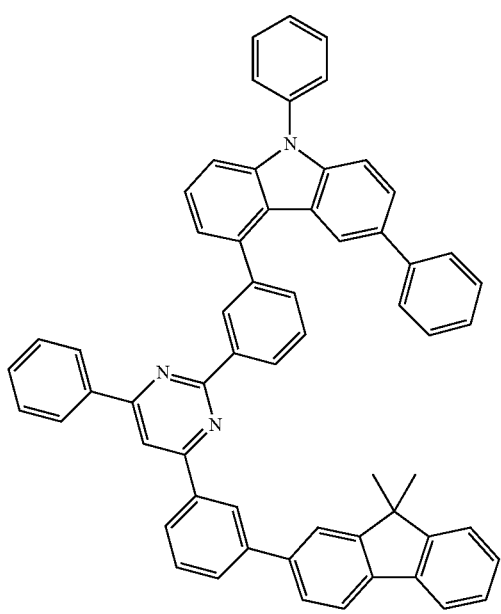

Tg = 144° C.
> 10wt%

1-79

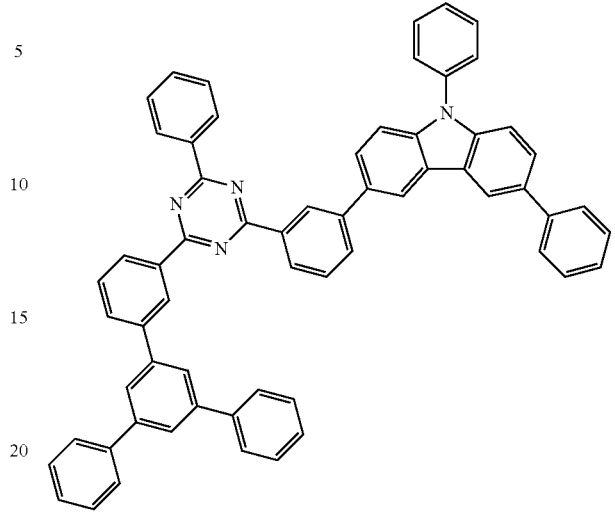

Tg = 139° C.
> 10wt%

From the above, it may be confirmed that Compounds 1-5, 1-23, 1-24, and 1-79 have excellent heat resistance and solubility, and thus, are suitable as a material for forming an organic light-emitting device for solution coating.

By using the condensed cyclic compound described above, the thermal stability of the organic layer may be improved, and thus, the light emission lifespan of the organic light-emitting device may be improved.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. A condensed cyclic compound represented by Formula (1):

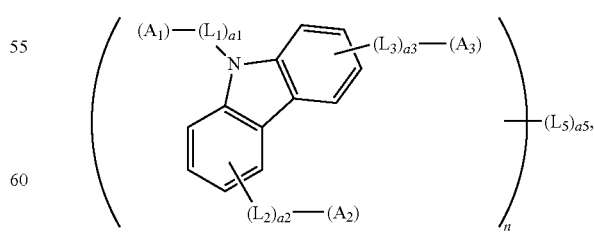

Formula (1)

wherein, in Formula (1),
$L_1$ to $L_3$ are each independently selected from a single bond, a substituted or unsubstituted $C_2$-$C_{60}$ alkylene group, a substituted or unsubstituted $C_3$-$C_{10}$ cycloalkylene group, a substituted or unsubstituted C₁-C₁₀ heterocycloalkylene group, a substituted or unsubstituted C₃-C₁₀ cycloalkenylene group, a substituted or unsubstituted C₁-C₁₀ heterocycloalkenylene group, a substituted or unsubstituted C₆-C₆₀ arylene group, a substituted or unsubstituted C₁-C₆₀ heteroarylene group, a substituted or unsubstituted divalent non-aromatic condensed polycyclic group, and a substituted or unsubstituted divalent non-aromatic condensed heteropolycyclic group, L₅ is selected from:

a single bond, *—C(=O)—*', *—C(=S)—*', and *—N(R₅)—*'; and a phenylene group, an indenylene group, a naphthylene group, an acenaphthylene group, a fluorenylene group, a spiro-bifluorenylene group, a phenanthrenylene group, an anthracenylene group, a fluoranthrenylene group, a triphenylenylene group, a pyrenylene group, a chrysenylene group, a pyrrolylene group, an imidazolylene group, a pyrazolylene group, a triazolylene group, a pyridinylene group, a pyrazinylene group, a pyrimidinylene group, a pyridazinylene group, a triazinylene group, a furanylene group, a thienylene group, an oxazolylene group, an isoxazolylene group, a thiazolylene group, an isothiazolylene group, an oxadiazolylene group, an isoxadiazolylene group, a thiadiazolylene group, an isothiadiazolylene group, a pyrenylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoxazolylene group, a benzothiazolylene group, a benzimidazolylene group, an isoindolylene group, an indolylene group, a benzofuranylene group, a benzothiophenylene group, a benzocarbazolylene group, a naphthobenzofuranylene group, a naphthobenzothiophenylene group, an imidazopyrimidinylene group, and an imidazopyridinylene group, each unsubstituted or substituted with at least one selected from deuterium, —F, -CD₃, -CD₂H, -CDH₂, —CF₃, —CF₂H, —CFH₂, —NCS, a cyano group, a C₁-C₂₀ alkyl group, a C₁-C₂₀ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group,

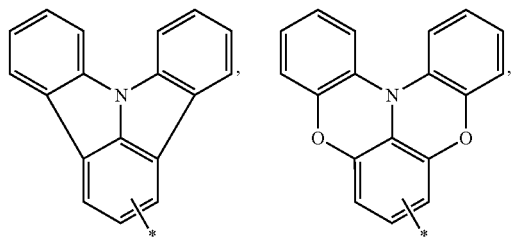

—Si(Q₃₁)(Q₃₂)(Q₃₃), —N(Q₃₁)(Q₃₂), and —C(=O)(Q₃₁), and

* and *' each indicate a binding site to a neighboring atom, a1 to a3 and a5 are each independently an integer selected from 1 to 10, (L₅)ₐ₅ is an n-valent linking group or a single bond, wherein n is a natural number greater than or equal to one, when n is one, (L₅)ₐ₅ does not exist, when n is a natural number greater than or equal to two, at least one of *-(L₁)ₐ₁-(A₁), *-(L₂)ₐ₂-(A₂), and *-(L₃)ₐ₃-(A₃) is linked to (L₅)ₐ₅ or is a single bond linked to (L₅)ₐ₅, i) A₁ to A₃ and R₅ are each independently linked to (L₅)ₐ₅;

ii) A₁ to A₃ and R₅ are each independently a single bond linked to (L₅)ₐ₅;

iii) A₁ to A₃ and R₅ are each independently a group represented by one of Formulae (2) to (5); or iv) A₁ to A₃ and R₅ are each independently selected from a phenyl group, an indenyl group, a naphthyl group, an acenaphthyl group, a fluorenyl group, a spiro-bifluorenyl group, a phenanthrenyl group, an anthracenyl group, a fluoranthenyl group, a triphenylenyl group, a pyrenyl group, a chrysenyl group, a pyrrolyl group, a furanyl group, a thienyl group, an isoindolyl group, an indolyl group, a benzofuranyl group, a benzothiophenyl group, a benzocarbazolyl group, a naphthobenzofuranyl group, and a naphthobenzothiophenyl group, each unsubstituted or substituted with at least one selected from deuterium, -CD₃, -CD₂H, -CDH₂, a C₁-C₂₀ alkyl group, a C₁-C₂₀ alkoxy group, a phenyl group, a biphenyl group, a fluorenyl group, a spiro-bifluorenyl group, a dimethylfluorenyl group, a diphenylfluorenyl group,

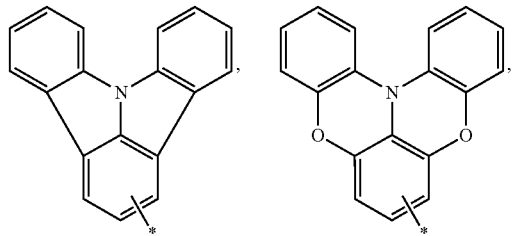

a group represented by *-(L₂)ₐ₂-(A₂) is linked to a third or fourth carbon of a carbazole core of Formula (1), a group represented by *-(L₃)ₐ₃-(A₃) is linked to a fifth or sixth carbon of the carbazole core of Formula (1), and * in the group represented by *-(L₂)ₐ₂-(A₂) and the group represented by *-(L₃)ₐ₃-(A₃) indicates a binding site to a carbon atom of the carbazole core of Formula (1), and provided that, $A_2$ is a group represented by one of Formulae (2) to (5) and $A_3$ is not a group represented by one of Formulae (3) and (4):

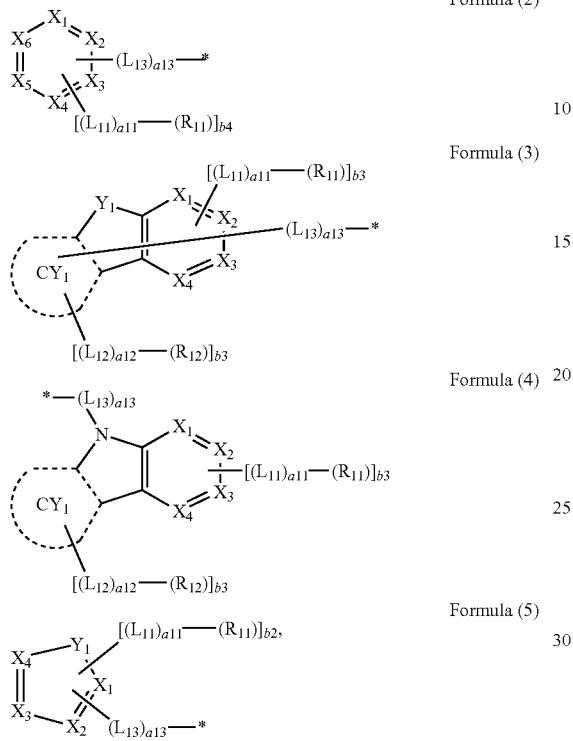

Formula (2)
Formula (3)
Formula (4)
Formula (5)

wherein, in Formulae (2) to (5), $X_1$ is N, carbon linked to $*-(L_{11})_{a11}-(R_{11})$, or carbon linked to $L_{13}$, $X_2$ is N, carbon linked to $*-(L_{11})_{a11}-(R_{11})$, or carbon linked to $L_{13}$, $X_3$ is N, carbon linked to $*-(L_{11})_{a11}-(R_{11})$, or carbon linked to $L_{13}$, $X_4$ is N, carbon linked to $*-(L_{11})_{a11}-(R_{11})$, or carbon linked to $L_{13}$, $X_5$ is N, carbon linked to $*-(L_{11})_{a11}-(R_{11})$, or carbon linked to $L_{13}$, $X_6$ is N, carbon linked to $*-(L_{11})_{a11}-(R_{11})$, or carbon linked to $L_{13}$, provided that $X_1$ to $X_4$ in Formula (4) are not carbon linked to $L_{13}$, $Y_1$ is O, S, $N(R_{13})$, or $C(R_{14})(R_{15})$, and $R_{14}$ and $R_{15}$ are optionally linked to form a saturated or unsaturated ring, $CY_1$ is a $C_5$-$C_{30}$ carbocyclic group or a $C_2$-$C_{30}$ heterocyclic group, at least one of $X_1$ to $X_6$ in Formula (2) is N, in Formulae (3) and (4), at least one of $X_1$ to $X_4$ is N, or $CY_1$ is a π electron-depleted nitrogen-containing $C_2$-$C_{30}$ heterocyclic group, at least one of $X_1$ to $X_4$ in Formula (5) is N, $L_{11}$ to $L_{13}$ are each independently selected from a single bond, a substituted or unsubstituted $C_1$-$C_{60}$ alkylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a11 to a13 are each independently an integer selected from 1 to 10, $R_{11}$ to $R_{15}$ are each independently selected from hydrogen, deuterium, —F, —Cl, —Br, —I, $-CD_3$, $-CD_2H$, $-CDH_2$, $-CF_3$, $-CF_2H$, $-CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $—Si(Q_1)(Q_2)(Q_3)$, $—N(Q_1)(Q_2)$, and $—C(=O)(Q_1)$, provided that $R_{11}$ in Formula (2) is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, b2 is an integer from 0 to 2, b3 is an integer from 0 to 3, b4 is an integer from 01 to 4, indicates a binding site to a neighboring atom, and wherein the group represented by $*-(L_2)_{a2}-(A_2)$ and the group represented by $*-(L_3)_{a3}-(A_3)$ are linked to the carbazole core, such that a linking position of the group represented by $*-(L_2)_{a2}-(A_2)$ and the carbazole core is asymmetric to a linking position of the group represented by $*-(L_3)_{a3}-(A_3)$ and the carbazole core with respect to a reverse central axis passing through a nitrogen atom of the carbazole core of Formula (1), and at least one substituent of the substituted $C_2$-$C_{60}$ alkylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group in Formulae (1) to (5) is selected from:

deuterium, —F, —Cl, —Br, —I, -CD$_3$, -CD$_2$H, -CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, -CD$_3$, -CD$_2$H, -CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si(Q$_{11}$)(Q$_{12}$)(Q$_{13}$), —N(Q$_{11}$)(Q$_{12}$), and —C(=O)(Q$_{11}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, -CD$_3$, -CD$_2$H, -CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si(Q$_{21}$)(Q$_{22}$)(Q$_{23}$), —N(Q$_{21}$)(Q$_{22}$), and —C(=O)(Q$_{21}$); and —Si(Q$_{31}$)(Q$_{32}$)(Q$_{33}$), —N(Q$_{31}$)(Q$_{32}$), and —C(=O)(Q$_{31}$), wherein Q$_1$ to Q$_3$, Q$_{11}$ to Q$_{13}$, Q$_{21}$ to Q$_{23}$, and Q$_{31}$ to Q$_{33}$ are each independently selected from hydrogen, deuterium, a $C_1$-$C_{20}$ alkyl group, a $C_1$-$C_{20}$ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, and a diphenyldibenzothiophenyl group.

2. The condensed cyclic compound of claim 1, wherein L$_1$ to L$_3$ are each independently selected from:

a single bond; and a phenylene group, an indenylene group, a naphthylene group, an acenaphthylene group, a fluorenylene group, a spiro-bifluorenylene group, a phenanthrenylene group, an anthracenylene group, a fluoranthrenylene group, a triphenylenylene group, a pyrenylene group, a chrysenylene group, a pyrrolylene group, a furanylene group, a thienylene group, an isoindolylene group, an indolylene group, a benzofuranylene group, a benzothiophenylene group, a carbazolylene group, a dibenzofuranylene group, a dibenzothiophenylene group, a benzocarbazolylene group, a naphthobenzofuranylene group, and a naphthobenzothiophenylene group, each unsubstituted or substituted with at least one selected from deuterium, -CD$_3$, -CD$_2$H, -CDH$_2$, a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group,

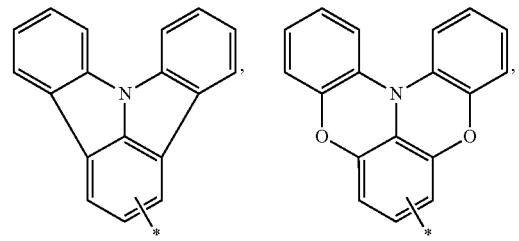

—Si(Q$_{31}$)(Q$_{32}$)(Q$_{33}$), —N(Q$_{31}$)(Q$_{32}$), and —C(=O)(Q$_{31}$), and L$_{11}$ to L$_{13}$ are each independently selected from a phenylene group, an indenylene group, a naphthylene group, an acenaphthylene group, a fluorenylene group, a spiro-bifluorenylene group, a phenanthrenylene group, an anthracenylene group, a fluoranthrenylene group, a triphenylenylene group, a pyrenylene group, a chrysenylene group, a pyrrolylene group, an imidazolylene group, a pyrazolylene group, a triazolylene group, a pyridinylene group, a pyrazinylene group, a pyrimidinylene group, a pyridazinylene group, a triazinylene group, a furanylene group, a thienylene group, an oxazolylene group, an isoxazolylene group, a thiazolylene group, an isothiazolylene group, an oxadiazolylene group, an isoxadiazolylene group, a thiadiazolylene group, an iso-thiadiazolylene group, a pyranylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzoxazolylene group, a benzothiazolylene group, a benzimidazolylene group, an isoindolylene group, an indolylene group, a benzofuranylene group, a benzothiophenylene group, a carbazolylene group, a dibenzofuranylene group, a dibenzothiophenylene group, a benzocarbazolylene group, a naphthobenzofuranylene group, a naphthobenzothiophenylene group, an imidazopyrimidinylene group, and an imidazopyridinylene group, each unsubstituted or substituted with at least one selected from deuterium, —F, -CD$_3$, -CD$_2$H, -CDH$_2$, —CF$_3$, —CF$_2$H, —CFH$_2$, —NCS, a cyano group, a C$_1$-C$_{20}$ alkyl group, a C$_1$-C$_{20}$ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group,

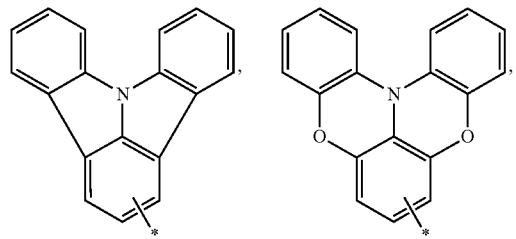

—Si(Q$_{31}$)(Q$_{32}$)(Q$_{33}$), —N(Q$_{31}$)(Q$_{32}$), and —C(=O)(Q$_{31}$).

3. The condensed cyclic compound of claim 1, wherein (L$_5$)$_{a5}$ is a group represented by *—Ar$_1$-T$_1$-Ar$_2$—*', and n is two, and Ar$_1$, T$_1$, and Ar$_2$ are the same as described in connection with L$_5$ in claim 1, provided that Ar$_1$ and Ar$_2$ are not a single bond, *—C(=O)—*', *—C(=S)—*', *—O—*', *—S—*', or *—N(R$_5$)—*'.

4. The condensed cyclic compound of claim 1, wherein R$_{11}$ to R$_{15}$ are each independently selected from:
hydrogen, deuterium, —F, -CD$_3$, -CD$_2$H, -CDH$_2$, —CF$_3$, —CF$_2$H, —CFH$_2$, —NCS, a cyano group, a C$_1$-C$_{20}$ alkyl group, and a C$_1$-C$_{20}$ alkoxy group; and
a phenyl group, an indenyl group, a naphthyl group, an acenaphthyl group, a fluorenyl group, a spiro-bifluorenyl group, a phenanthrenyl group, an anthracenyl group, a fluoranthenyl group, a triphenylenyl group, a pyrenyl group, a chrysenyl group, a pyrrolyl group, an imidazolyl group, a pyrazolyl group, a triazolyl group, a pyridinyl group, a pyrazinyl group, a pyrimidinyl group, a pyridazinyl group, a triazinyl group, a furanyl group, a thienyl group, an oxazolyl group, an isoxazolyl group, a thiazolyl group, an isothiazolyl group, an oxadiazolyl group, an isoxadiazolyl group, a thiadiazolyl group, an isothiadiazolyl group, a pyranyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzothiazolyl group, a benzimidazolyl group, an isoindolyl group, an indolyl group, a benzofuranyl group, a benzothiophenyl group, a carbazolyl group, a dibenzofuranyl group, a dibenzothiophenyl group, a benzocarbazolyl group, a naphthobenzofuranyl group, a naphthobenzothiophenyl group, an imidazopyrimidinyl group, and an imidazopyridinyl group, each unsubstituted or substituted with at least one selected from deuterium, —F, -CD$_3$, -CD$_2$H, -CDH$_2$, —CF$_3$, —CF$_2$H, —CFH$_2$, —NCS, a cyano group, a C$_1$-C$_{20}$ alkyl group, a C$_1$-C$_{20}$ alkoxy group, a phenyl group, a pyridinyl group, a pyrimidinyl group, a triazinyl group, a biphenyl group, a phenylpyridinyl group, a phenylpyrimidinyl group, a phenyltriazinyl group, a diphenylpyridinyl group, a diphenylpyrimidinyl group, a diphenyltriazinyl group, a pyridinylphenyl group, a dipyridinylphenyl group, a pyrimidinylphenyl group, a dipyrimidinylphenyl group, a triazinylphenyl group, a ditriazinylphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, a diphenyldibenzothiophenyl group,

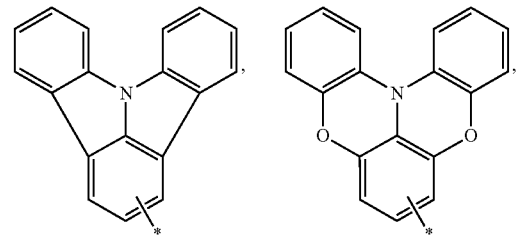

—Si(Q$_{31}$)(Q$_{32}$)(Q$_{33}$), —N(Q$_{31}$)(Q$_{32}$), and —C(=O)(Q$_{31}$).

5. The condensed cyclic compound of claim 1, wherein n is two and (L$_5$)$_{a5}$ is a divalent linking group.

6. The condensed cyclic compound of claim 1, wherein CY$_1$ in Formulae (3) and (4) is a benzene group, a pyridine group, a pyrimidine group, a pyrazine group, or a pyridazine group.

7. The condensed cyclic compound of claim 1, wherein the group represented by Formula (2) is selected from groups represented by Formulae (2)-1 to (2)-7:

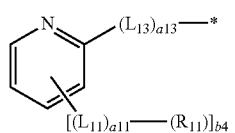
Formula (2)-1

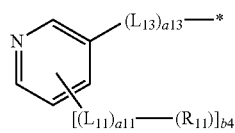
Formula (2)-2

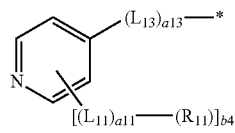
Formula (2)-3

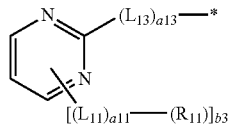
Formula (2)-4

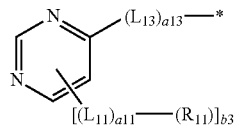
Formula (2)-5

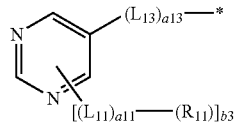
Formula (2)-6

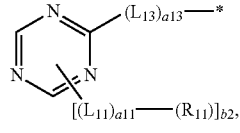
Formula (2)-7 wherein, in Formulae (2)-1 to (2)-7, $L_{11}$, $L_{13}$, a11, a13, and $R_{11}$ are each independently the same described in claim 1, b4 is an integer selected from 1 to 4, b3 is an integer selected from 0 to 3, b2 is an integer selected from 0 to 2, and

* indicates a binding site to a neighboring atom.

8. The condensed cyclic compound of claim 1, wherein a core represented by

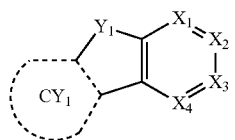

in Formula (3) is selected from groups represented by Formulae 3-1 to 3-20, a core represented by

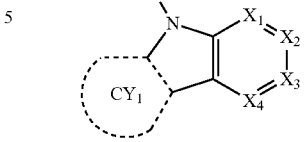

in Formula (4) is selected from groups represented by Formulae 4-1 to 4-10, and a core represented by

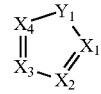

in Formula (5) is selected from groups represented by Formulae 5-1 to 5-6:

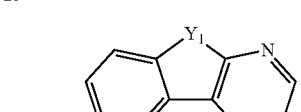
3-1

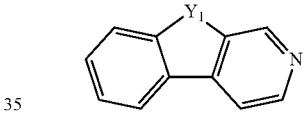
3-2

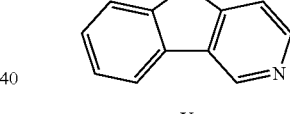
3-3

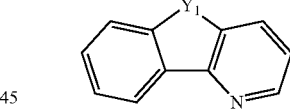
3-4

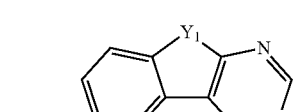
3-5

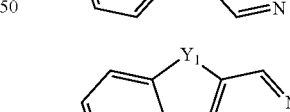
3-6

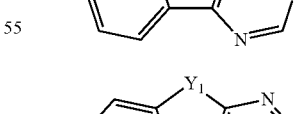
3-7

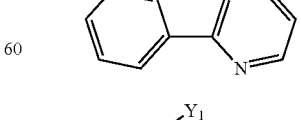
3-8

193
-continued
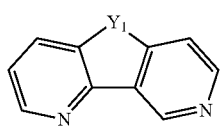
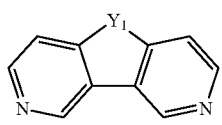
3-11
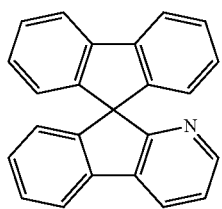
3-12
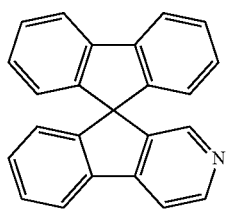
3-13
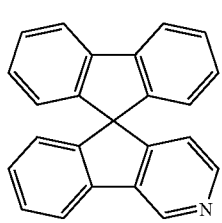
3-14
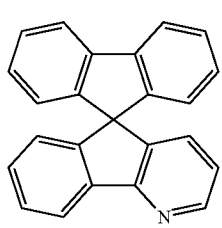
3-15
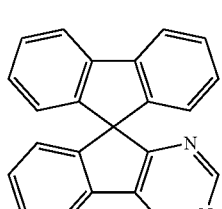
3-16
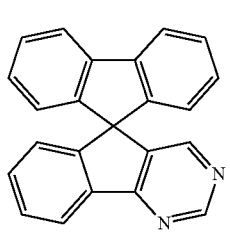
194
-continued
3-9
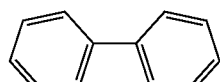
3-10
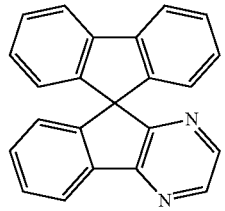
3-17
3-18
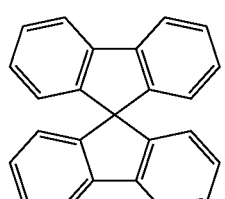
3-19
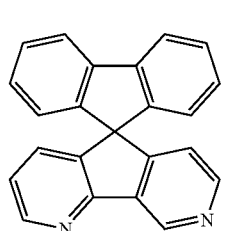
3-20
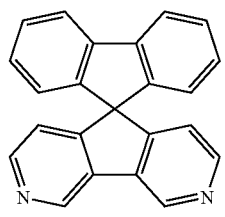
4-1
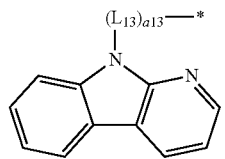
4-2
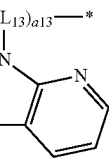
4-3
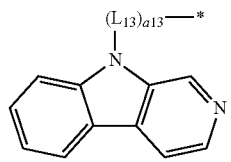
4-4
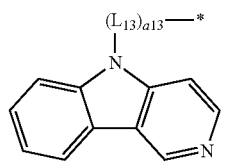

-continued

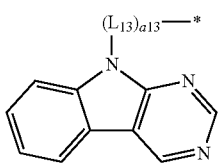
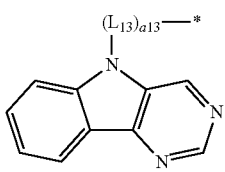
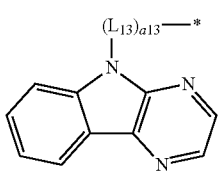
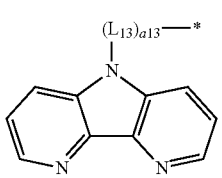
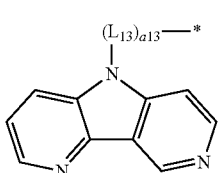
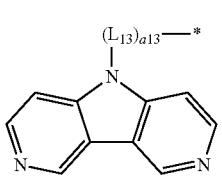

-continued

wherein $Y_1$ in Formulae 3-1 to 3-20, 4-1 to 4-10, and 5-1 to 5-6 are the same as described in claim 1.

9. The condensed cyclic compound of claim 1, wherein the group represented by Formula (3) is selected from groups represented by Formulae (3)-1 to (3)-11, and the group represented by Formula (4) is selected from groups represented by Formulae (4)-1 and (4)-2:

Formula (3)-1
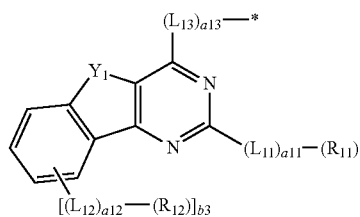

Formula (3)-2
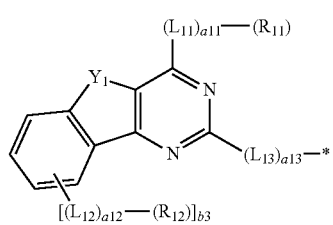

Formula (3)-3
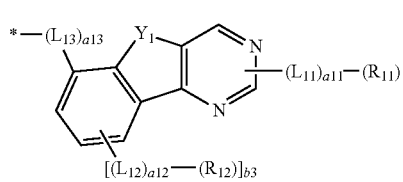

Formula (3)-4
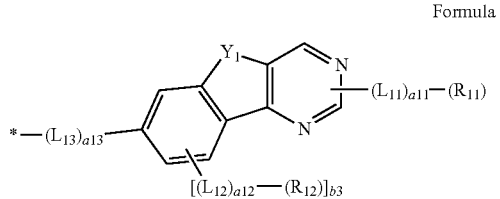

Formula (3)-5
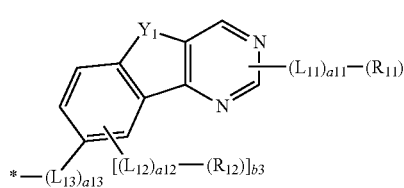

Formula (3)-6
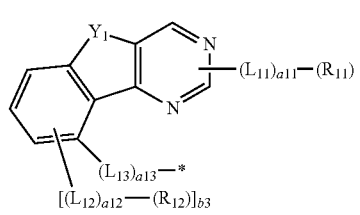

-continued

Formula (3)-7
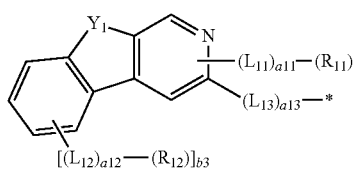

Formula (3)-8
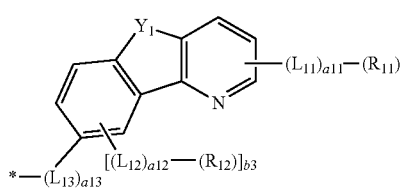

Formula (3)-9
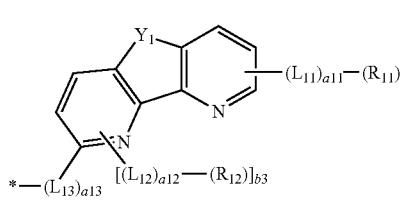

Formula (3)-10
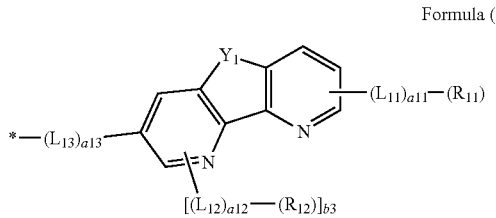

Formula (3)-11
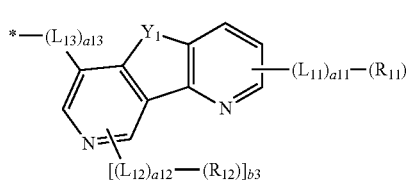

Formula (4)-1
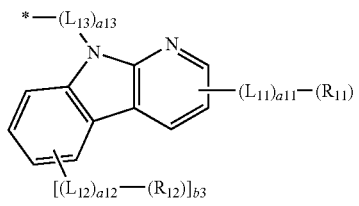

Formula (4)-2
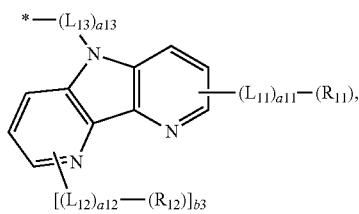

wherein, in Formulae (3)-1 to (3)-11, (4)-1, and (4)-2, $L_{11}$ to $L_{13}$, a11 to a13, $R_{11}$, $R_{12}$, and $Y_1$ are each independently the same as described in claim 1, b2 is an integer selected from 0 to 2, b3 is an integer selected from 0 to 3, and

* indicates a binding site to a neighboring atom.

10. The condensed cyclic compound of claim 1, wherein, in Formula (1),

1) $A_2$ is selected from groups represented by Formulae (2) to (5), and
   i) the groups represented by *-$(L_1)_{a1}$-$(A_1)$ and *-$(L_3)_{a3}$-$(A_3)$ are each independently linked to $(L_5)_{a5}$;
   ii) the groups represented by *-$(L_1)_{a1}$-$(A_1)$ and *-$(L_3)_{a3}$-$(A_3)$ are a single bond linked to $(L_5)_{a5}$; or
   iii) the groups represented by *-$(L_1)_{a1}$-$(A_1)$ and *-$(L_3)_{a3}$-$(A_3)$ are each independently selected from groups represented by Formulae 7-1 to 7-29, 2) $A_1$ and $A_2$ are each independently selected from groups represented by Formulae (2) to (5), and
   i) the group represented by *-$(L_3)_{a3}$-$(A_3)$ is linked to $(L_5)_{a5}$;
   ii) the group represented by *-$(L_3)_{a3}$-$(A_3)$ is a single bond linked to $(L_5)_{a5}$; or
   iii) the group represented by *-$(L_3)_{a3}$-$(A_3)$ is selected from groups represented by Formulae 7-1 to 7-29, 3) $A_2$ is selected from groups represented by Formulae (2) to (5) and $A_3$ is selected from groups represented by Formulae (2) and (5), and
   i) the group represented by *-$(L_1)_{a1}$-$(A_1)$ is linked to $(L_5)_{a5}$;
   ii) the group represented by *-$(L_1)_{a1}$-$(A_1)$ is a single bond linked to $(L_5)_{a5}$; or
   iii) the group represented by *-$(L_1)_{a1}$-$(A_1)$ is selected from groups represented by Formulae 7-1 to 7-29, or 4) $A_1$ and $A_2$ are each independently selected from Formulae (2) to (5) and $A_3$ is selected from groups represented by Formulae (2) and (5), and the groups represented by *-$(L_{11})_{a11}$-$(R_{11})$ and *-$(L_{12})_{a12}$-$(R_{12})$ in Formulae (2) to (5) are each independently selected from groups represented by Formulae 7-1 to 7-57:

7-1
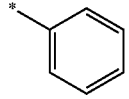

7-2
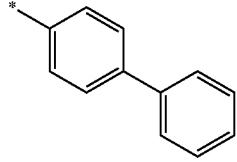

7-3
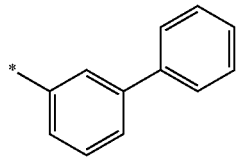

7-4
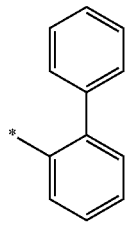

-continued
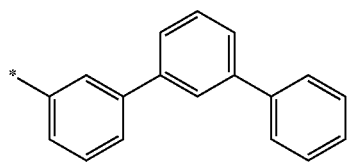
7-5
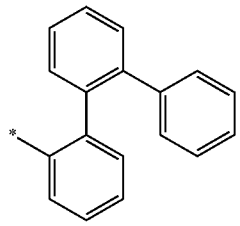
7-6
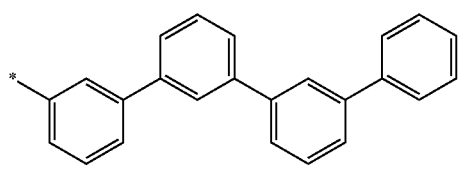
7-7
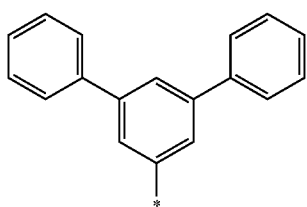
7-8
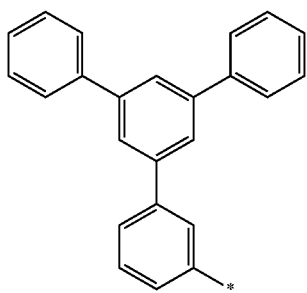
7-9
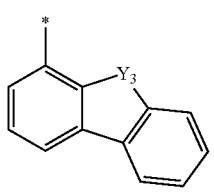
7-10
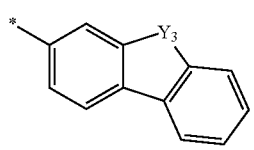
7-11
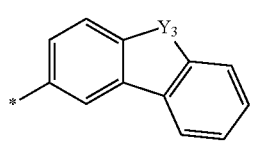
7-12
-continued
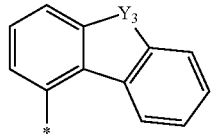
7-13
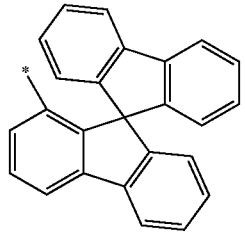
7-14
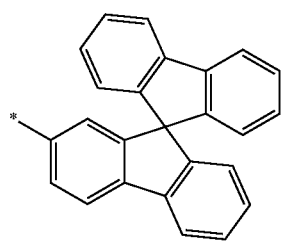
7-15
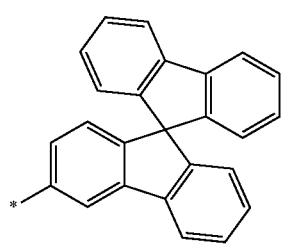
7-16
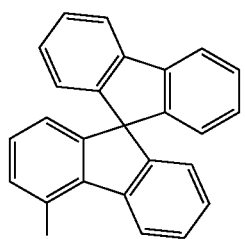
7-17
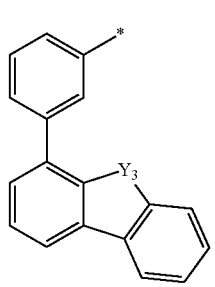
7-18

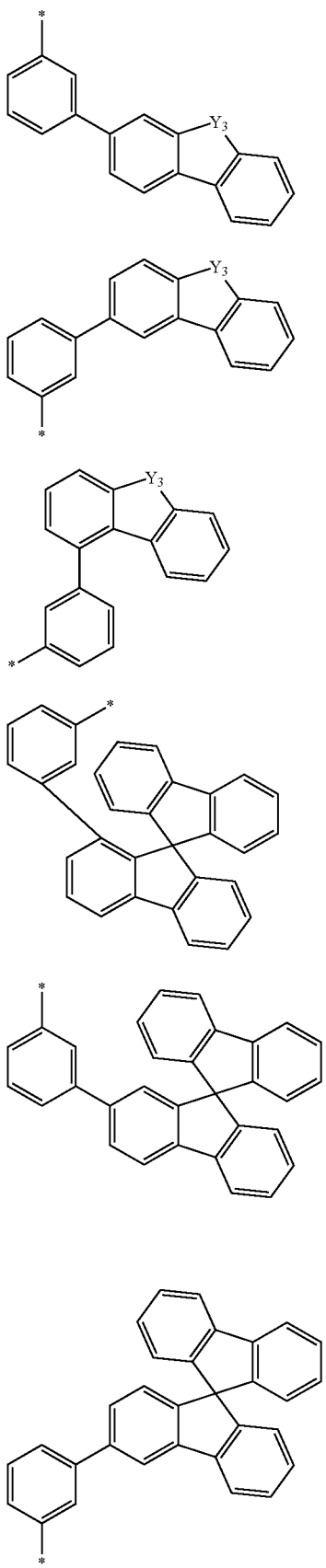
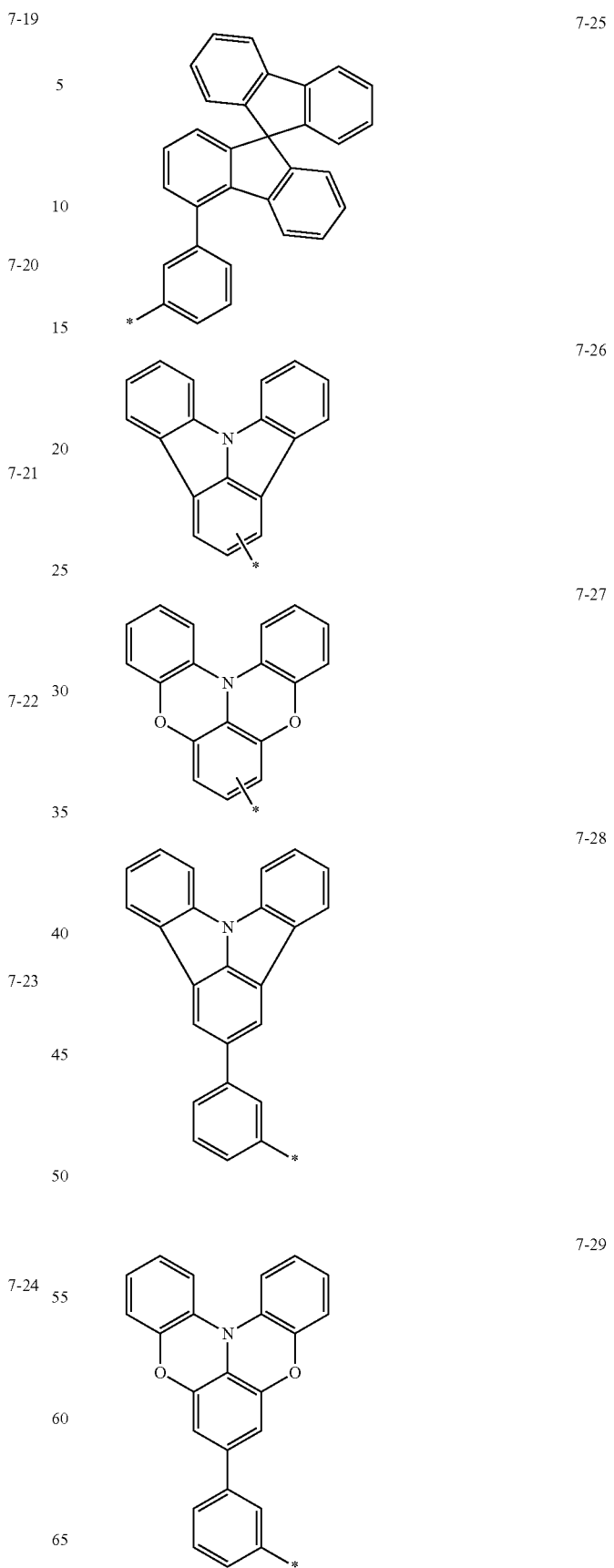

7-30 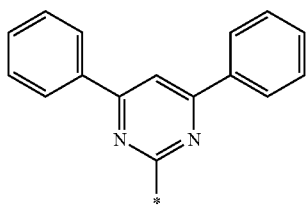
7-31 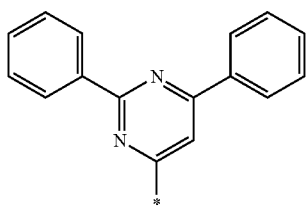
7-32 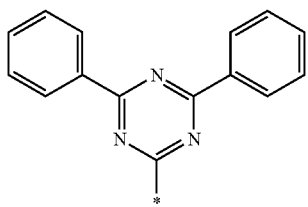
7-33 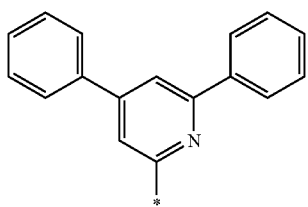
7-34 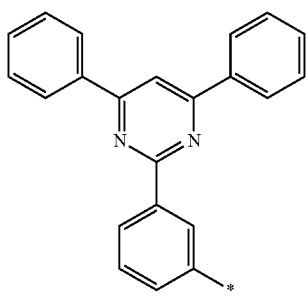
7-35 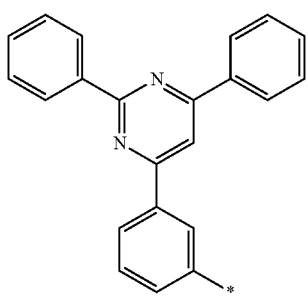
7-36 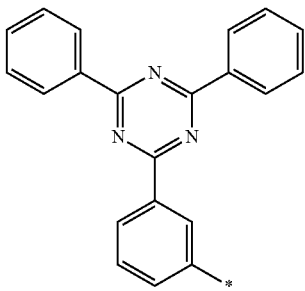
7-37 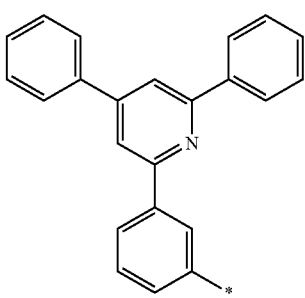
7-38 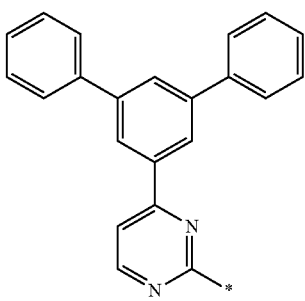
7-39 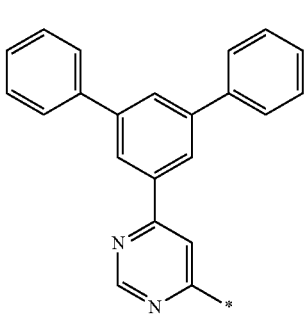
7-40 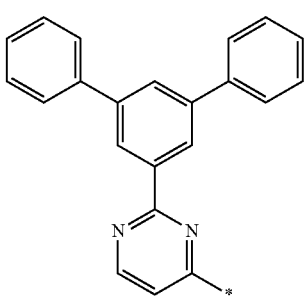

7-41
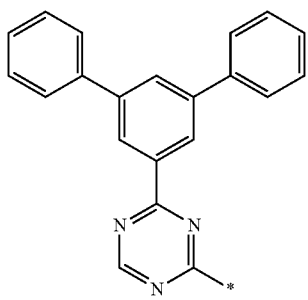
7-42
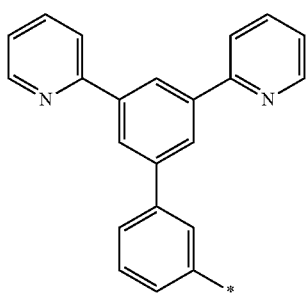
7-43
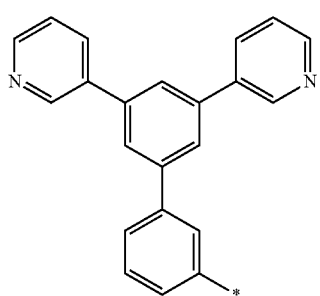
7-44
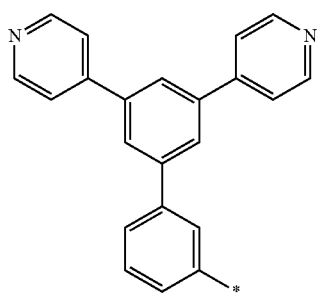
7-45
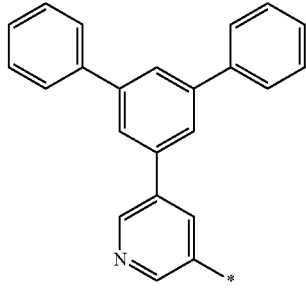
7-46
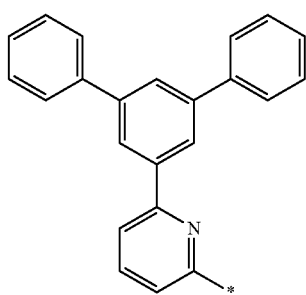
7-47
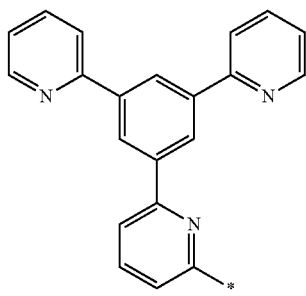
7-48
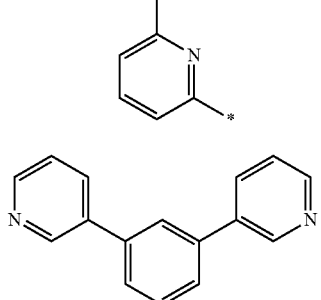
7-49
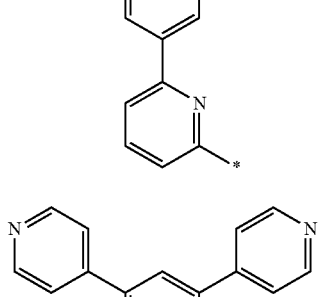
7-50

7-51 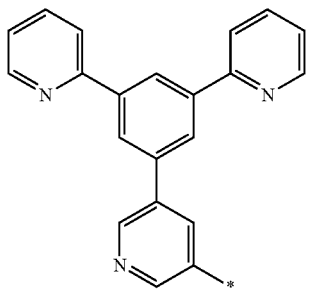

7-52 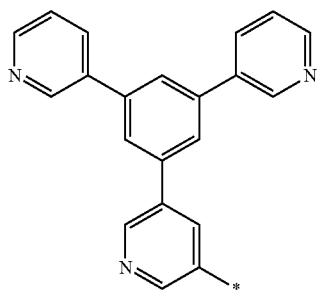

7-53 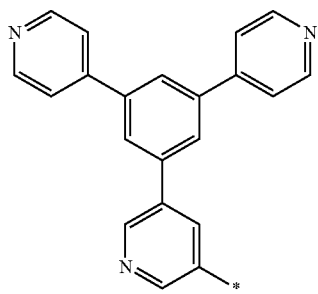

7-54 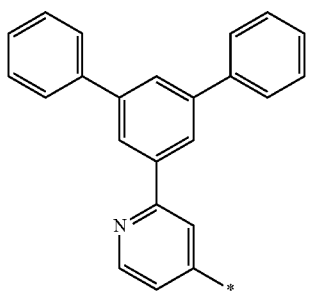

7-55 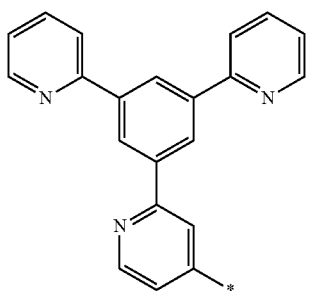

7-56 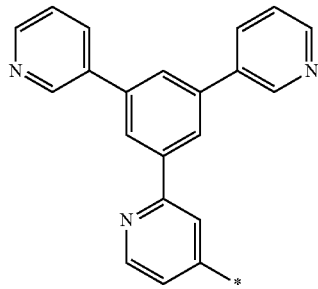

7-57 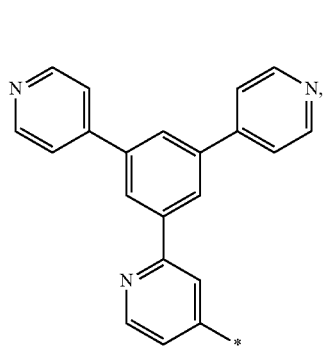

wherein, in Formulae 7-1 to 7-57, $Y_3$ is O, S, $C(Z_{13})(Z_{14})$, or $N(Z_{15})$, $Z_{13}$ to $Z_{15}$ are each independently selected from -CD$_3$, -CD$_2$H, -CDH$_2$, a $C_1$-$C_{20}$ alkyl group, a $C_1$-$C_{20}$ alkoxy group, a phenyl group, and a biphenyl group, and

* indicates a binding site to a neighboring atom.

11. The condensed cyclic compound of claim 1, wherein the condensed cyclic compound has a glass transition temperature of about 125° C. or higher.

12. The condensed cyclic compound of claim 1, wherein a solubility of the condensed cyclic compound to toluene or xylene at 1 atmosphere and 25° C. is about 1 percent by weight or more.

13. A composition comprising:

the condensed cyclic compound of claim 1; and a liquid medium.

14. An organic light-emitting device comprising:

a first electrode;

a second electrode; and an organic layer disposed between the first electrode and the second electrode, wherein the organic layer comprises an emission layer, and wherein the organic layer comprises a layer comprising the condensed cyclic compound of claim 1.

15. The organic light-emitting device of claim 14, wherein the layer comprising the condensed cyclic compound is the emission layer.

16. The organic light-emitting device of claim 15, wherein the emission layer further comprises a condensed cyclic compound represented by Formula (6):

Formula (6)

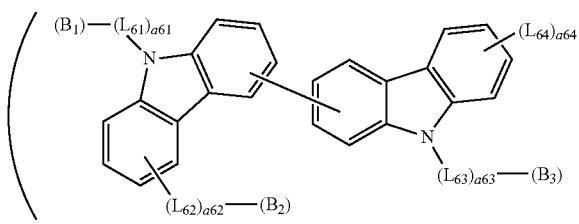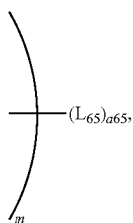

wherein, in Formula (6), $L_{61}$ to $L_{65}$ are each independently selected from a single bond, *—C(=O)—*', *—C(=S)—*', *—O—*', *—N($R_{65}$)—*', a substituted or unsubstituted $C_2$-$C_{60}$ alkylene group, a substituted or unsubstituted $C_3$-$C_{10}$ cycloalkylene group, a substituted or unsubstituted π electron-depleted nitrogen-free $C_1$-$C_{10}$ heterocycloalkylene group, a substituted or unsubstituted $C_3$-$C_{10}$ cycloalkenylene group, a substituted or unsubstituted π electron-depleted nitrogen-free $C_1$-$C_{10}$ heterocycloalkenylene group, a substituted or unsubstituted $C_6$-$C_{60}$ arylene group, a substituted or unsubstituted π electron-depleted nitrogen-free $C_1$-$C_{60}$ heteroarylene group, a substituted or unsubstituted divalent non-aromatic condensed polycyclic group, and a substituted or unsubstituted divalent π electron-depleted nitrogen-free non-aromatic condensed heteropolycyclic group, and *' each indicate a binding site to a neighboring atom, a61 to a65 are each independently an integer selected from 1 to 10, $(L_{65})_{a65}$ is an m-valent linking group or a single bond, wherein m is a natural number greater than or equal to one, when m is one, $(L_{65})_{a65}$ does not exist, when m is a natural number greater than or equal to two, at least one of groups represented by *-$(L_{61})_{a61}$-($B_1$), *-$(L_{62})_{a62}$-($B_2$), *-$(L_{63})_{a63}$-($B_3$), and *-$(L_{64})_{a4}$-($B_4$) is linked to $(L_{65})_{a65}$ or is a single bond linked to $(L_{65})_{a65}$, i) $B_1$ to $B_4$ and $R_{65}$ are each independently linked to $(L_{65})_{a65}$;

ii) $B_1$ to $B_4$ and $R_{65}$ are a single bond linked to $(L_{65})_{a65}$; or iii) $B_1$ to $B_4$ and $R_{65}$ are each independently selected from hydrogen, deuterium, a substituted or unsubstituted $C_1$-$C_{60}$ alkyl group, a substituted or unsubstituted $C_1$-$C_{60}$ alkoxy group, a substituted or unsubstituted $C_3$-$C_{10}$ cycloalkyl group, a substituted or unsubstituted π electron-depleted nitrogen-free $C_1$-$C_{10}$ heterocycloalkyl group, a substituted or unsubstituted $C_3$-$C_{10}$ cycloalkenyl group, a substituted or unsubstituted electron-depleted nitrogen-free $C_1$-$C_{10}$ heterocycloalkenyl group, a substituted or unsubstituted $C_6$-$C_{60}$ aryl group, a substituted or unsubstituted π electron-depleted nitrogen-free $C_1$-$C_{60}$ heteroaryl group, a substituted or unsubstituted monovalent non-aromatic condensed polycyclic group, a substituted or unsubstituted π electron-depleted nitrogen-free monovalent non-aromatic condensed heteropolycyclic group, —Si($Q_1$)($Q_2$)($Q_3$), —N($Q_1$)($Q_2$), and —C(=O)($Q_1$), provided that $B_1$ and $B_2$ are not hydrogen, deuterium, a substituted or unsubstituted $C_1$-$C_{60}$ alkyl group, or a substituted or unsubstituted $C_1$-$C_{60}$ alkoxy group, and at least one substituent of the substituted $C_2$-$C_{60}$ alkylene group, the substituted $C_3$-$C_{10}$ cycloalkylene group, the substituted π electron-depleted nitrogen-free $C_1$-$C_{10}$ heterocycloalkylene group, the substituted $C_3$-$C_{10}$ cycloalkenylene group, the substituted π electron-depleted nitrogen-free $C_1$-$C_{10}$ heterocycloalkenylene group, the substituted $C_6$-$C_{60}$ arylene group, the substituted π electron-depleted nitrogen-free $C_1$-$C_{60}$ heteroarylene group, the substituted divalent non-aromatic condensed polycyclic group, the substituted divalent π electron-depleted nitrogen-free non-aromatic condensed heteropolycyclic group, the substituted $C_1$-$C_{60}$ alkyl group, the substituted $C_1$-$C_{60}$ alkoxy group, the substituted $C_3$-$C_{10}$ cycloalkyl group, the substituted π electron-depleted nitrogen-free $C_1$-$C_{10}$ heterocycloalkyl group, the substituted $C_3$-$C_{10}$ cycloalkenyl group, the substituted π electron-depleted nitrogen-free $C_1$-$C_{10}$ heterocycloalkenyl group, the substituted $C_6$-$C_{60}$ aryl group, the substituted π electron-depleted nitrogen-free $C_1$-$C_{60}$ heteroaryl group, the substituted monovalent non-aromatic condensed polycyclic group, and the substituted π electron-depleted nitrogen-free monovalent non-aromatic condensed heteropolycyclic group is selected from:

deuterium and a $C_1$-$C_{60}$ alkyl group;

a $C_3$-$C_{10}$ cycloalkyl group, a π electron-depleted nitrogen-free $C_1$-$C_{10}$ heterocycloalkyl group, a $C_3$-$C_{10}$ cycloalkenyl group, a π electron-depleted nitrogen-free $C_1$-$C_{10}$ heterocycloalkenyl group, a $C_6$-$C_{60}$ aryl group, a π electron-depleted nitrogen-free $C_1$-$C_{60}$ heteroaryl group, a monovalent non-aromatic condensed polycyclic group, and a π electron-depleted nitrogen-free monovalent non-aromatic condensed heteropolycyclic group;

a $C_3$-$C_{10}$ cycloalkyl group, a π electron-depleted nitrogen-free $C_1$-$C_{10}$ heterocycloalkyl group, a $C_3$-$C_{10}$ cycloalkenyl group, a π electron-depleted nitrogen-free $C_1$-$C_{10}$ heterocycloalkenyl group, a $C_6$-$C_{60}$ aryl group, a π electron-depleted nitrogen-free $C_1$-$C_{60}$ heteroaryl group, a monovalent non-aromatic condensed polycyclic group, and a π electron-depleted nitrogen-free monovalent non-aromatic condensed heteropolycyclic group, each substituted with at least one selected from deuterium, a $C_1$-$C_{60}$ alkyl group, a $C_3$-$C_{10}$ cycloalkyl group, a π electron-depleted nitrogen-free $C_1$-$C_{10}$ heterocycloalkyl group, a $C_3$-$C_{10}$ cycloalkenyl group, a π electron-depleted nitrogen-free $C_1$-$C_{10}$ heterocycloalkenyl group, a $C_6$-$C_{60}$ aryl group, a π electron-depleted nitrogen-free $C_1$-$C_{60}$ heteroaryl group, a monovalent non-aromatic condensed polycyclic group, a π electron-depleted nitrogen-free monovalent non-aromatic condensed heteropolycyclic group, —Si($Q_{21}$)($Q_{22}$)($Q_{23}$), —N($Q_{21}$)($Q_{22}$), and —C(=O)($Q_{21}$); and —Si($Q_{31}$)($Q_{32}$)($Q_{33}$), —N($Q_{31}$)($Q_{32}$), and —C(=O)($Q_{31}$), wherein $Q_1$ to $Q_3$, $Q_{21}$ to $Q_{23}$, and $Q_{31}$ to $Q_{33}$ are each independently selected from a $C_1$-$C_{20}$ alkyl group, a $C_1$-$C_{20}$ alkoxy group, a phenyl group, a biphenyl group, a fluorenyl group, a spiro-bifluorenyl group, a dimethylfluorenyl group, a diphenylfluorenyl group, a carbazolyl group, a phenylcarbazolyl group, a biphenylcarbazolyl group, a dibenzofuranyl group, a phenyldibenzofuranyl group, a diphenyldibenzofuranyl group, a dibenzothiophenyl group, a phenyldibenzothiophenyl group, and a diphenyldibenzothiophenyl group.

17. The organic light-emitting device of claim 15, wherein the emission layer further comprises a phosphorescent dopant.

18. A method of manufacturing an organic light-emitting device comprising a first electrode, a second electrode, and an organic layer disposed between the first electrode and the second electrode, wherein the organic layer comprises an emission layer, and wherein the organic layer comprises a layer comprising the condensed cyclic compound of claim 1, the method comprising:

forming the layer comprising the condensed cyclic compound by solution coating using a composition comprising the condensed cyclic compound and a liquid medium.

* * * * *